United States Patent
Zaczek et al.

(10) Patent No.: US 7,153,491 B2
(45) Date of Patent: *Dec. 26, 2006

(54) USE OF SMALL MOLECULE RADIOLIGANDS TO DISCOVER INHIBITORS OF AMYLOID-BETA PEPTIDE PRODUCTION AND FOR DIAGNOSTIC IMAGING

(75) Inventors: Robert Zaczek, Avondale, PA (US); Richard E. Olson, Wilmington, DE (US); Dietmar A. Seiffert, Boothwyn, PA (US); Lorin Andrew Thompson, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/734,031

(22) Filed: Dec. 11, 2003

(65) Prior Publication Data

US 2005/0019255 A1  Jan. 27, 2005

Related U.S. Application Data

(63) Continuation of application No. 09/573,789, filed on May 17, 2000, now Pat. No. 6,737,038, which is a continuation-in-part of application No. 09/438,901, filed on Nov. 12, 1999, now Pat. No. 6,331,408.

(60) Provisional application No. 60/131,284, filed on Apr. 27, 1999, now abandoned, provisional application No. 60/108,147, filed on Nov. 12, 1998, now abandoned.

(51) Int. Cl.
  *A61K 49/00*  (2006.01)

(52) U.S. Cl. ............ 424/9.2; 424/1.11; 424/1.65; 424/9.1

(58) Field of Classification Search ........ 424/1.11, 424/1.65, 1.81, 1.85, 9.1, 9.2, 9.3, 9.4, 9.5, 424/9.6, 9.7, 9.8; 514/2
See application file for complete search history.

(56) References Cited

U.S. PATENT DOCUMENTS

| | | | |
|---|---|---|---|
| 5,506,242 A | 4/1996 | MacPherson et al. | |
| 5,532,359 A | 7/1996 | Marsters et al. | |
| 5,538,845 A | 7/1996 | Knops et al. | |
| 5,552,419 A | 9/1996 | MacPherson et al. | |
| 5,593,846 A | 1/1997 | Schenk et al. | |
| 5,594,006 A | 1/1997 | Sakamoto et al. | |
| 5,604,102 A | 2/1997 | McConnlogue et al. | |
| 5,672,598 A | 9/1997 | De et al. | |
| 5,703,129 A | 12/1997 | Felsenstein et al. | |
| 5,721,106 A | 2/1998 | Maggio et al. | |
| 5,734,054 A | 3/1998 | Dolle, III et al. | |
| 5,744,346 A | 4/1998 | Chrysler et al. | |
| 5,766,846 A | 6/1998 | Schlossmacher et al. | |
| 5,843,941 A | 12/1998 | Marsters et al. | |
| 5,942,400 A | 8/1999 | Anderson et al. | |
| 6,329,163 B1 | 12/2001 | Anderson et al. | |
| 6,331,408 B1 * | 12/2001 | Zaczek et al. | 435/23 |
| 6,737,038 B1 * | 5/2004 | Zaczek et al. | 424/9.2 |
| 6,878,363 B1 * | 4/2005 | Zaczek et al. | 424/9.1 |
| 2005/0019255 A1 * | 1/2005 | Zaczek et al. | 424/1.69 |

FOREIGN PATENT DOCUMENTS

| | | |
|---|---|---|
| EP | 0276436 | 12/1987 |
| EP | 0606046 | 12/1993 |
| EP | 0652009 | 5/1995 |
| WO | WO 92/00374 | 1/1992 |
| WO | WO 92/06966 | 4/1992 |
| WO | WO-95/09838 | 4/1995 |
| WO | WO 95/22966 | 8/1995 |
| WO | WO 96/29313 | 9/1996 |
| WO | WO-98//38177 | 3/1998 |
| WO | WO 98/15828 | 4/1998 |
| WO | WO 98/22493 | 5/1998 |
| WO | WO-98/22494 | 5/1998 |
| WO | WO 98/28268 | 7/1998 |
| WO | WO 99/66934 | 12/1999 |
| WO | WO-99/67219 | 12/1999 |
| WO | WO-99/67220 | 12/1999 |
| WO | WO 99/67221 | 12/1999 |
| WO | WO 00/24392 | 5/2000 |
| WO | WO-00/28331 | 5/2000 |

OTHER PUBLICATIONS

A. Ahmed et al., *FEBS Letters*, (1984), vol. 174, pp. 76-79.
Arora et al., *J. Med. Chem.*, 30: p. 918 (1987).
P. Becket, M. J. Crimmin, M. H. Davis, and Z. Spavold, *Synlett* (1993), pp. 137-138.
Bock et al., *J. Med. Chem. 1993*, 36, pp. 4276-4292.
Bock et al., *J. Org. Chem 1987*, 52, pp. 3232-3239.
F. A. Carey and R. J. Sundberg, "Advanced Organic Chemistry, Part A," *New York: Plenum Press*, 1990, pp. 304-305, 342-347, 475-479, 695-698.
Chumpradit et al., J. Med. Chem., 32: p. 1431 (1989).
Chumpradit et al., J. Med. Chem., 34: p. 877 (1991).
Ellis et al., *Aust. J. Chem.*, 26,: p. 907 (1973).
Evans, A et al. Org.Synth.68.p. 83-91 (1990).
Glenner and Wong, *Biochem. Biophys. Res. Commun.* 120; pp. 885-890.

(Continued)

Primary Examiner—Dameron L. Jones
(74) Attorney, Agent, or Firm—Kelley Drye & Warren LLP

(57) ABSTRACT

This invention relates to a novel method of screening for inhibitors of beta-amyloid production, and thereby identifying such inhibitors as therapeutics for neurological and other disorders involving APP processing and beta-amyloid production. This invention also relates to identifying macromolecules involved in APP processing and beta-amyloid production. Furthermore, inhibitors identified by the screening method of the present invention are useful in the treatment of neurological disorders, such as Alzheimer's disease, which involve elevated levels of Aβ peptides.

53 Claims, 4 Drawing Sheets

OTHER PUBLICATIONS

Ghosh et al. JACS (2000) 122 pp. 3522-3523.
J. Higaki, D. Quon, Z. Zhong, B. Cordell, "Inhibition of beta-amyloid Formation identifies Proteolytic Precursors and Subcellular Site of Catabolism", Neuron 14, pp. 651-659, 1995.
Jacobson and Reddy, Tetrahedron Letters, vol. 37, No. 46, pp. 8263-8266.
Kabalka et al., J. Label. Compound. Radiopharm., 19: p. 795 (1982).
A. S. Kende et al., Tetrahedron Lett. 1989, 30 (43), 5821-5824.
K. S. Kirshenbaum, K. B. Sharpless, J. Org. Chem. (1985), 50 (11), pp. 1979-1982.
P. Kocienski, *Tetrahedron 1990*, 46, pp. 1767-1782.
Koch et al. , *Chem. Ber*., 124: p. 2091 (1991).
Levitan, D. and Greenwald, I.Nature,377, pp. 351-354,1995.
Lin et al., *PNAS* (2000) 97: pp. 1456-1460.
Mach et al., *J. Med. Chem*., 1993, 36, pp. 3707-3720.
McClure and Axt, *Bioorganic & Medicinal Chemistry Letters*, 8 (1998), pp. 143-146.
Merkushev, *Synthesis*, 923 (1988).
C. F. Nutaitis and M. W. Ledeboer, *Org. Prep. Proced. Int*. (1992), 24 (2), pp. 143-146.
Pratt et al., *Synlett*, May 1998, p. 531.
M. P. Reddy and P. J. Voelker, *Int. J. Pept. Protein Res. 1998*, 31, pp. 345-348.
"Remington's Pharmeceutical Sciences," 17th ed. Mack Publishing Company, Easton, PA, 1985, p. 1418.
D. J. Selkoe, "Cell Biology of the amyloid (beta)-protein precursor and the mechanism of Alzheimer's disease," *Annu. Rev. Cell. Biol*., 1994, 10: pp. 373-403.
Seevers et al., *Chem. Rev*., 82, p. 575 (1982).
Sherrill and Sugg, *J. Org. Chem. 1995*, 60, pp. 730-734.
Vassar et al., *Science* 1999 286: pp. 735-741.
D. A. Walsh, Synthesis, Sep. 1980, p. 677.
Wilbur et al., J. Label. Compound. Radiopharm., 1982 19: p. 1171.
Eckart et al, J. Org. Chem., 1986 51: p. 483-486.
Wolf, Chrisman, Fowler, Lambrecht, "Synthesis of Radiopharmaceuticals and Labeled Compounds Using Short-Lieved Isotopes," in Radiopharmaceuticals and Labeled Compounds, vol. 1, 1973, pp. 345-381.
Book, M.Keen (ed) Receptor binding techniques methods in molecular Biology, vol. 106,Humana Press ,Totowa, New Jersay,1999.
Eckelman et al. J.Nucl. Med ,vol. 20(4) pp. 350-357 (1979).
T.W.Green and Wuts, Proptective Grups in organic Synthesis (Wiley 1991).
Tubis and Wolf, eds Radiopharmacy,Wiley-Interscience New York (1976) vol. 1 p. 345-381(1973).
Wilson et al. J.Org.Chem 51 4833 (1986).
U.S. Pharmacopia—The National Formulary 22nd Revision,Mack Printing Co.Easton, Pa 1990. "Radioactive Pharmaceuticals" relevent sections as per Index on p. 2049.
Book, A. Macowski Medical Imaging Systems ed.Prentice-Hall,Inc Englewood Cliffs NJ(1983).
E.I. Rogaev et al. Nature, vol. 376 pp. 774-778 (1995).
M. G. Natchus et al., "Design and synthesis of conformationally constrained MMP inhibitors," Chemical Abstracts, vol. 129, No. 22, Nov. 30, 1998, abstract No. 290051p.

* cited by examiner

Binding

1: DMSO
2: example 7
3: example 98b
4: example 43
5: example 99
6: example 11
(2-6 at 1uM)

Non-reduced

— 43
— 29
— 18
— 14

Reduced

— 43
— 29
— 18
— 14

1: Starting material
2: I.P. PS-2 N-t.
3: I.P. PS-2 C-t. loop
4: I.P. normal rabbit IgG

USE OF SMALL MOLECULE RADIOLIGANDS TO DISCOVER INHIBITORS OF AMYLOID-BETA PEPTIDE PRODUCTION AND FOR DIAGNOSTIC IMAGING

CROSS-RELATED REFERENCES

This application is a continuation of patent application Ser. No. 09/573,789, filed on May 17, 2000, now U.S. Pat. No. 6,737,038; which is a Continuation-in-part of application Ser. No. 09/438,901, filed on Nov. 12, 1999, now U.S. Pat. No. 6,331,408; which claims benefit of Provisional Application No. 60/131,284, filed on Apr. 27, 1999, now abandoned and Provisional Application No. 60/108,147, flied on Nov. 12, 1998, now abandoned.

FIELD OF THE INVENTION

This invention relates to a novel method of screening for inhibitors of beta-amyloid production, and thereby identifying such inhibitors as therapeutics for neurological and other disorders involving APP processing and beta-amyloid production. This invention also relates to identifying macromolecules involved in APP processing and beta-amyloid production. Furthermore, inhibitors identified by the screening method of the present invention are useful in the treatment of neurological disorders, such as Alzheimer's disease, which involve elevated levels of Aβ peptides.

BACKGROUND OF THE INVENTION

Alzheimer's disease (AD) is a degenerative brain disorder characterized clinically by progressive loss of memory, temporal and local orientation, cognition, reasoning, judgment and emotional stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review, Dennis J. Selkoe; Cell Biology of the amyloid (beta)-protein precursor and the mechanism of Alzheimer's disease, Annu Rev Cell Biol, 1994, 10: 373–403).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to deposition of Aβ in amyloid plaques, Aβ is also found in the walls of meningeal and.parenchymal arterioles, small arteries, capillaries, and sometimes, venules. Aβ was first purified, and a partial amino acid reported, in 1984 (Glenner and Wong, Biochem. Biophys. Res. Commun. 120: 885–890). The isolation and sequence data for the first 28 amino acids are described in U.S. Pat. No 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, α secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

The gene encoding a human aspartic protease that cleaves the β-secretase site of β-amyloid precursor protein has recently been isolated; this gene and encoded protein is designated as BACE (Vassar et al., Science (1999) 286: 735–741) or as memapsin-2 (Lin et al., PNAS (2000) 97: 1456–1460) and is designated herein as "BACE/memapsin-2".

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familial forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that βP depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or γ secretases could thereby reduce production of Aβ, which, thereby, could reduce or prevent the neurological disorders associated with Aβ protein.

It is believed that several macromolecules, some of which have proteolytic activity, are involved in the processing of amyloid precursor protein (APP). This processing leads to several products including the β-amyloid peptides (Aβ) believed etiologically important in Alzheimers Disease. We have discovered novel tagged compounds, functional in themselves as Aβ inhibitors, for use in identifying a site or sites on one or more macromolecules critical to the processing of β APP and the production of Aβ. We have discovered novel tagged compounds which inhibit the proteolytic activity leading to production of Aβ by interacting with one or more macromolecules critical to the processing of APP and the production of Aβ. We have also discovered a site of action of these tagged compounds using radioisotope tagged derivatives of a compound of Formula (I).

Three examples of tagged compounds include (I-7T), (I-11T), and (I-43T):

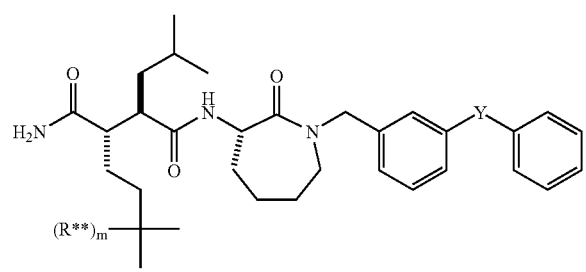

(I-#)

| | |
|---|---|
| $R^{**}=^{1}H$; Y=—O—; | (I-7) |
| $R^{**}=^{3}H$; Y=—O—; and | (I-7T) |
| $R^{**}=^{1}H$; Y=—C(=O)—; | (I-11) |
| $R^{**}=^{3}H$; Y=—C(=O)—; and | (I-11T) |

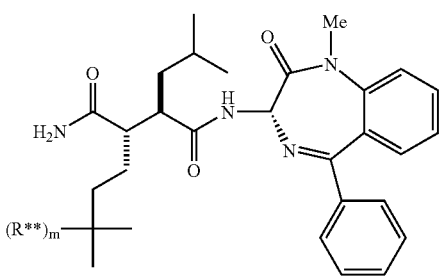

(I-#)

| | |
|---|---|
| $R^{**}=^{1}H$; | (I-43) |
| $R^{**}=^{3}H$. | (I-43T) |

The concentration of Compound (I-7) leading to half-maximal inhibition ($IC_{50}$) of proteolytic activity leading to Aβ production in $HEK_{293}$ cells expressing APP 695 wt is similar to the concentration leading to half-maximal inhibition ($IC_{50}$) of Compound (I-7T) binding to membranes derived from the same cell line. The correlation holds for compounds (I-11T) and (I-43T). Also using a compound of Formula (I), we have discovered a macromolecule containing a binding site of action for compounds of Formula (I) critical to the processing of APP and the production of Aβ.

Furthermore, we have discovered through competitive binding studies that there is a good correlation between the ability of a series of compounds to inhibit the proteolytic activity leading to production of Aβ and to inhibit the binding of Compound (I-7T), (I-11T), or (I-43T) to said membranes. Thus, the binding of Compound (I-7T), (I-11T), or (I-43T) to relevant tissues and cell lines, membranes derived from relevant tissues and cell lines, as well as isolated macromolecules and complexes of isolated macromolecules, is useful in the identification of inhibitors of Aβ production through competitive binding assays. Furthermore, such competitive binding assays are useful in identification of inhibitors of proteolytic activity leading to Aβ production for the treatment of Alzheimer's disease. Furthermore, such competitive binding assays are useful in identification of inhibitors of proteolytic activity leading to Aβ production for the treatment of neurological disorders and other disorders involving Aβ, APP, and/or Aβ/APP associated macromolecules, and other macromolecules associated with the site of Compound (I-7T), (I-11T), or (I-43T) binding.

SUMMARY OF THE INVENTION

One object of the present invention is to provide a novel method of screening for inhibitors of beta-amyloid production, and thereby identifying such inhibitors as therapeutics for neurological and other disorders involved in APP processing and beta-amyloid production. The method comprises 1) contacting a potential inhibitor of beta-amyloid production and a tagged inhibitor of beta-amyloid production with at least one macromolecule involved in the processing of APP and the production of beta-amyloid peptide, said macromolecule containing a binding site specific for said tagged inhibitor of beta-amyloid production; 2) separating the tagged inhibitor of beta-amyloid production bound to said macromolecule from the tagged inhibitor of beta-amyloid production free from said macromolecule; and 3) determining an inhibitory concentration of the potential inhibitor of beta-amyloid production from the concentration of tagged inhibitor of beta-amyloid production bound to said macromolecule.

It is another object of the present invention to provide the use of a tagged inhibitor of beta-amyloid production to identify macromolecules involved in APP processing.

It is another object of the present invention to provide the macromolecules involved in APP processing which a tagged inhibitor of beta-amyloid production binds to specifically.

It is another object of the present invention to provide the use of macromolecules involved in APP processing, which a tagged inhibitor of beta-amyloid production binds to specifically, for the identification of inhibitors as therapeutics for neurological and other disorders involved in APP processing and beta-amyloid production.

It is another object of the present invention to provide the use of macromolecules involved in APP processing, which a tagged inhibitor of beta-amyloid production binds to specifically, for the assaying of inhibitors of beta-amyloid production.

It is another object of the present invention to provide pharmaceutical compositions comprising a pharmaceutically acceptable carrier and a therapeutically effective amount of an inhibitor of beta-amyloid production, or a pharmaceutically acceptable salt or prodrug form thereof, identified by the screening assay of the present invention.

It is another object of the present invention to provide a method for treating degenerative neurological disorders involving beta-amyloid production, including Alzheimer's disease, comprising administering to a host in need of such treatment a therapeutically effective amount of an inhibitor of beta-amyloid production, or a pharmaceutically acceptable salt or prodrug form thereof, identified by the screening assay of the present invention.

It is another object of the present invention to provide an inhibitor of beta-amyloid production which interacts with the binding site for a compound of Formula (I-7T) on a macromolecule involved in the production of beta-amyloid peptide.

These and other objects, which will become apparent during the following detailed description, have been achieved by the inventors' discovery that compounds of Formula (I):

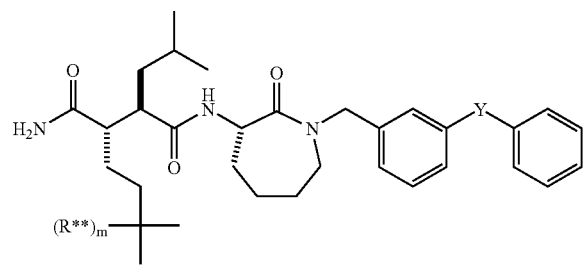

(I-#)

R**=¹H; Y=—O—; (I-7)

R**=³H; Y=—O—; and (I-7T)

R**=¹H; Y=—C(=O)—; (I-11)

R**=³H; Y=—C(=O)—; and (I-11T)

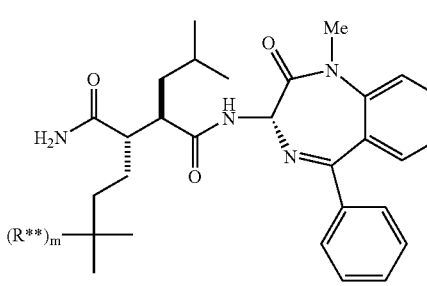

(I-#)

R**=¹H; (I-43)

R**=³H; (I-43T)

bind specifically to a binding site on a macromolecule or a complex of macromolecules involved in APP processing to produce reduction of Aβ peptide production. For example, the concentration of Compound (I-7) leading to half-maximal inhibition ($IC_{50}$) of Aβ production in $HEK_{293}$ cells expressing APP 695 wt is similar to the concentration leading to half-maximal inhibition ($IC_{50}$) of Compound (I-7T) binding to membranes derived from the same cell line.

It is another object of the present invention to provide radiolabeled inhibitors of APP processing and/or the production of beta-amyloid production for use in methods of in vivo diagnostic imaging in the diagnosis of diseases involving APP processing and/or the production of beta-amyloid production. Also provided in the present invention are methods of in vivo diagnostic imaging comprising administering to a subject a diagnostically effective amount of a radiolabeled inhibitor of APP processing and/or the production of beta-amyloid production FIG. 1 illustrates the correlation between results of the Radioligand Competition Binding Assay and the cross-linking assay of Example 103.

DETAILED DESCRIPTION OF PREFERRED EMBODIMENTS

Figure 1:
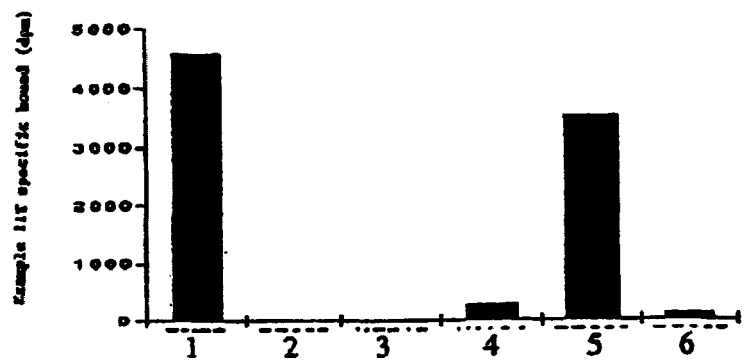
Figure 1:
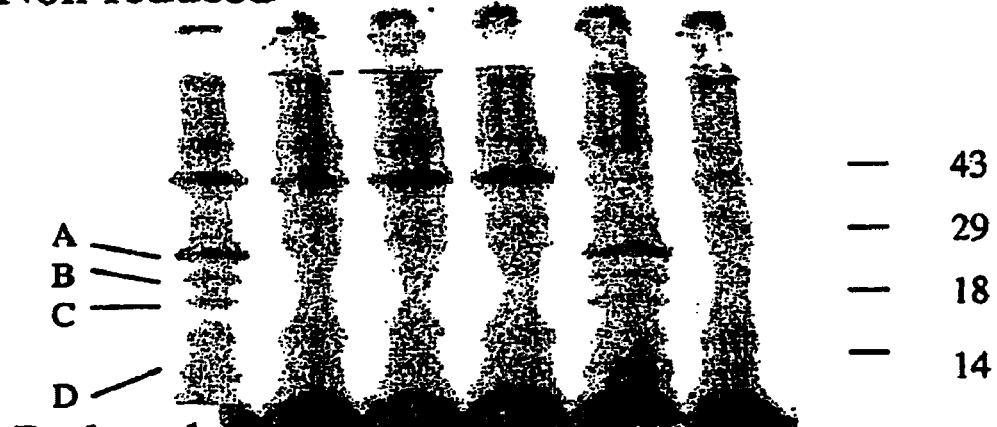
Figure 1:
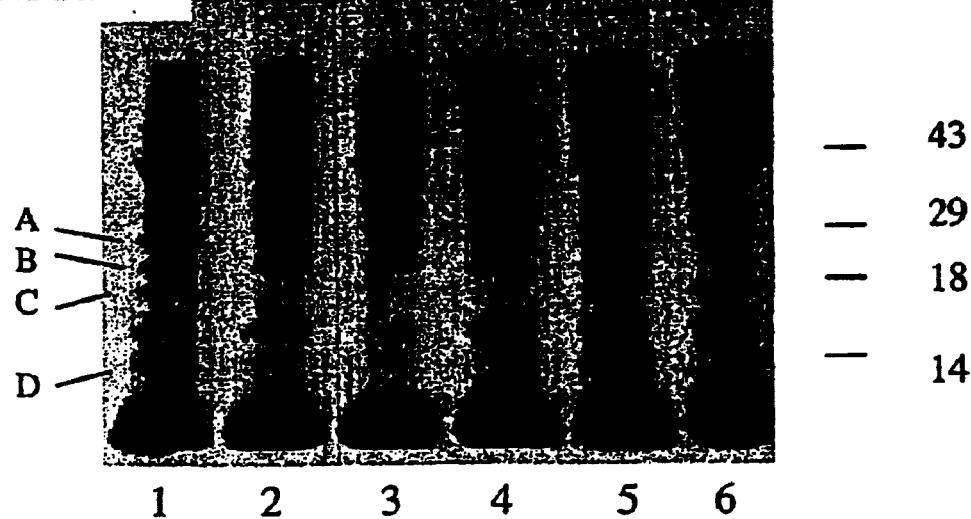

[1] Thus, in a first embodiment, the present invention provides a method of screening for inhibitors of beta-amyloid production comprising, 1) contacting a potential inhibitor of beta-amyloid production and a tagged inhibitor of beta-amyloid production with at least one macromolecule involved in the processing of APP and/or the production of beta-amyloid peptide, said macromolecule containing a binding site specific for said tagged inhibitor of beta-amyloid production;

2) separating the tagged inhibitor of beta-amyloid production bound to said macromolecule from the tagged inhibitor of beta-amyloid production free from said macromolecule; and 3) determining an inhibitory concentration of the potential inhibitor of beta-amyloid production from the concentration of tagged inhibitor of beta-amyloid production bound to said macromolecule.

[1a] The present invention provides the foregoing method wherein the macromolecule is selected from:

(1) presenilin-1;
(2) presenilin-2;
(3) β secretase;
(4) α secretase;
(5) γ secretase; or
(6) BACE/memapsin 2.

[2] In a more preferred embodiment the present invention provides a method wherein the tagged inhibitor of beta-amyloid production comprises a radiolabeled inhibitor of beta-amyloid production, a fluorescence labeled inhibitor of beta-amyloid production or a biotin labeled inhibitor of beta-amyloid production.

[3] In a more preferred embodiment the tagged inhibitor of beta-amyloid production comprises a radiolabeled inhibitor of beta-amyloid production.

[4] In an even more preferred embodiment the present invention provides a method wherein the tagged inhibitor of beta-amyloid production comprises a tritium or iodine radiolabeled inhibitor of beta-amyloid production.

[5] In an even more preferred embodiment the present invention provides a method wherein the tagged inhibitor of beta-amyloid production comprises a tritium labeled inhibitor of beta-amyloid production.

[6] In an even more preferred embodiment the present invention, provides a method wherein the tagged inhibitor of beta-amyloid production comprises a compound of the Formula (I):

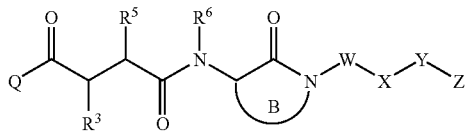

wherein:
at least one atom of the compound of the Formula (I) is radiolabeled;
Q is —$NR^1R^2$;
$R^1$, at each occurrence, is independently selected from:
H;
$C_1$–$C_6$ alkyl substituted with 0–3 $R^{1a}$;
$C_3$–$C_{10}$ carbocycle substituted with 0–3 $R^{1b}$;
$C_6$–$C_{10}$ aryl substituted with 0–3 $R^{1b}$; and
5 to 10 membered heterocycle substituted with 0–3 $R^{1b}$;
$R^{1a}$, at each occurrence, is independently selected from H, $C_1$–$C_6$ alkyl, $OR^{14}$, Cl, F, Br, I, =O, CN, $NO_2$, $NR^{15}R^{16}$, phenyl, $CF_3$;
$C_3$–$C_{10}$ carbocycle substituted with 0–3 $R^{1b}$;
$C_6$–$C_{10}$ aryl substituted with 0–3 $R^{1b}$; and
5 to 10 membered heterocycle substituted with 0–3 $R^{1b}$;
$R^{1b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
$R^2$ is independently selected from H, OH, $C_1$–$C_6$ alkyl, $C_1$–$C_6$ alkoxy, $C_3$–$C_{10}$ carbocycle, $C_6$–$C_{10}$ aryl and 5 to 10 membered heterocycle;
$R^3$ is $C_1$–$C_6$ alkyl substituted with 0–1 $R^4$;
$R^4$ is H, OH, $C_1$–$C_6$ alkoxy, $C_1$–$C_6$ alkyl, $C_2$–$C_6$ alkenyl, $C_2$–$C_6$ alkynyl, $C_3$–$C_{10}$ carbocycle, $C_6$–$C_{10}$ aryl, or 5 to 10 membered heterocycle;
$R^5$ is H, $OR^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle substituted with 0–3 $R^{5c}$;
$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle substituted with 0–3 $R^{5c}$;
$R^{5c}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3$R^{6b}$;
$R^{6a}$, at each occurrence, is independently selected from H, $C_1$–$C_6$ alkyl, $OR^{14}$, Cl, F, Br, I, =O, CN, $NO_2$, $NR^{15}R^{16}$, phenyl or $CF_3$;
$R^{6b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
W is —$(CR^8R^{8a})_p$—;
p is 0 to 4;

$R^8$ and $R^{8a}$, at each occurrence, are independently selected from H, $C_1$–$C_4$ alkyl, $C_2$–$C_4$ alkenyl, $C_2$–$C_4$ alkynyl and $C_3$–$C_8$ cycloalkyl;
X is a bond;
$C_6$–$C_{10}$ aryl substituted with 0–3 $R^{Xb}$;
$C_3$–$C_{10}$ carbocycle substituted with 0–3 $R^{Xb}$; or
5 to 10 membered heterocycle substituted with 0–3 $R^{Xb}$;
$R^{Xb}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
Y is a bond or —$(CR^9R^{9a})_t$—V—$(CR^9R^{9a})_u$—;
t is 0 to 3;
u is 0 to 3;
$R^9$ and $R^{9a}$, at each occurrence, are independently selected from H, $C_1$–$C_6$ alkyl or $C_3$–$C_8$ cycloalkyl;
V is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—;
Z is H;
$C_1$–$C_8$ alkyl substituted with 0–2 $R^{12}$;
$C_2$–$C_4$ alkenyl substituted with 0–2 $R^{12}$;
$C_2$–$C_4$ alkynyl substituted with 0–2 $R^{12}$;
$C_6$–$C_{10}$ aryl substituted with 0–4 $R^{12b}$;
$C_3$–$C_{10}$ carbocycle substituted with 0–4 $R^{12b}$; or
5 to 10 membered heterocycle substituted with 0–3 $R^{12b}$;
$R^{12}$ is $C_6$–$C_{10}$ aryl substituted with 0–4 $R^{12b}$;
$C_3$–$C_{10}$ carbocycle substituted with 0–4 $R^{12b}$; or
5 to 10 membered heterocycle substituted with 0–3 $R^{12b}$;
$R^{12b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
B is a 5 to 10 membered lactam, wherein the lactam is saturated, partially saturated or unsaturated; wherein each additional lactam carbon is substituted with 0–2 $R^{11}$; and, optionally, the lactam contains a heteroatom selected from —O—, —S—, —S(=O)—, —S(=O)$_2$—, —N= and —N($R^{10}$)—;
$R^{10}$ is H, C(=O)$R^{17}$, C(=O)$OR^{17}$, C(=O)$NR^{18}R^{19}$, S(=O)$_2$$NR^{18}R^{19}$, S(=O)$_2$$R^{17}$;
$C_1$–$C_6$ alkyl optionally substituted with $R^{10a}$;
$C_6$–$C_{10}$ aryl substituted with 0–4 $R^{10b}$;
$C_3$–$C_{10}$ carbocycle substituted with 0–3 $R^{10b}$; or
5 to 10 membered heterocycle optionally substituted with 0–3 $R^{10b}$;
$R^{10a}$, at each occurrence, is independently selected from H, $C_1$–$C_6$ alkyl, $C_3$–$C_6$ cycloalkyl, $OR^{14}$, Cl, F, Br, I, =O, CN, $NO_2$, $NR^{15}R^{16}$, phenyl or $CF_3$;
$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
$R^{11}$ is $C_1$–$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, S(=O)$_2$$NR^{18}R^{19}$, $CF_3$;
$C_1$–$C_6$ alkyl optionally substituted with $R^{11a}$;
$C_6$–$C_{10}$ aryl substituted with 0–3 $R^{11b}$;
$C_3$–$C_{11}$ carbocycle substituted with 0–3 $R^{11b}$; or
5 to 10 membered heterocycle substituted with 0–3 $R^{11b}$;
alternatively, two $R^{11}$ substituents on the same carbon atoms may be combined to form a $C_3$–$C_6$ carbocycle;
alternatively, two $R^{11}$ substituents on adjacent carbon atoms may be combined to form a $C_3$–$C_6$ carbocycle or a benzo fused radical, wherein said benzo fused radical is substituted with 0–3 $R^{13}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, phenyl or $CF_3$;

$R^{11b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

$R^{14}$ is H, phenyl, benzyl, $C_1$–$C_6$ alkyl, or $C_2$–$C_6$ alkoxyalkyl;

$R^{15}$, at each occurrence, is independently selected from H, $C_1$–$C_6$ alkyl, benzyl, phenethyl, —C(=O)—($C_1$–$C_6$ alkyl) and —S(=O)$_2$—($C_1$–$C_6$ alkyl);

$R^{16}$, at each occurrence, is independently selected from H, OH, $C_1$–$C_6$ alkyl, benzyl, phenethyl, —C(=O)—($C_1$–$C_6$ alkyl) and —S(=O)$_2$—($C_1$–$C_6$ alkyl);

$R^{17}$ is H, phenyl, benzyl, $C_1$–$C_6$ alkyl, or $C_2$–$C_6$ alkoxyalkyl;

$R^{18}$, at each occurrence, is independently selected from H, $C_1$–$C_6$ alkyl, benzyl, phenethyl, —C(=O)—($C_1$–$C_6$ alkyl) and —S(=O)$_2$—($C_1$–$C_6$ alkyl); and $R^{19}$, at each occurrence, is independently selected from H, OH, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{19b}$ is H, $C_1$–$C_6$ alkyl, $C_3$–$C_8$ cycloalkyl, phenyl, benzyl or phenethyl; and $R^{20}$ is H or $C_1$–$C_6$ alkyl.

[ ] In an even further more preferred embodiment the present invention, provides a method wherein Q of a compound of Formula (I) is —$NH_2$.

[7] In an even further more preferred embodiment the present invention, provides a method wherein $R^3$ of a compound of Formula (I) is $C_3$–$C_6$ alkyl.

[8] In an even further more preferred embodiment the present invention, provides a method wherein $R^3$ of a compound of Formula (I) is $C_3$–$C_6$ alkyl substituted with about 1 to about 4 $^3H$;

[ ] In an even further more preferred embodiment the present invention, provides a method wherein Q is —$NH_2$, and $R^3$ is $C_3$–$C_6$ alkyl substituted with about 1 to about 4 $^3H$.

[9] In an even further more preferred embodiment the present invention, provides a method wherein the tagged inhibitor of beta-amyloid production comprises a compound of the Formula (II):

(II)

wherein:
at least one atom of the compound of the Formula (II) is radiolabeled.

[10] In an even further more preferred embodiment the present invention, provides a method wherein $R^3$, in a compound of Formula (II), is $C_3$–$C_6$ alkyl substituted with about 1 to about 4 $^3H$.

[11] In a most preferred embodiment the present invention, provides a method wherein the tagged inhibitor of beta-amyloid production comprises a compound of Formula:

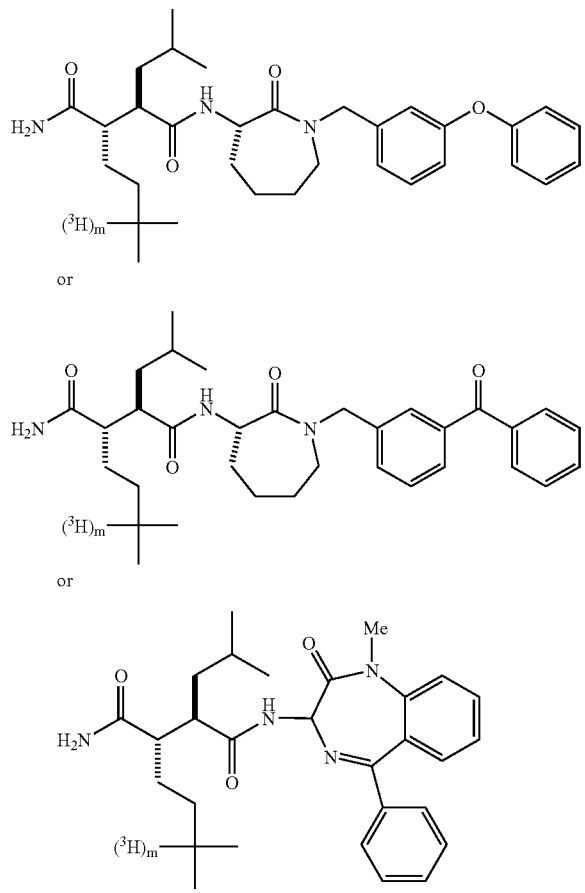

wherein m is about 2.

[12] In a further most preferred embodiment the present invention, provides a method wherein the tagged inhibitor of beta-amyloid production comprises a compound of Formula (I-43T)

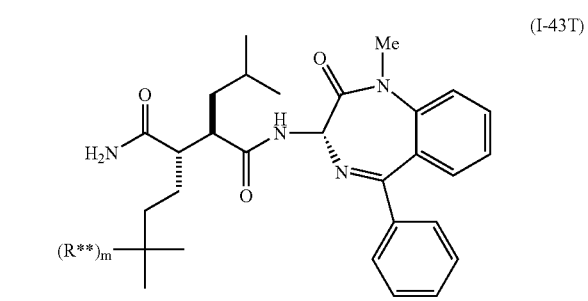

(I-43T)

wherein m is about 2.

[ ] In yet another preferred embodiment the present invention provides a method wherein the tagged inhibitor of beta-amyloid production comprises a compound selected from U.S. Pat. No. 5,703,129; PCT application WO98/28268; PCT application WO98/22441; PCT application WO98/22433; PCT application WO98/22430; PCT application WO98/22493; PCT application WO98/22494; PCT application WO98/38177; or PCT application WO95/09838; wherein the compound has been tagged for purposes of the invention.

[13] In another preferred embodiment the present invention provides a method wherein at least one macromolecule involved in the processing of APP and the production of beta-amyloid peptide comprises presenilin 1 or a fragment of presenilin 1.

[14] In another preferred embodiment the present invention provides a method wherein the macromolecule involved in the processing of APP and/or the production of beta-amyloid peptide comprises:
(1) presenilin-1;
(2) presenilin-2;
(3) β secretase;
(4) α secretase;
(5) γ secretase; or
(6) BACE/memapsin 2;

or any fragment or derivative thereof.

[ ] In another preferred embodiment the present invention provides a method wherein at least one macromolecule involved in the processing of APP and the production of beta-amyloid peptide comprises either 1) presenilin 1 or a fragment of presenilin 1 or 2) presenilin 2 or a fragment of presenilin 2; but not both.

[15] In yet another preferred embodiment the present invention provides a method wherein the inhibitory concentration is half maximal inhibitory concentration.

[16] In a second embodiment, the present invention provides a pharmaceutical composition comprising a pharmaceutically acceptable carrier and a therapeutically effective amount of an inhibitor of beta-amyloid production identified by the screening assay of claim 1 or a pharmaceutically acceptable salt or prodrug form thereof.

[17] In a third embodiment, the present invention provides a method for treating degenerative neurological disorders involving beta-amyloid production comprising administering to a host in need of such treatment a therapeutically effective amount of an inhibitor of beta-amyloid production identified by the screening assay of claim 1 or a pharmaceutically acceptable salt or prodrug form thereof.

[18] In a preferred third embodiment the degenerative neurological disorder is Alzheimer's Disease.

[19] In a fourth embodiment, the present invention provides a method of identifying a macromolecule involved in APP processing comprising
1) contacting a tagged inhibitor of beta-amyloid production with material suspected to contain a macromolecule involved in APP processing;
2) separating a complex comprising a tagged inhibitor of beta-amyloid production and a macromolecule involved in APP processing; and
3) identifying the complex.

[20] In a preferred fourth embodiment the present invention provides a method wherein the tagged inhibitor of beta-amyloid production comprises a radiolabeled inhibitor of beta-amyloid production, a fluorescence labeled inhibitor of beta-amyloid production, a biotin labeled inhibitor of beta-amyloid production, a photoaffinity labeled inhibitor of beta-amyloid production, or any combination of tags thereof in one inhibitor of beta-amyloid production.

[21] In a preferred fourth embodiment the present invention provides a method wherein the tagged inhibitor of beta-amyloid production comprises a radiolabeled inhibitor of beta-amyloid production.

[22] In a more preferred fourth embodiment the present invention provides a method wherein the tagged inhibitor of beta-amyloid production comprises a tritium labeled inhibitor of beta-amyloid production.

[23] In a more preferred fourth embodiment the present invention provides a method wherein the tagged inhibitor of beta-amyloid production comprises a compound of Formula (I):

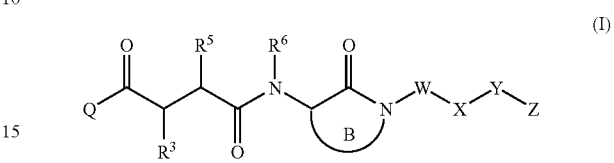

wherein:
at least one atom of the compound of the Formula (I) is radiolabeled;
Q is —NR$^1$R$^2$;
R$^1$, at each occurrence, is independently selected from:
H;
C$_1$–C$_6$ alkyl substituted with 0–3 R$^{1a}$;
C$_3$–C$_{10}$ carbocycle substituted with 0–3 R$^{1b}$;
C$_6$–C$_{10}$ aryl substituted with 0–3 R$^{1b}$; and
5 to 10 membered heterocycle substituted with 0–3 R$^{1b}$;
R$^{1a}$, at each occurrence, is independently selected from H, C$_1$–C$_6$ alkyl, OR$^{14}$, Cl, F, Br, I, =O, CN, NO$_2$, NR$^{15}$R$^{16}$, phenyl, CF$_3$;
C$_3$–C$_{10}$ carbocycle substituted with 0–3 R$^{1b}$;
C$_6$–C$_{10}$ aryl substituted with 0–3 R$^{1b}$; and
5 to 10 membered heterocycle substituted with 0–3 R$^{1b}$;
R$^{1b}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, or CF$_3$;
R$^2$ is independently selected from H, OH, C$_1$–C$_6$ alkyl, C$_1$–C$_6$ alkoxy, C$_3$–C$_{10}$ carbocycle, C$_6$–C$_{10}$ aryl and 5 to 10 membered heterocycle;
R$^3$ is C$_1$–C$_6$ alkyl substituted with 0–1 R$^4$;
R$^4$ is H, OH, C$_1$–C$_6$ alkoxy, C$_1$–C$_6$ alkyl, C$_2$–C$_6$ alkenyl, C$_2$–C$_6$ alkynyl, C$_3$–C$_{10}$ carbocycle, C$_6$–C$_{10}$ aryl, or 5 to 10 membered heterocycle;
R$^5$ is H, OR$^{14}$;
C$_1$–C$_6$ alkyl substituted with 0–3 R$^{5b}$;
C$_1$–C$_6$ alkoxy substituted with 0–3 R$^{5b}$;
C$_2$–C$_6$ alkenyl substituted with 0–3 R$^{5b}$;
C$_2$–C$_6$ alkynyl substituted with 0–3 R$^{5b}$;
C$_3$–C$_{10}$ carbocycle substituted with 0–3 R$^{5c}$;
C$_6$–C$_{10}$ aryl substituted with 0–3 R$^{5c}$; or
5 to 10 membered heterocycle substituted with 0–3 R$^{5c}$;
R$^{5b}$, at each occurrence, is independently selected from:
H, C$_1$–C$_6$ alkyl, CF$_3$, OR$^{14}$, Cl, F, Br, I, =O, CN, NO$_2$, NR$^{15}$R$^{16}$;
C$_3$–C$_{10}$ carbocycle substituted with 0–3 R$^{5c}$;
C$_6$–C$_{10}$ aryl substituted with 0–3 R$^{5c}$; or
5 to 10 membered heterocycle substituted with 0–3 R$^{5c}$;
R$^{5c}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, or CF$_3$;
R$^6$ is H;
C$_1$–C$_6$ alkyl substituted with 0–3 R$^{6a}$;
C$_3$–C$_{10}$ carbocycle substituted with 0–3 R$^{6b}$; or
C$_6$–C$_{10}$ aryl substituted with 0–3R$^{6b}$;

$R^{6a}$, at each occurrence, is independently selected from H, $C_1$–$C_6$ alkyl, $OR^{14}$, Cl, F, Br, I, =O, CN, $NO_2$, $NR^{15}R^{16}$, phenyl or $CF_3$;

$R^{6b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

W is —$(CR^8R^{8a})_p$—;

p is 0 to 4;

$R^8$ and $R^8a$, at each occurrence, are independently selected from H, $C_1$–$C_4$ alkyl, $C_2$–$C_4$ alkenyl, $C_2$–$C_4$ alkynyl and $C_3$–$C_8$ cycloalkyl;

X is a bond;
  $C_6$–$C_{10}$ aryl substituted with 0–3 $R^{Xb}$;
  $C_3$–$C_{10}$ carbocycle substituted with 0–3 $R^{Xb}$; or
  5 to 10 membered heterocycle substituted with 0–3 $R^{Xb}$;

$R^{Xb}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

Y is a bond or —$(CR^9R^{9a})_t$—V—$(CR^9R^{9a})_u$—;

t is 0 to 3;

u is 0 to 3;

$R^9$ and $R^{9a}$, at each occurrence, are independently selected from H, $C_1$–$C_6$ alkyl or $C_3$–$C_8$ cycloalkyl;

V is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—;

Z is H;
  $C_1$–$C_8$ alkyl substituted with 0–2 $R^{12}$;
  $C_2$–$C_4$ alkenyl substituted with 0–2 $R^{12}$;
  $C_2$–$C_4$ alkynyl substituted with 0–2 $R^{12}$;
  $C_6$–$C_{10}$ aryl substituted with 0–4 $R^{12b}$;
  $C_3$–$C_{10}$ carbocycle substituted with 0–4 $R^{12b}$; or
  5 to 10 membered heterocycle substituted with 0–3 $R^{12b}$;

$R^{12}$ is $C_6$–$C_{10}$ aryl substituted with 0–4 $R^{12b}$;
  $C_3$–$C_{10}$ carbocycle substituted with 0–4 $R^{12b}$; or
  5 to 10 membered heterocycle substituted with 0–3 $R^{12b}$;

$R^{12b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

B is a 5 to 10 membered lactam, wherein the lactam is saturated, partially saturated or unsaturated; wherein each additional lactam carbon is substituted with 0–2 $R^{11}$; and, optionally, the lactam contains a heteroatom selected from —O—, —S—, —S(=O)—, —S(=O)$_2$—, —N=, and —N($R^{10}$);

$R^{10}$ is H, C(=O)$R^{17}$, C(=O)$OR^{17}$, C(=O)$NR^{18}R^{19}$, S(=O)$_2$$NR^{18}R^{19}$, S(=O)$_2$$R^{17}$;
  $C_1$–$C_6$ alkyl optionally substituted with $R^{10a}$;
  $C_6$–$C_{10}$ aryl substituted with 0–4 $R^{10b}$;
  $C_3$–$C_{10}$ carbocycle substituted with 0–3 $R^{10b}$; or
  5 to 10 membered heterocycle optionally substituted with 0–3 $R^{10b}$;

$R^{10a}$, at each occurrence, is independently selected from H, $C_1$–$C_6$ alkyl, $C_3$–$C_6$ cycloalkyl, $OR^{14}$, Cl, F, Br, I, =O, CN, $NO_2$, $NR^{15}R^{16}$, phenyl or $CF_3$;

$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

$R^{11}$ is $C_1$–$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, S(=O)$_2$$NR^{18}R^{19}$, $CF_3$;
  $C_1$–$C_6$ alkyl optionally substituted with $R^{11a}$;
  $C_6$–$C_{10}$ aryl substituted with 0–3 $R^{11b}$;
  $C_3$–$C_{10}$ carbocycle substituted with 0–3 $R^{11b}$; or
  5 to 10 membered heterocycle substituted with 0–3 $R^{11b}$;

alternatively, two $R^{11}$ substituents on the same carbon atoms may be combined to form a $C_3$–$C_6$ carbocycle;

alternatively, two $R^{11}$ substituents on adjacent carbon atoms may be combined to form a $C_3$–$C_6$ carbocycle or a benzo fused radical, wherein said benzo fused radical is substituted with 0–3 $R^{13}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, phenyl or $CF_3$;

$R^{11b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

$R^{14}$ is H, phenyl, benzyl, $C_1$–$C_6$ alkyl, or $C_2$–$C_6$ alkoxyalkyl;

$R^{15}$, at each occurrence, is independently selected from H, $C_1$–$C_6$ alkyl, benzyl, phenethyl, —C(=O)—($C_1$–$C_6$ alkyl) and —S(=O)$_2$—($C_1$–$C_6$ alkyl);

$R^{16}$, at each occurrence, is independently selected from H, OH, $C_1$–$C_6$ alkyl, benzyl, phenethyl, —C(=O)—($C_1$–$C_6$ alkyl) and —S(=O)$_2$—($C_1$–$C_6$ alkyl);

$R^{17}$ is H, phenyl, benzyl, $C_1$–$C_6$ alkyl, or $C_2$–$C_6$ alkoxyalkyl;

$R^{18}$, at each occurrence, is independently selected from H, $C_1$–$C_6$ alkyl, benzyl, phenethyl, —C(=O)—($C_1$–$C_6$ alkyl) and —S(=O)$_2$—($C_1$–$C_6$ alkyl); and $R^{19}$, at each occurrence, is independently selected from H, OH, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{19b}$ is H, $C_1$–$C_6$ alkyl, $C_3$–$C_8$ cycloalkyl, phenyl, benzyl or phenethyl; and $R^{20}$ is H or $C_1$–$C_6$ alkyl.

[24] In an even more preferred fourth embodiment the present invention provides a method wherein the tagged inhibitor of beta-amyloid production comprises a compound of the Formula (I-7T):

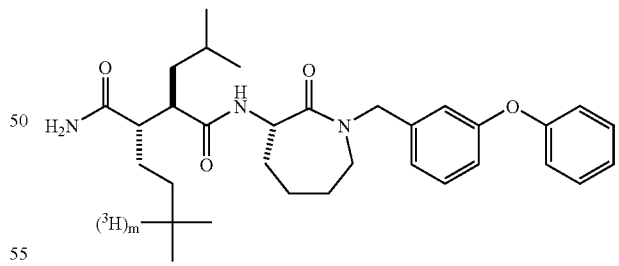

(I-7T)

wherein m is about 2.

[26] In another preferred fourth embodiment the present invention provides a method wherein the tagged inhibitor of beta-amyloid production is radiolabeled and photoaffinity labeled.

[27] In a more preferred fourth embodiment the present invention provides a method wherein the tagged inhibitor of beta-amyloid production comprises a compound of the Formula (I-11T):

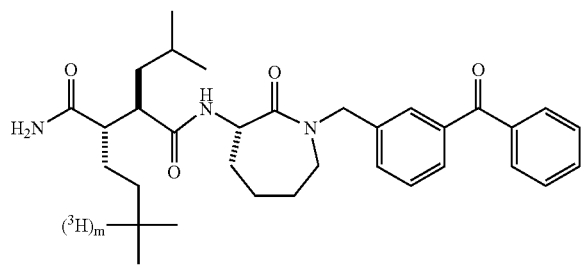

(I-11T)

wherein m is about 2.

[ ] In an even further more preferred fourth embodiment the present invention provides a method wherein the tagged inhibitor of beta-amyloid production comprises a compound of the Formula (I-43T):

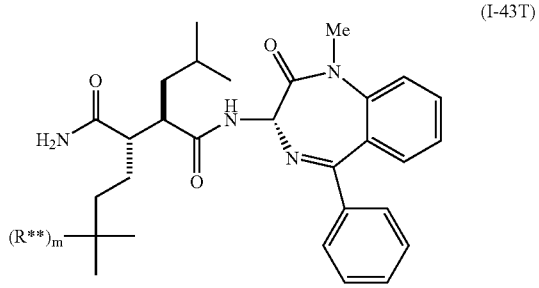

(I-43T)

wherein m is about 2.

[28] In fifth embodiment the present invention provides a macromolecule involved in APP processing which a tagged inhibitor of beta-amyloid production binds to specifically.

[29] In a preferred fifth embodiment the present invention provides a macromolecule wherein the the tagged inhibitor of beta-amyloid production comprises a radiolabeled inhibitor of beta-amyloid production, a fluorescence labeled inhibitor of beta-amyloid production, a biotin labeled inhibitor of beta-amyloid production, a photoaffinity labeled inhibitor of beta-amyloid production, or any combination of tags thereof in one inhibitor of beta-amyloid production.

[30] In a preferred fifth embodiment the present invention provides a macromolecule wherein the tagged inhibitor of beta-amyloid production comprises a radiolabeled inhibitor of beta-amyloid production.

[31] In a more preferred fifth embodiment the present invention provides a macromolecule wherein the tagged inhibitor of beta-amyloid production comprises a compound of the Formula (I-7T):

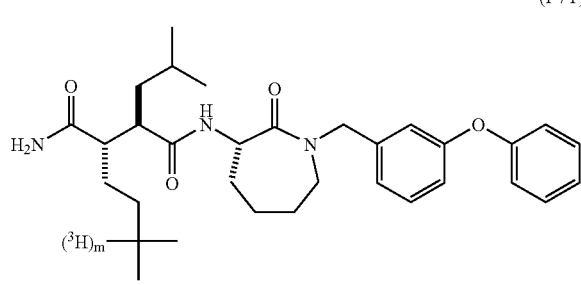

(I-7T)

wherein m is about 2.

[32] In another preferred fifth embodiment the present invention provides a macromolecule wherein the tagged inhibitor of beta-amyloid production comprises a compound of the Formula (I-11T):

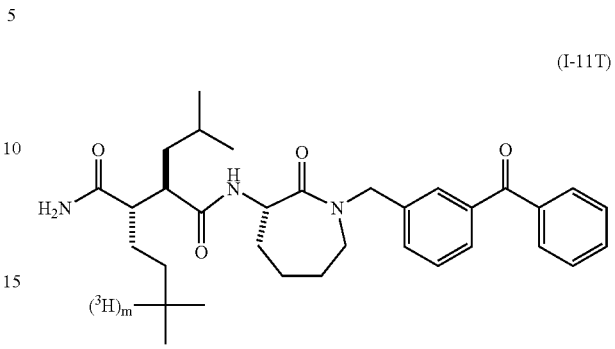

(I-11T)

wherein m is about 2.

[33] In another preferred fifth embodiment the present invention provides a macromolecule wherein the tagged inhibitor of beta-amyloid production comprises a compound of the Formula (I-43T):

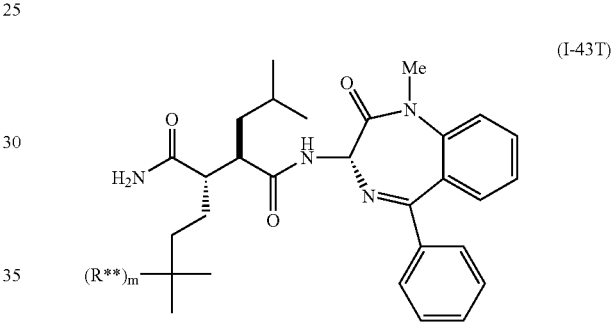

(I-43T)

wherein m is about 2.

[34] In another preferred fifth embodiment the present invention provides a macromolecule involved in APP processing which macromolecule is presenilin 1 or a fragment of presenilin 1.

[35] In another preferred fifth embodiment the present invention provides a macromolecule involved in APP processing which macromolecule is presenilin 2 or a fragment of presenilin 2.

[36] In a sixth embodiment the present invention provides an inhibitor of beta-amyloid production comprising a compound which interacts with a binding site on a macromolecule involved in the production of beta-amyloid peptide; wherein said binding site is identified by a compound of Formula (I-7T) or (I-43T):

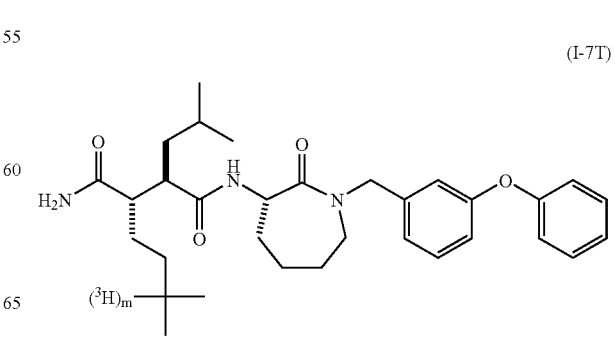

(I-7T)

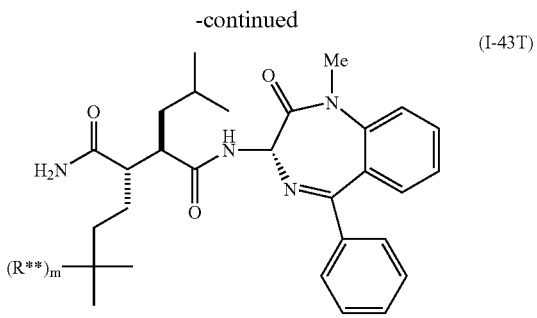

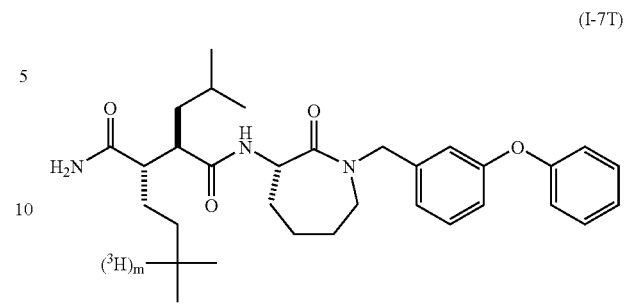

wherein m is about 2.

[36] In the sixth embodiment the binding site is identified as a specific binding site for a compound of Formula (I-7T) or (I-43T), wherein m is about 2.

[37] In a preferred sixth embodiment the macromolecule involved in the production of beta-amyloid peptide is presenilin 1 or a fragment of presenilin 1.

[38] In a preferred sixth embodiment the macromolecule involved in the production of beta-amyloid peptide is presenilin 2 or a fragment of presenilin 2.

[39] In another preferred sixth embodiment the invention provides an inhibitor of beta-amyloid production comprising a compound which interacts with a binding site on a macromolecule involved in the production of beta-amyloid peptide; wherein said binding site is a specific binding site for a compound of Formula (I-7T), wherein m is about 2; and the compound demonstrates a half maximal inhibitory concentration less than 10 micromolar for beta-amyloid production.

[40] In a more preferred sixth embodiment the invention provides an inhibitor of beta-amyloid production comprising a compound which interacts with a binding site on presenilin 1 or a fragment of presenilin 1; wherein said binding site is a specific binding site for a compound of Formula (I-7T), wherein m is about 2; and the compound demonstrates a half maximal inhibitory concentration less than 10 micromolar for beta-amyloid production.

[41] In another preferred sixth embodiment the invention provides an inhibitor of beta-amyloid production comprising a compound which interacts with a binding site on a macromolecule involved in the production of beta-amyloid peptide; wherein said binding site is a specific binding site for a compound of Formula (I-43T), wherein m is about 2; and the compound demonstrates a half maximal inhibitory concentration less than 10 micromolar for beta-amyloid production.

[42] In another more preferred sixth embodiment the invention provides an inhibitor of beta-amyloid production comprising a compound which interacts with a binding site on presenilin 1 or a fragment of presenilin 1; wherein said binding site is a specific binding site for a compound of Formula (I-43T), wherein m is about 2; and the compound demonstrates a half maximal inhibitory concentration less than 10 micromolar for beta-amyloid production.

[43] In a seventh embodiment the present invention provides a tagged inhibitor of beta-amyloid production comprising a tagged compound which interacts with a binding site on a macromolecule involved in the production of beta-amyloid peptide; wherein said binding site is identified by a compound of Formula (I-7T):

wherein m is about 2;

[43] In the seventh embodiment the binding site is identified as a specific binding site for a compound of Formula (I-7T) or (I-43T), wherein m is about 2.

[44] In a preferred seventh embodiment the macromolecule involved in the production of beta-amyloid peptide is presenilin 1 or a fragment of presenilin 1.

[45] In a preferred seventh embodiment the macromolecule involved in the production of beta-amyloid peptide is presenilin 2 or a fragment of presenilin 2.

[46] In another preferred seventh embodiment the invention provides a tagged inhibitor of beta-amyloid production comprising a tagged compound which interacts with a binding site on a macromolecule involved in the production of beta-amyloid peptide; wherein said binding site is a specific binding site for a compound of Formula (I-7T), wherein m is about 2; and the tagged compound demonstrates a half maximal inhibitory concentration less than 10 micromolar for beta-amyloid production.

[47] In a more preferred seventh embodiment the invention provides a tagged inhibitor of beta-amyloid production comprising a tagged compound which interacts with a binding site on presenilin 1 or a fragment of presenilin 1; wherein said binding site is a specific binding site for a compound of Formula (I-7T), wherein m is about 2; and the tagged compound demonstrates a half maximal inhibitory concentration less than 10 micromolar for beta-amyloid production.

[48] In another preferred seventh embodiment the invention provides a tagged inhibitor of beta-amyloid production comprising a tagged compound which interacts with a binding site on a macromolecule involved in the production of beta-amyloid peptide; wherein said binding site is a specific binding site for a compound of Formula (I-43T), wherein m is about 2; and the tagged compound demonstrates a half maximal inhibitory concentration less than 10 micromolar for beta-amyloid production.

[49] In another more preferred seventh embodiment the invention provides a tagged inhibitor of beta-amyloid production comprising a tagged compound which interacts with a binding site on presenilin 1 or a fragment of presenilin 1; wherein said binding site is a specific binding site for a compound of Formula (I-43T), wherein m is about 2; and the tagged compound demonstrates a half maximal inhibitory concentration less than 10 micromolar for beta-amyloid production.

[ ] In yet another preferred embodiment the present invention provides a tagged inhibitor of beta-amyloid production comprising a compound selected from U.S. Pat. No. 5,703,129; PCT application WO98/28268; PCT application WO98/22441; PCT application WO98/22433; PCT application WO98/22430; PCT application WO98/22493; PCT application WO98/22494; PCT application WO98/38177; or PCT application WO95/09838; wherein the compound has been tagged for purposes of the invention.

[ ] In an eighth embodiment the present invention provides a use of a macromolecule or complex of macromolecules involved in APP processing, which a tagged inhibitor of beta-amyloid production binds to specifically, for the identification or assaying of inhibitors as therapeutics for neurological and other disorders involved in APP processing and beta-amyloid production.

[ ] In a preferred eighth embodiment the present invention provides a use of a macromolecule or complex of macromolecules involved in APP processing, which macromolecule or complex of macromolecules is presenilin 1 or a fragment of presenilin 1.

[50] In a more preferred eighth embodiment the present invention provides a method of identifying inhibitors as therapeutics for neurological and other disorders involved in APP processing and beta-amyloid production comprising
  (1) contacting at least one macromolecule involved in APP processing and beta-amyloid production, which macromolecule a tagged inhibitor of beta-amyloid production binds to specifically, with a potential inhibitor of beta-amyloid production; and
  (2) determining the level of inhibition of APP processing and beta-amyloid production.

[51] In an even more preferred eighth embodiment the present invention provides a method wherein the macromolecule is a complex of macromolecules.

[52] In an even more preferred eighth embodiment the present invention provides a method of wherein the macromolecule is presenilin 1 or a fragment of presenilin

[53] In an even more preferred eighth embodiment the present invention provides a method of wherein the macromolecule is presenilin 2 or a fragment of presenilin 2.

[54] In a ninth embodiment the present invention provides a method of treating Alzheimer's disease comprising administering to a host in need of such treatment a therapeutically effective amount of an inhibitor of beta-amyloid production, or a pharmaceutically acceptable salt or prodrug form thereof, wherein said inhibitor of beta-amyloid production binds to a binding site on a macromolecule involved in the production of beta-amyloid peptide and effects a decrease in production of beta-amyloid peptide;

wherein said binding site is a specific binding site for a compound of Formula (I-7T) or (I-43T) wherein m is about 2.

[55] In a preferred ninth embodiment the macromolecule comprises presenilin-1, a fragment of presenilin-1, presenilin-2, or a fragment of presenilin-2.

[56] In another preferred ninth embodiment the binding site is a specific binding site for a compound of Formula (I-43T) wherein m is about 2.

[57] In a more preferred ninth embodiment the macromolecule comprises presenilin-1 or a fragment of presenilin-1.

[58] In another more preferred ninth embodiment the macromolecule comprises presenilin-2 or a fragment of presenilin-2.

[ ] The present invention also provides radiolabeled inhibitors of APP processing and/or the production of beta-amyloid production for use in methods of in vivo diagnostic imaging in the diagnosis of diseases involving APP processing and/or the production of beta-amyloid production. Also provided in the present invention are methods of in vivo diagnostic imaging comprising administering to a subject a diagnostically effective amount of a radiolabeled inhibitor of APP processing and/or the production of beta-amyloid production. As used herein, the term "radiolabeled inhibitors of APP processing" or "radiolabeled inhibitor of beta-amyloid production", when applied to uses for in vivo diagnostic imaging, also includes any ligand that binds to a macromolecule involved in APP processing or beta-amyloid production with an affinity and selectivity suitable for in vivo diagnostic imaging. Thus, such suitable ligand does not need to be an inhibitor of APP processing or beta-amyloid production. Although the radiolabeled ligand may be an inhibitor of beta-amyloid production when administered at therapeutic doses, the relatively low levels of radiolabeled ligand used in an in vivo diagnostic imaging procedure will generally be well below such therapeutic levels. Thus, for purposes of in vivo diagnostic imaging, the term "radiolabeled inhibitor of APP processing" or "radiolabeled inhibitor of beta-amyloid production" refers to any suitable radiolabeled compound which binds in vivo to the same macromolecule target as a compound that is an inhibitor of APP processing and/or beta-amyloid production as described herein.

[59] The present invention includes the above-described method of in vivo diagnostic imaging comprising administering to a subject a diagnostically effective amount of a radiolabeled inhibitor of beta-amyloid production.

[60] The present invention includes the above-described method of in vivo diagnostic imaging wherein said method is used in the diagnosis of a neurological disease which involves APP processing or elevated levels of beta-amyloid, or both.

[61] The present invention includes the above-described method of in vivo diagnostic imaging wherein said method is used in the diagnosis of Alzheimer's disease.

[62] The present invention includes the above-described method of in vivo diagnostic imaging wherein the radiolabeled inhibitor is suitable for imaging of the brain of the subject.

[63] The present invention includes the above-described method of in vivo diagnostic imaging wherein the radiolabeled inhibitor is radiolabeled with one or more radioisotope selected from $^{3}H$, $^{11}C$, $^{14}C$, $^{18}F$, $^{32}P$, $^{35}S$, $^{123}I$, $^{125}I$, $^{131}I$.

[64] The present invention includes the above-described method of in vivo diagnostic imaging wherein the inhibitor of beta-amyloid production is a compound selected from any compound disclosed in or within the scope of compounds disclosed in a reference selected from:
  (1) United States patent U.S. Pat. No. 5,703,129;
  (2) PCT application WO98/22441 (or its priority U.S. Ser. No. 08/755,444);
  (3) PCT application WO98/22433 (or its priority U.S. Ser. No. 08/807,538);
  (4) PCT application WO98/22430 (or its priority U.S. Ser. No. 08/754,895);
  (5) PCT application WO98/22493 (or its priority U.S. Ser. No. 08/755,334);
  (6) PCT application WO98/22494 (or its priorities U.S. Ser. Nos. 08/808,528, 08/807,528 or 08/807,427);
  (7) PCT application WO98/28268 (or its priority U.S. Ser. No. 08/780,025);
  (8) PCT application WO98/38177;
  (9) PCT application WO95/09838;
  (10) PCT application WO99/67221;
  (11) PCT application WO99/67220;
  (12) PCT application WO99/67219;
  (13) PCT application WO95/66934;

(14) PCT application WO00/24392;
(15) Ghosh et al., JACS (2000) 122:3522–2523;
(16) commonly assigned attorney docket number DM-6987, U.S. Ser. No. 09/370,089, filed Aug. 6, 1999;
(17) commonly assigned attorney docket number commonly assigned attorney docket number DM-6987-A, U.S. Ser. No. 09/506,630, filed Feb. 17, 2000;
(18) commonly assigned attorney docket number DM-7076, U.S. Ser. No. 09/469,939, filed Dec. 24, 1999;
(19) commonly assigned attorney docket number PH-7088, filed Feb. 17, 2000;
(20) commonly assigned attorney docket number PH-7131, U.S. Ser. No. 60/158,565, filed Oct. 8, 1999;
(21) commonly assigned attorney docket number PH-7177, U.S. Ser. No. 60/183,186, filed Feb. 17, 2000;
(22) commonly assigned attorney docket number PH-7130-P1, filed Mar. 28, 2000;
(23) commonly assigned attorney docket number PH-7086-P1, filed Mar. 31, 2000;
(24) commonly assigned attorney docket number PH-7164-P1, filed Apr. 11, 2000;
(25) commonly assigned attorney docket number PH-7165-P1, filed Apr. 3, 2000; or
(26) commonly assigned attorney docket number PH-7184-P1, filed Apr. 3, 2000;

or any compound which inhibits beta-amyloid production and binds competitively with any of the foregoing compounds in any of the assays described in the Utility section hereof;

all of which foregoing references are hereby incorporated by reference in their entirety.

[65] The present invention includes the above-described method of in vivo diagnostic imaging wherein the inhibitor of beta-amyloid production exhibits activity as an inhibitor in any of the above-described methods [1]–[15] above.

[66] The present invention includes the above-described method of in vivo diagnostic imaging wherein the inhibitor of beta-amyloid production binds to a macromolecule which is capable of being identified by any of the above-described methods [19]–[27] above.

[67] The present invention includes the above-described method of in vivo diagnostic imaging wherein the inhibitor of beta-amyloid production binds to a macromolecule as described above in [28]–[35] above.

[68] The present invention includes the above-described method of in vivo diagnostic imaging wherein the inhibitor of beta-amyloid production is selected from any of the above-described inhibitors in [36]–[42] above.

[69] The present invention includes the above-described method of in vivo diagnostic imaging wherein the radiolabeled inhibitor of beta-amyloid production is a radiolabeled tagged inhibitor as described above [43]–[509] above.

[70] The present includes the above-described method of in vivo diagnostic imaging wherein the inhibitor of beta-amyloid production is selected from:
(1) an inhibitor of presenilin-1;
(2) an inhibitor of presenilin-2;
(3) an inhibitor of β secretase;
(4) an inhibitor of α secretase;
(5) an inhibitor of γ secretase; or
(6) an inhibitor of BACE/memapsin 2.

[71] The present invention also provides pharmaceutical compositions suitable for in vivo diagnostic imaging comprising a radiolabeled inhibitor of beta-amyloid production. Included in the present invention are the above-described radiolabeled inhibitors of beta-amyloid production, wherein the radiolabel is selected from the group $^{3}$H, $^{11}$C, $^{14}$C, $^{18}$F, $^{32}$P, $^{35}$S, $^{123}$I, $^{125}$I, and $^{131}$I. Included in the present invention is a radiopharmaceutical composition comprising a radiopharmaceutically acceptable carrier and a radiolabeled inhibitor of beta-amyloid production. Included in the present invention is a method of determining levels of proteins involved in beta-amyloid production in a mammal comprising administering to the mammal a radiopharmaceutical composition comprising a radiolabeled inhibitor of beta-amyloid production, and imaging said mammal. Included in the present invention is a method of diagnosing a disorder associated with beta-amyloid production in a mammal comprising administering to the mammal a radiopharmaceutical composition comprising a radiolabeled inhibitor of beta-amyloid production, and imaging said mammal.

[72] The present invention includes the above-described pharmaceutical compositions wherein the composition is used in the diagnosis of a neurological disease which involves APP processing or elevated levels of beta-amyloid, or both.

[73] The present invention includes the above-described pharmaceutical compositions wherein the composition is used in the diagnosis of Alzheimer's disease.

[74] The present invention includes the above-described pharmaceutical compositions wherein the radiolabeled inhibitor is suitable for imaging of the brain of the subject.

[75] The present invention includes the above-described pharmaceutical compositions wherein the radiolabeled inhibitor is radiolabeled with one or more radioisotope selected from $^{3}$H, $^{11}$C, $^{14}$C, $^{18}$F, $^{32}$P, $^{35}$S, $^{123}$I, $^{125}$I, $^{131}$I.

[76] The present invention includes the above-described pharmaceutical compositions wherein the inhibitor of beta-amyloid production is a compound selected from any compound disclosed in or within the scope of compounds disclosed in a reference selected from:
(1) U.S. Pat. No. 5,703,129;
(2) PCT application WO98/22441 (or its priority U.S. Ser. No. 08/755,444);
(3) PCT application WO98/22433 (or its priority U.S. Ser. No. 08/807,538);
(4) PCT application WO98/22430 (or its priority U.S. Ser. No. 08/754,895);
(5) PCT application WO98/22493 (or its priority U.S. Ser. No. 08/755,334);
(6) PCT application WO98/22494 (or its priorities U.S. Ser. Nos. 08/808,528, 08/807,528 or 08/807,427);
(7) PCT application WO98/28268 (or its priority U.S. Ser. No. 08/780,025);
(8) PCT application WO98/38177;
(9) PCT application WO95/09838;
(10) PCT application WO99/67221;
(11) PCT application WO99/67220;
(12) PCT application WO99/67219;
(13) PCT application WO95/66934;
(14) PCT application WO00/24392;
(15) Ghosh et al., JACS (2000) 122:3522–2523;
(16) commonly assigned attorney docket number DM-6987, U.S. Ser. No. 09/370,089, filed Aug. 6, 1999;
(17) commonly assigned attorney docket number commonly assigned attorney docket number DM-6987-A, U.S. Ser. No. 09/506,630, filed Feb. 17, 2000;

(18) commonly assigned attorney docket number DM-7076, U.S. Ser. No. 09/469,939, filed Dec. 24, 1999;

(19) commonly assigned attorney docket number PH-7088, filed Feb. 17, 2000;

(20) commonly assigned attorney docket number PH-7131, U.S. Ser. No. 60/158,565, filed Oct. 8, 1999;

(21) commonly assigned attorney docket number PH-7177, U.S. Ser. No. 60/183,186, filed Feb. 17, 2000;

(22) commonly assigned attorney docket number PH-7130-P1, filed Mar. 28, 2000;

(23) commonly assigned attorney docket number PH-7086-P1, filed Mar. 31, 2000;

(24) commonly assigned attorney docket number PH-7164-P1, filed Apr. 11, 2000;

(25) commonly assigned attorney docket number PH-7165-P1, filed Apr. 3, 2000; or

(26) commonly assigned attorney docket number PH-7184-P1, filed Apr. 3, 2000;

or any compound which inhibits beta-amyloid production and binds competitively with any of the foregoing compounds in any of the assays described in the Utility section hereof;

all of which foregoing references are hereby incorporated by reference in their entirety.

[77] The present includes the above-described pharmaceutical composition wherein the inhibitor of beta-amyloid production is selected from:

(1) an inhibitor of presenilin-1;
(2) an inhibitor of presenilin-2;
(3) an inhibitor of β secretase;
(4) an inhibitor of α secretase;
(5) an inhibitor of γ secretase; or
(6) an inhibitor of BACE/memapsin 2.

Definitions

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No 4,666,829. The 43 amino acid sequence is:

```
1
Asp  Ala  Glu   Phe  Arg  His  Asp  Ser  Gly  Tyr
11
Glu  Val  His   His  Gln  Lys  Leu  Val  Phe  Phe
21
Ala  Glu  Asp   Val  Gly  Ser  Asn  Lys  Gly  Ala
31
Ile  Ile  Gly   Leu  Met  Val  Gly  Gly  Val  Val
41
Ile  Ala  Thr.
```

However, a skilled artisan knows that fragments generated by enzymatic degradation can result in loss of amino acids 1–10 and/or amino acids 39–43. Thus, amino acid sequence 1–43 represents the maximum sequence of amino acids for Aβ peptide.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 41, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^{5b}$) occurs more than one time in any constituent or formula for a compound, its definition at each occurrence is independent of its definition at every other occurrence. Thus, for example, if a group is shown to be substituted with 0–2 $R^{5b}$, then said group may optionally be substituted with up to two $R^{5b}$ groups and $R^{5b}$ at each occurrence is selected independently from the definition of $R^{5b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of. carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl".

As used herein, "alkenyl" or "alkenylene" is intended to include hydrocarbon chains of either a straight or branched configuration and one or more unsaturated carbon-carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms, preferably 1, 2, or 3 heteroatoms, independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyi, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl, pyridinyl or naphthyl. Unless otherwise specified, "aryl" may be unsubstituted or substituted with 0 to 3 groups selected from H, —OH, —OCH$_3$, Cl, F, Br, I, CN, —NO$_2$, —NH$_2$, —N(CH$_3$)H, —N(CH$_3$)$_2$, —CF$_3$, —OCF$_3$, —C(=O)CH₃, —SCH₃, —S(=O)CH₃, —S(=O)₂CH₃, —CH₃, —CH₂CH₃, —CO₂H, and —CO₂CH₃.

The phrase "additional lactam carbons", as used herein, is intended to denote the number of optional carbon atoms in the lactam ring B of Formula (I). Formula (I″):

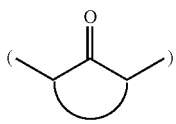

(I″)

represents the lactam ring B of Formula (I). Additional lactam carbons are carbons in lactam ring B other than the carbons numbered 2 and 3 in the backbone of the formula. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. Examples of lactam ring B include:

B1

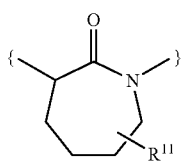

B2

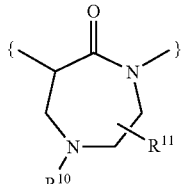

B3

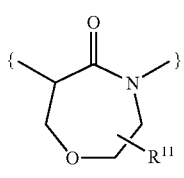

B4

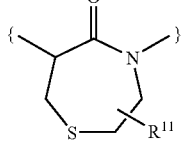

B5

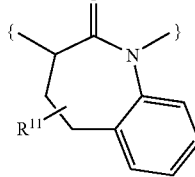

-continued

B6

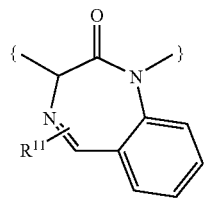

B7

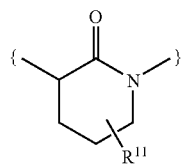

B8

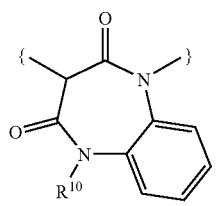

B9

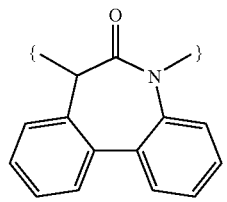

B10

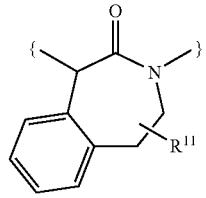

B11

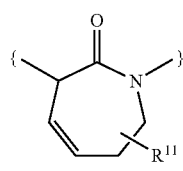

B12

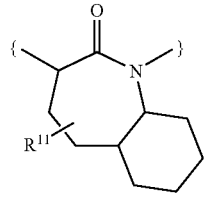

B13

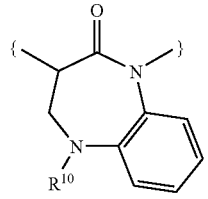

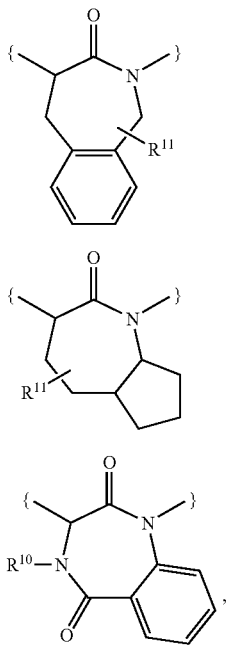

but are not intended to limit the invention. Preferred examples of lactam ring B are B1, B2, B5, B6, B8, B9, B13, and B16; more preferred examples of lactam ring B are B1, B6, B8, B9, and B13. Even more preferred examples of lactam ring B are B1 and B6. Preferred examples of substituent $R^{10}$ or $R^{11}$ on lactam B are methyl, ethyl, phenyl, 4-fluorophenyl, 4-chlorophenyl, 4-trifluorophenyl, (4-fluorophenyl)methyl, (4-chlorophenyl)methyl, and (4-trifluorophenyl)methyl.

As used herein, "macromolecule" or "complex of macromolecules", is intended to mean a cellular component involved directly or indirectly in APP processing and the production of Aβ peptide. By indirectly, its effect on APP processing may be mediated by intervening molecules. An example of a "macromolecule" or "complex of macromolecules" is presenilin 1 or endogenous cleavage N terminal or C terminal fragments of presenilin 1. Additional examples of a "macromolecule" or "complex of macromolecules" is presenilin 2, a homolog of presenilin 1 or a homolog of presenilin 2.

It is envisaged that the scope of "macromolecule" or "complex of macromolecules" involved in APP processing can be found in a wide variety of sources. Sources of a "macromolecule" or "complex of macromolecules" are considered to be materials suspected or known to contain a macromolecule involved in APP processing. Examples of a material suspected or known to contain a macromolecule involved in APP processing include, but are not limited to, purified proteins; suspensions of proteins; cells, tissues or organs, derived from prokaryotes or eucaryotes; and macromolecules derived from recombinant expression systems. Examples of cells include, but are not limited to, HEK293 cells, IMR 32 cells, RAJI cells, CHO cells, U-937 cells, and THP-1 cells; preferably HEK293 or TNP-1 cells. Examples of tissues or organs include, but are not limited to, spleen, brain, and testes. Examples of prokaryotes include, but are not limited to, bacteria, more preferably *E. coli*. Examples of eucaryotes include, but are not limited to, mouse, rat, guinea pig, bovine, porcine, monkey, human, and nematodes (preferably *C. elegans*). An example of a suspension of protein includes, but is not limited to, lipid systems. An example of a macromolecule derived from recombinant expression systems includes, but is not limited to, *C. elegans* knockout of Sel-12 and reintroduction of PS-1. (See Levitan, D. and Greenwald, I., Nature, 377, pp 351–354, 1995.)

It is understood that one skilled in the art can readily determine the scope of the term "binding site" and "specific binding site" as used herein. For further guidance, the tagged compounds of the present invention, for example (I-7T), (I-11T), and (I-43T), bind to a specific site on one or more macromolecules involved directly or indirectly in APP processing and the production of Aβ peptide, and thus effect a decrease in the production of Aβ peptide. One skilled in the art can readily determine whether other compounds, which are inhibitors of beta-amyloid production, bind to a same site as the tagged compounds of the present invention by using the assays disclosed herein. However, it is understood that within the scope of the present disclosure the phrase "is identified by a compound of Formula (I-#)" or "is a specific binding site for a compound of Formula (I-#)" refers to defining the physical site on the macromolecule wherein a compound of Formula (I-#) binds to and not to a molecular reaction of binding. Thus, the phrase "a specific binding site for a compound of Formula (I-#)" does not require the compound of Formula (I-#) to be present.

As used herein, "potential inhibitor of beta-amyloid production" is intended to mean any compound which is being screened for activity to inhibit the production of beta-amyloid peptide, or the proteolytic activity leading to the production of beta-amyloid peptide, using the assay of the invention described herein. It is understood that a "potential inhibitor of beta-amyloid production", which is active in the assay of the invention for inhibiting the production of beta-amyloid peptide, can subsequently be used in the assay of the invention as a "beta-amyloid peptide inhibitor", as defined below, once the compound has been tagged. It is also understood that a "potential inhibitor of beta-amyloid production", which is active in the assay of the invention for inhibiting the production of beta-amyloid peptide, can subsequently be used in pharmaceutical compositions for the treatment of degenerative neurological disorders involving beta-amyloid production, preferably for the treatment of Alzheimer's disease.

As used herein, "beta-amyloid peptide inhibitor" or "inhibitor of beta-amyloid production" is intended to mean any compound which inhibits the production of beta-amyloid peptide, or the proteolytic activity leading to the production of beta-amyloid peptide. Examples of a beta-amyloid peptide inhibitor include, but are not limited to, the scope of compounds of Formula (I), examples of which are disclosed herein. However, it is contemplated for use in the invention that compounds beyond the scope of compounds of Formula (I) may be used in the invention. Additional examples of a beta-amyloid peptide inhibitor, contemplated by the invention, include, but are not limited to, 5-amino-6-cyclohexyl-4-hydroxy-hexanamide derivatives disclosed in United States patent U.S. Pat. No. 5,703,129, issued Dec. 30, 1997; N-aryl amino acid esters and N-heteroaryl amino acid esters disclosed in PCT application WO98/22441 (published May 28, 1998; priority U.S. Ser. No. 08/755,444); N-arylacetyl amino acid amides, N-heteroarylacetyl amino acid amides, and N-alkylacetyl amino acid amides disclosed in PCT application WO98/22433 (published May 28, 1998; priority U.S. Ser. No. 08/807,538); N-arylacetyl amino acid esters N-heteroarylacetyl amino acid esters, and N-alkylacetyl amino acid esters disclosed in PCT application WO98/22430 (published May 28, 1998; priority U.S. Ser. No. 08/754,895); N-aryl amino acid derivatives and N-heteroaryl amino acid derivatives disclosed in PCT application WO98/22493 (published May 28, 1998; priority U.S. Ser. No. 08/755,334); amino acid derivatives disclosed in PCT application WO98/22494 (published May 28, 1998; priority U.S. Ser. Nos. 08/808,528, 08/807,528, 08/807,427); cycloalkyl, lactam, lactone and related compounds disclosed in PCT application WO98/28268 (published Jul. 2, 1998; priority U.S. Ser. No. 08/780,025); all references of which are hereby incorporated by reference in their entirety.

As used herein, "tagged inhibitor of beta-amyloid production", is intended to mean "beta-amyloid peptide inhibitor" compounds which are tagged. By "tagged" or "tagged inhibitor of beta-amyloid production" or "tagged compound", it is meant that the subject beta-amyloid peptide inhibitor compounds contain a tag which is suitable for detection in an assay system or upon administration to a mammal. Suitable tags are known to those skilled in the art and include, for example, radioisotopes, fluoroscent groups, biotin (in conjunction with streptavidin complexation), and photoaffinity groups. As used herein, "radiolabeled compound" or "radiolabeled inhibitor" refers to a tagged inhibitor of beta-amyloid production wherein the tag is a radioisotope.

For purposes of in vivo diagnostic imaging, by "radiolabeled" it is meant that the subject inhibitors of beta-amyloid production contain a radioisotope which is suitable for administration to a mammalian patient. Preferred radioisotopes for in vivo diagnostic imaging by positron emission tomography (PET) are $^{11}$C, $^{18}$F, $^{123}$I, and $^{125}$I.

Suitable radioisotopes are known to those skilled in the art and include, for example, isotopes of halogens (such as chlorine, fluorine, bromine and iodine), and metals including technetium and indium. Preferred radioisotopes include $^3$H, $^{11}$C, $^{14}$C, $^{18}$F, $^{32}$P, $^{35}$S, $^{123}$I, $^{125}$I, $^{131}$I. Radiolabeled compounds of the invention may be prepared using standard radiolabeling procedures well known to those skilled in the art. Suitable synthesis methodology is described in detail below. As discussed below, the beta-amyloid peptide inhibitor compounds of the invention may be radiolabeled either directly (that is, by incorporating the radiolabel directly into the compounds) or indirectly (that is, by incorporating the radiolabel into the compounds through a chelating agent, where the chelating agent has been incorporated into the compounds). Also, the radiolabeling may be isotopic or nonisotopic. With isotopic radiolabeling, one group already present in the compounds of the invention described above is substituted with (exchanged for) the radioisotope. With nonisotopic radiolabeling, the radioisotope is added to the compounds without substituting with (exchanging for) an already existing group. Direct and indirect radiolabeled compounds, as well as isotopic and nonisotopic radiolabeled compounds are included within the phrase "radiolabeled compounds" as used in connection with the present invention. Such radiolabeling should also be reasonably stable, both chemically and metabolically, applying recognized standards in the art. Also, although the compounds of the invention may be labeled in a variety of fashions with a variety of different radioisotopes, as those skilled in the art will recognize, such radiolabeling should be carried out in a manner such that the high binding affinity and specificity of the unlabeled or untagged inhibitor of beta-amyloid production compounds of the invention to the macromolecule involved in APP processing is not significantly affected. By not significantly affected, it is meant that the binding affinity and specificity is not affected more than about 3 log units, preferably not more than about 2 log units, more preferably not more than about 1 log unit, even more preferably not more than about 500%, and still even more preferably not more than about 250%, and most preferably the binding affinity and specificity is not affected at all.

Examples of a tagged inhibitor of beta-amyloid production include, but are not limited to, the scope of compounds of Formula (I), examples of which are disclosed herein. However, it is contemplated that tagged compounds beyond the scope of compounds of Formula (I) may be used in the invention. Additional examples of a tagged inhibitor of beta-amyloid production, contemplated by the invention, include, but are not limited to, beta-amyloid peptide inhibitors disclosed in U.S. Pat. No. 5,703,129, issued Dec. 30, 1997; WO98/22441 (published May 28, 1998); WO98/22433 (published May 28, 1998); WO98/22430 (published May 28, 1998); WO98/22493 (published May 28, 1998); WO98/22494 (published May 28, 1998); and WO98/28268 (published Jul. 2, 1998), which inhibitors can be tagged for use in the invention. Preferred examples of a tagged inhibitor of beta-amyloid production are compounds of Formula (I) and compounds of WO98/28268 (published Jul. 2, 1998) which can be tagged. More preferred are compounds of Formula (I).

For radiolabeled compounds, the label may appear at any position on the beta-amyloid peptide inhibitor. Preferred radiolabeled compounds of the invention are beta-amyloid peptide inhibitor radiolabeled with tritium. More preferred radiolabeled compounds of the invention are radiolabeled compounds wherein the radiolabel is located on $R^3$ of Formula (I).

As used herein, when the tagged inhibitor of beta-amyloid production is tagged with a photoaffinity group or photoaffinity labeled, the term "photoaffinity group" or "photoaffinity labeled" refers to a substituent on the inhibitor which can be activated by photolysis at an appropriate wavelength to undergo a crosslinking photochemical reaction with the macromolecule to which it is associated. An example of a "photoaffinity group" is a benzophenone substituent.

In the present invention it has also been discovered that the radiolabeled compounds above are useful as inhibitors of beta-amyloid peptide production and thus the radiolabeled compounds of the invention may also be employed for therapeutic purposes, in addition to the diagnostic usage described above.

As used herein, "inhibitory concentration" is intended to mean the concentration at which the "potential inhibitor of beta-amyloid production" compound screened in the assay of the invention inhibits a measurable percentage of beta-amyloid peptide production. Examples of "inhibitory concentration" values range from $IC_{50}$ to $IC_{90}$, and are preferably, $IC_{50}$, $IC_{60}$, $IC_{70}$, $IC_{80}$, or $IC_{90}$, which represent 50%, 60%, 70%, 80% and 90% reduction in beta-amyloid peptide production, respectively. More preferably, the "inhibitory concentration" is measured as the $IC_{50}$ value. It is understood that an designation for $IC_{50}$ is the half maximal inhibitory concentration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, benzenesulfonic, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Methods for the synthesis of succinylamino lactams are known in the art and are disclosed in a number of references including PCT publication number WO 96/29313, which is hereby incorporated by reference.

Disubstituted succinate derivatives can be prepared by a number of known procedures. The procedure of Evans (D. A. Evans et al, Org. Synth. 86, p 83 (1990)) is outlined in Scheme 1 where acylation of an oxazolidinone with an acylating agent such as an acid chloride provides structures 1. Alkylation to form 2 followed by cleavage of the chiral auxiliary and subsequent alkylation of the dianion of the carboxylic acid 3 provides a variety of disubstituted succinates which can be separated and incorporated into structures of Formula (I) by those skilled in the art. Additional examples are found in P. Becket, M. J. Crimmin, M. H. Davis, Z. Spavold, Synlett, (1993), 137–138, incorporated herein by reference.

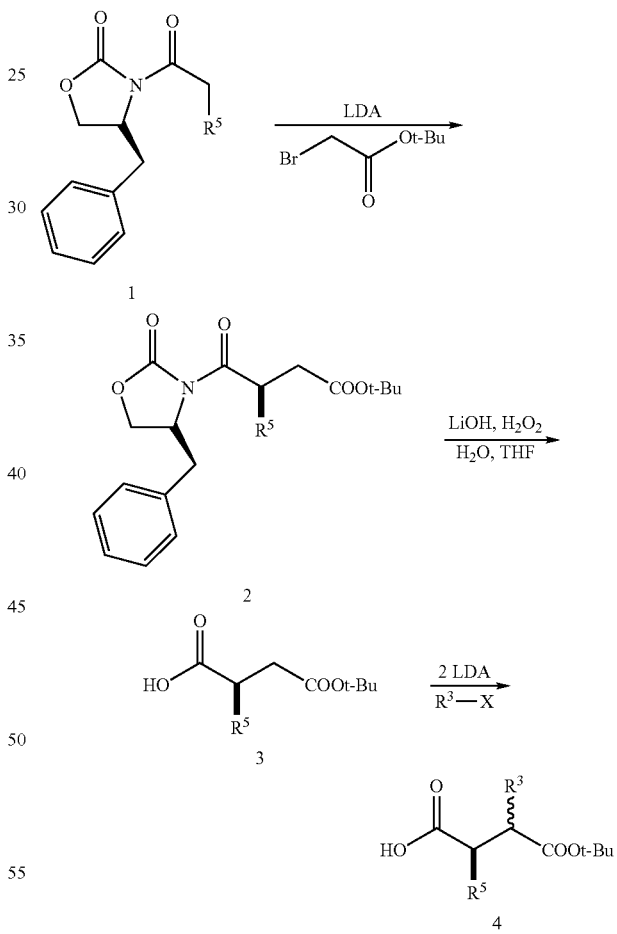

Scheme 1

Diastereomerically pure succinate derivatives can be accessed using the chemistry outlined below, adapted from P. Becket, M. J. Crimmin, M. H. Davis, Z. Spavold, Synlett, (1993), 137–138 incorporated herein by reference. This reference provides the synthesis below to obtain compound 9. Compound 11 is used as an intermediate and is prepared from 9 by hydrogenation of the allyl group followed by coupling of 9-fluorenemethanol under standard conditions using DCC and DMAP in CH$_2$Cl$_2$. Deprotection of the tert-butyl ester is accomplished by treatment with 50% trifluoroacetic acid.

Additional methods useful for the preparation of succinate derivatives are known by those skilled in the art. Such references include, McClure and Axt, Bioorganic & Medicinal Chemistry Letters, 8 (1998) 143–146; Jacobson and Reddy, Tetrahedron Letters, Vol 37, No. 46, 8263–8266 (1996); Pratt et al., SYNLETT, May 1998, p. 531.

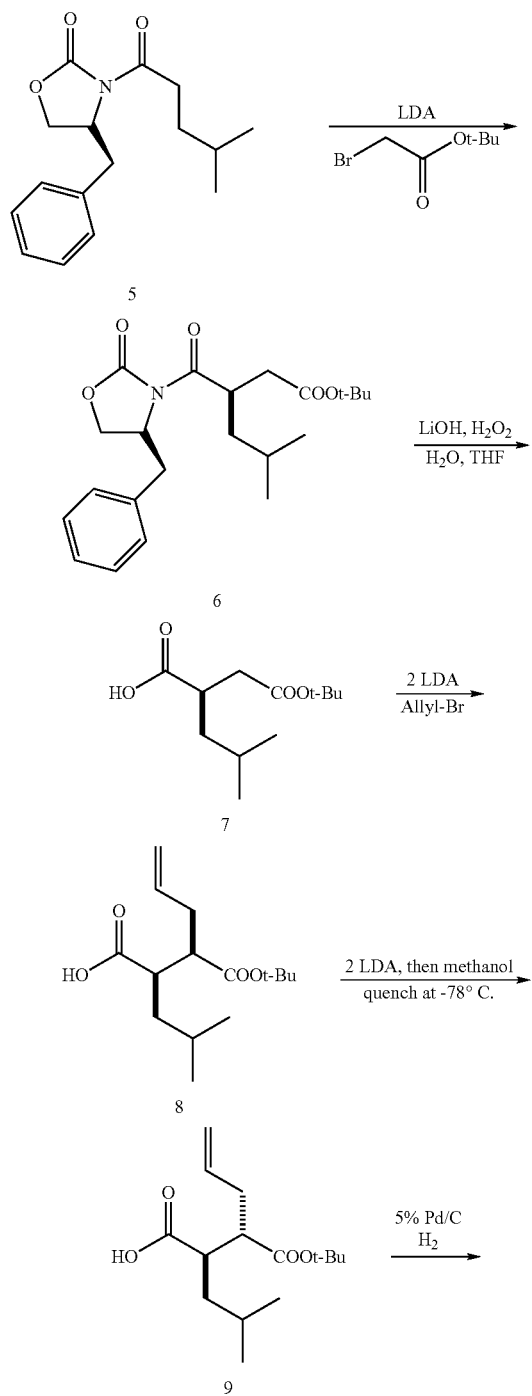

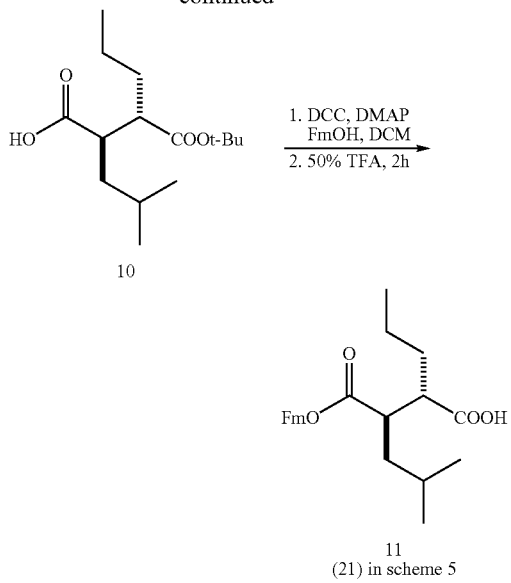

A variety of compounds of Formula (I) can be prepared by methods described in Scheme 4. The protected α-amine 3 of the α-amino-ε-caprolactam can be prepared by methods well known in the literature for amino protecting groups as discussed in Theodora W. Greene's book "Protective Groups in Organic Synthesis", such as N-Boc using di-t-butyldicarbonate in an appropriate solvent like DMSO. A sulfur atom can be introduced into the ring providing L-α-amino-β-thio-ε-caprolactam according to the procedure in S. A. Ahmed et al, FEBS Letters, (1984), vol. 174, pages 76–9 (Scheme 3). One skilled in the art can extend this methodology to the synthesis of β-amino and oxygen containing rings by analogy. The sulfur-containing molecules can also be oxidized to the sulfoxide and sulfone by methods known to one skilled in the art.

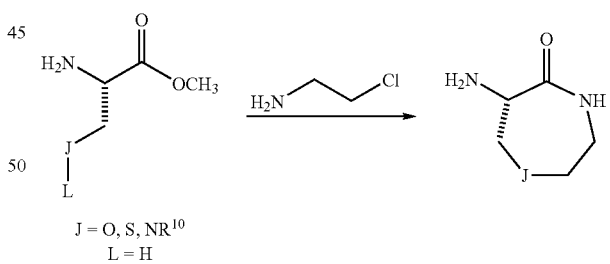

The lactam nitrogen of compound 13 can be alkylated by generating the anion with bases such as LDA, lithium bis(trimethylsilyl)amide or sodium hydride in solvents like THF, with or without cosolvents such as DMPU or HMPA and reacting this with a variety of groups containing leaving groups (X") like bromide, iodide, mesylate or tosylate. Alkylating agents such as a-bromo amides, ketones and acids can be prepared by a number of literature methods including halogenation of amino acids by diazotization or are commercially available. Other suitable alkylating agents such as alkyl, allylic and benzylic halides can be formed form a variety of precursors such as free-radical addition of halides or activation of alcohols, and other chemistries known to those skilled in the art. For discussion of these types of reactions, see Carey, F. A. and Sundberg, R. J., Advanced Organic Chemistry, Part A, New York: Plenum Press, 1990, pages 304–305, 342–347, 695–698.

The N-Boc protecting group can be removed by any number of methods well known in the literature like TFA in methylene chloride to give the compound 15. The amine 15 can be coupled to an appropriately substituted carboxylic acid or acid chloride by methods well described in the literature for making amide bonds, like TBTU in DMF with a base like NMM to give the elaborated compound 16. Compounds 16 can be alkylated using standard bases like LDA, NaH, or NaHMDS to deprotonate the amide followed by addition of an alkylating agent with an appropriate leaving group like halide, mesylate, or triflate in an appropriate solvent to provide compounds 17 with an $R^6$ substituent. The t-butyl ester is then removed by treatment with TFA in methylene chloride to give the carboxylic acid 17.

phosphate) followed by addition of an alcohol and 4-dimethylaminopyridine allows formation of the ester directly. For additional acylation reactions see for example Carey, F. A. and Sundberg, R. J., Advanced Organic Chemistry, Part A, New York: Plenum Press, 1990, pages 475–479.

Additional Examples of compounds of Formula (I) can be prepared as shown in Scheme 5. A suitable resin for solid phase synthesis such as Fmoc (Fluorenylmethylcarbonyl)-protected hydroxylamine bound to polystyrene beads can be purchased from Novabiochem, Inc. Deprotection of the Fmoc group under standard conditions using 20% piperidine in DMF provides trityl-linked hydroxylamine resin. Coupling of a fluorenylmethyl-protected succinic acid derivative such as 20 with a coupling agent such as HATU in a suitable solvent like DMF or N-methylpyrrolidinone provides the support-bound hydroxamate 21. The Fluorenylmethyl ester can be removed using 20% piperidine in DMF to provide the free carboxylic acid which can be coupled to amines like the caprolactam 22 (which is available using chemistry outlined

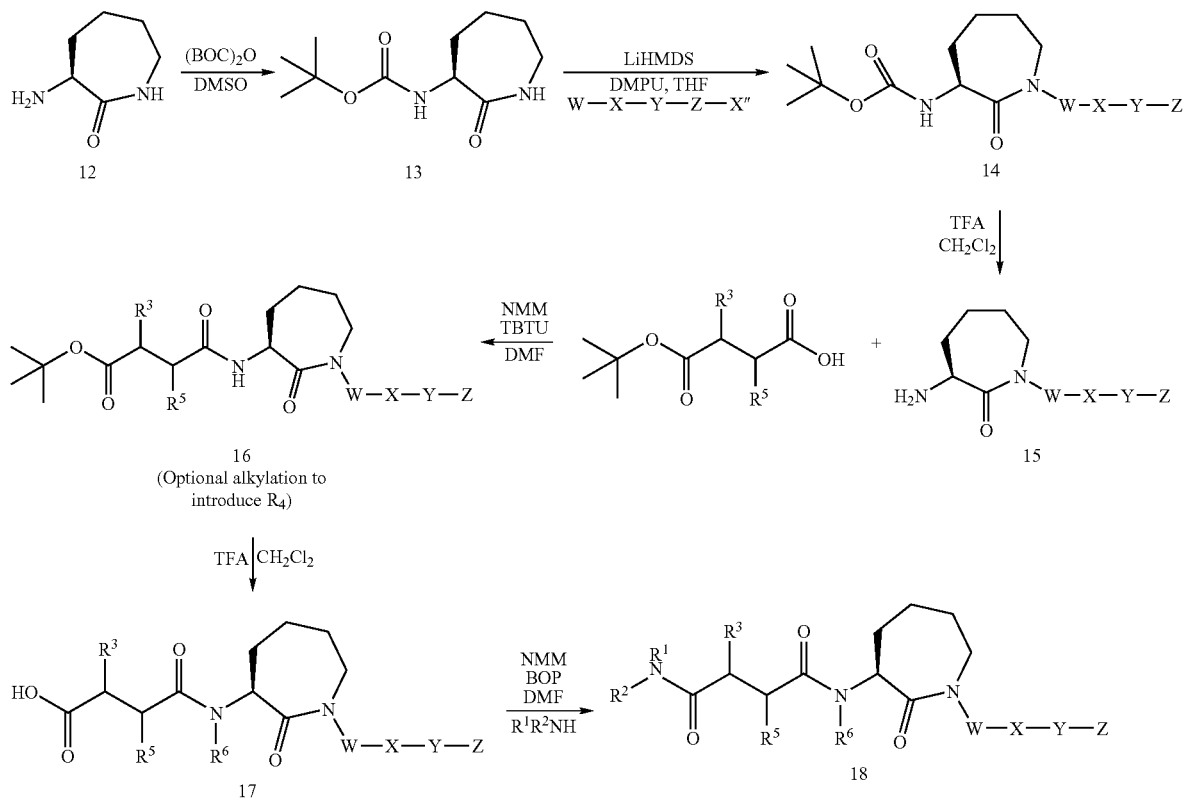

Scheme 4

The final compounds 18 were prepared by treating the activated carboxylic acid of 17 with an appropriately substituted amine. For instance, activation of the carboxylic acid with HATU (O-(7-azabenzotriazol-1-yl)-1,1,3,3,-tetramethyluronium hexafluorophosphate) or PyBOP (benzotriazole-1-yl-oxy-tris-pyrrolidino-phosphonium hexafluorophosphate) or other coupling agents known to those skilled in the art allows condensation with ammonia to form primary amides. Similarly, condensation of the activated acid with hydroxylamine hydrochloride provides the hydroxamic acid, or reaction with a primary or secondary amine provides the substituted amine derivative. Activation of the acid with PyBrOP (bromo-tris-pyrrolidino-phosphonium hexafluoroin Scheme 4) using PyBOP (benzotriazole-1-yl-oxy-tris-pyrrolidino-phosphonium hexafluorophosphate) and a suitable base like DIEA in DMF or NMP. The support-bound intermediate 23 can then be elaborated to biaryl structures of the type 24 using typical Suzuki coupling conditions employing a catalyst such as Palladium complexes like tetrakis(triphenylphosphine)-palladium with 2M aqueous sodium carbonate as a base in a suitable solvent like THF or DME and an excess of a boronic acid. The final compounds are liberated from the support employing dilute (5%) trifluoroacetic acid in $CH_2CL_2$ and purified by conventional chromatography.

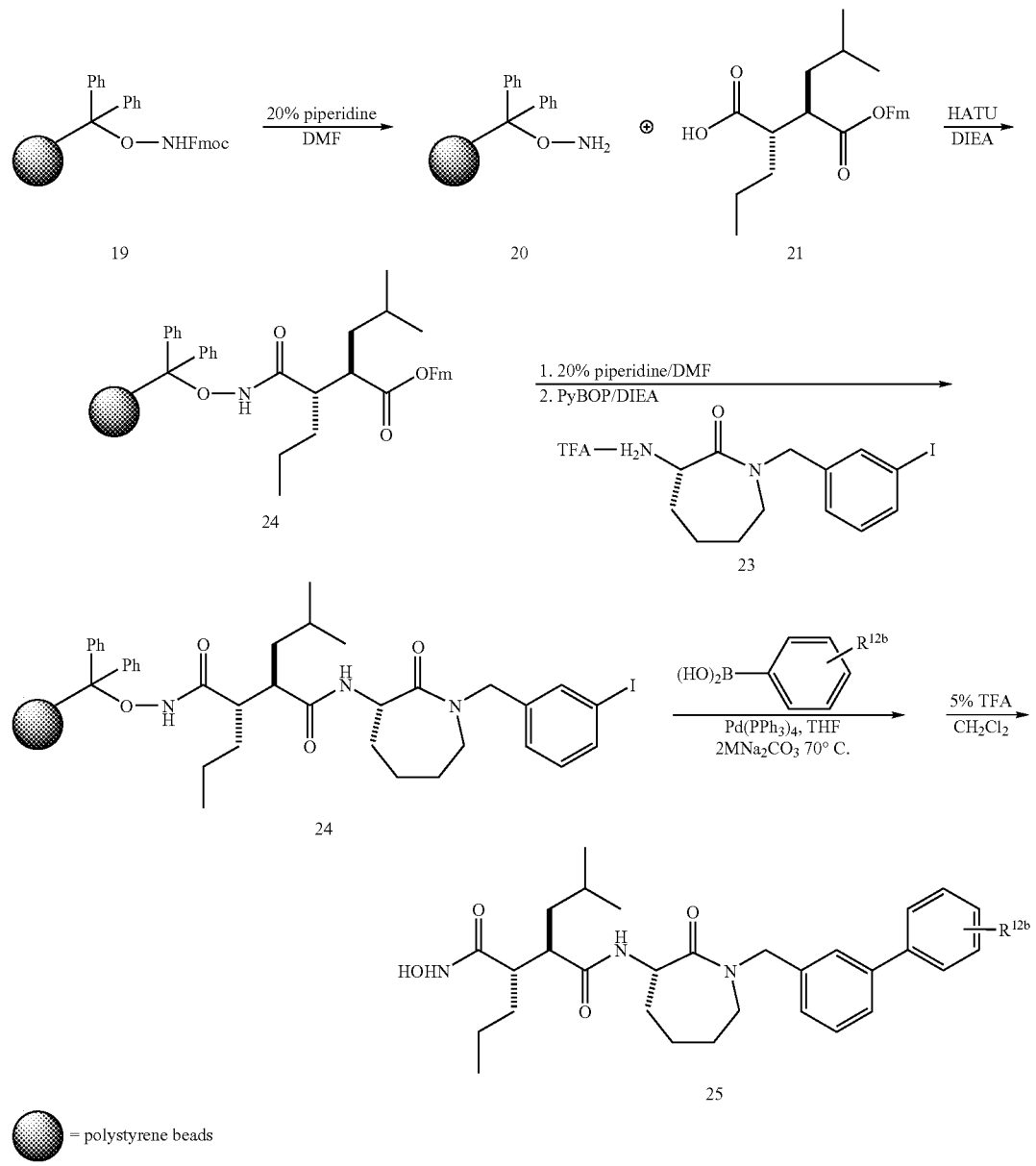

Scheme 5

General procedure for solid-phase synthesis according to Scheme 5.

Resin 20 of Scheme 5: Fmoc-protected resin 19 (2.0 g, 0.78 mmol/g, 1.56 mmol) is purchased from Novabiochem and swelled in 20 ml of $CH_2Cl_2$ for 1 hour. The $CH_2Cl_2$ is removed and the resin is then treated with 25% v/v piperidine in DMF (8 mL) and allowed to shake slowly for 16 h. The solvent was removed by filtration and the resin was shaken with an additional 8 mL of 25% v/v piperidine in DMF for 2 h at rt. The solvents were removed by filtration, and the resin 20 was rinsed 3× with 20 mL of DMF, 3× with 20 mL of methanol, and 3× with 20 mL of $CH_2Cl_2$ and dried in vacuo.

Succinate 10 of Scheme 2: Succinate 9 is prepared according to the literature procedure (P. Becket, M. J. Crimmin, M. H. Davis, Z. Spavold, Synlett, (1993), 137–138). Succinate 9 (17.8 g, 66 mmol) is dissolved in 250 mL of ethyl acetate and placed in a Parr shaker bottle. To the solution is added 890 mg of 5% palladium on carbon, and the bottle is pressurized to 40 psi with hydrogen gas and shaken for 2.5 h at rt. The hydrogen is removed and the palladium catalyst is removed by filtration through a pad of celite. Concentration of the ethyl acetate solution provides 17.5 g (98%) of succinate 10. No further purification is necessary. MS $(M-H)^+=271$.

Succinate 21 of Scheme 5: Succinate 10 (6.3 g, 23.1 mmol) is dissolved in 125 mL of $CH_2Cl_2$ and 4.8 g (23.3 mmol) of dicyclohexylcarbodiimide is added. The solution is stirred at rt for 30 min and then 4.6 g (23.4 mmol) of 9-fluorenemethanol is added followed by 122 mg (1 mmol)

of 4-dimethylaminopyridine. After 5 h of stirring at rt, the reaction solution was diluted with an additional 100 mL of CH$_2$Cl$_2$ and filtered through a pad of celite to remove precipitated dicyclohexylurea. The solution was then washed 3× with 50 mL of a 1N HCl solution, 3× with 50 mL of a saturated sodium bicarbonate solution, and 2× with 50 mL of brine. The crude product was dried over MgSO$_4$ and soncentrated onto 15 g of silica gel. Chromatography eluting with a gradient of 2.5% to 5% ethyl acetate/hexanes provided 6.4 g (61%) of the diester as an oil. The purified diester (6.4 g 14.2 mmol) is then dissolved in 25 mL of CH$_2$Cl$_2$, 25 mL of trifluoroacetic acid is added, and the reaction solution is stirred at rt for 2 h. The reaction solution is directly concentrated in vacuo to an oil which is then redissolved in 25 mL of toluene and reconcentrated, followed by drying in vacuo to provide 6.3 g (98%) of the desired succinate 9 as an oil which solidifies on standing. MS (M+Na)$^+$=471, (M+2Na)$^+$=439.

Caprolactam 23 of Scheme 5: Boc-caprolactam 14 (5.0 g, 21.9 mmol) is dissolved in 60 mL of THF and chilled to −78° C. To the chilled solution is added 24 mL of a 1.0 M solution of lithium bis(trimethylsilyl)amide in THF, and the solution was brought to 0° C. and stirred for 15 min. To the anion solution was added 6.5 g (22 mmol) of 3-iodobenzyl bromide (Aldrich) and the the solution was allowed to warm to rt and stirred for 18 h. The reaction solution was diluted with 50 mL of water and extracted 3× with ethyl acetate. The combined organic layers were dried over MgSO$_4$ and concentrated in vacuo. The crude product was purified by chromatography eluting with a gradient of 5–20% ethyl acetate/hexanes to afford 7.0 g (72%) of the title compound as a white solid. MS (M+Na)$^+$=467.

Resin 22 of Scheme 5: Resin 22 (2.0 g, 0.78 mmol/g, 1.56 mmol) was swollen in 3 mL of DMF. In a separate flask, 1.85 g (4.68 mmol) of succinate 21 was dissolved in 3 mL of DMF and 2.5 mL of N,N-diisopropylethylamine (14 mmol) wsa added, followed by 1.81 g (4.68 mmol) of HATU. The solution containing the active ester was added to the slurried resin and the reaction suspension was slowly shaken for 18 h. The resin was then washed 3× with 20 mL of DMF, 3× with 20 mL of methanol, and 3× with 20 mL of CH$_2$Cl$_2$. Loading of the resin was determined by Fmoc quantitation to be 0.25 mmol/g, see Reddy, M. P.; Voelker, P. J. Int. J. Pept. Protein Res. 1998, 31, 345–348.

Resin 24 of Scheme 5: Resin 22 (2.0 g, 0.25 mmol/g, 0.5 mmol) was suspended in 10 mL of 25% piperidine in DMF. The suspended resin was shaken for 30 min at rt, and then the resin was washed 3× with 20 mL of DMF, 3× with 20 mL of methanol, and 3× with 20 mL of CH$_2$Cl$_2$. Deprotected resin (1.0 g, 0.25 mmol) was swollen in 2 mL of DMF. To the slurry was added 650 mg (1.25 mmol) of PyBOP and 217 mL (1.25 mmol) of DIEA. Separately, 443 mg (0.97 mmol) of caprolactam 23 was dissolved in 2 mL of DMF and 436 mL (2.5 mmol) of DIEA was added. The caprolactam solution was added to the resin slurry and the resin was mixed for 18 h at rt. The solvents were then removed and the coupling was repeated, with shaking at rt for 6 h. The resin was then washed 3× with 10 mL of DMF, 3× with 10 mL of methanol, and 3× with 10 mL of CH$_2$Cl$_2$.

Products 25 of Scheme 5: A 70 mg (17.5 mmol) portion of resin 24 was suspended in 1 mL of THF in a screw-cap vial. To the slurry was added a boronic acid (0.15 mmol), 150 mL of a 2 M solution of sodium carbonate, and 15 mg (13 mmol) of tetrakis(triphenylphosphine)palladium. The vial was tightly closed and heated to 60° C. for 16 h using a dry heater on a shaker table. The solvents were then removed by filtration and the resin was washed 3× with THF (2 mL), 3× with methanol (2 mL), 3× with water, and 3× with CH$_2$Cl$_2$. The resins were then placed in a glass vial and cleaved with 1 mL of 5% trifluoroacetic acid in CH$_2$Cl$_2$ for 30 min. The solution ws filtered off and the resin was washed with an additional 2 mL of CH$_2$Cl$_2$ and the combined filtrates were evaporated to dryness to yield the crude products 25. The products were purified by chromatography eluting with 10–100% ethyl acetate in hexanes to yield 13.0 to 6.0 mg (14–60%) of the final products.

Additional Examples of compounds of Formula (I) can be prepared as shown in Scheme 6. A suitable resin for solid phase synthesis such as Fmoc (Fluorenylmethylcarbonyl)-protected peptide amide linker (PAL)-derivatized polystyrene beads can be purchased from Perkin Elmer Biosystems, Inc. Deprotection of the Fmoc group under standard conditions using 20% piperidine in DMF provides the free benzylamine. Coupling of a succinic acid derivative such as 28 (which is available using chemistry outlined in Scheme 4) with a coupling agent such as HATU in a suitable solvent like DMF or N-methylpyrrolidinone provides the support-bound amide 29. The support-bound intermediate 29 can then be elaborated to biaryl structures of the type 24 using typical Suzuki coupling conditions employing a catalyst such as Palladium complexes like tetrakis(triphenylphosphine)-palladium with 2M aqueous sodium carbonate as a base in a suitable solvent like THF or DME and an excess of a boronic acid. The final compounds are liberated from the support employing 50% trifluoroacetic acid in CH$_2$Cl$_2$ and can be purified by conventional chromatography or preparative HPLC.

Scheme 6

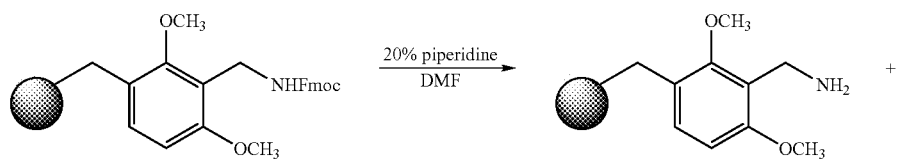

"PAL" resin
26

27

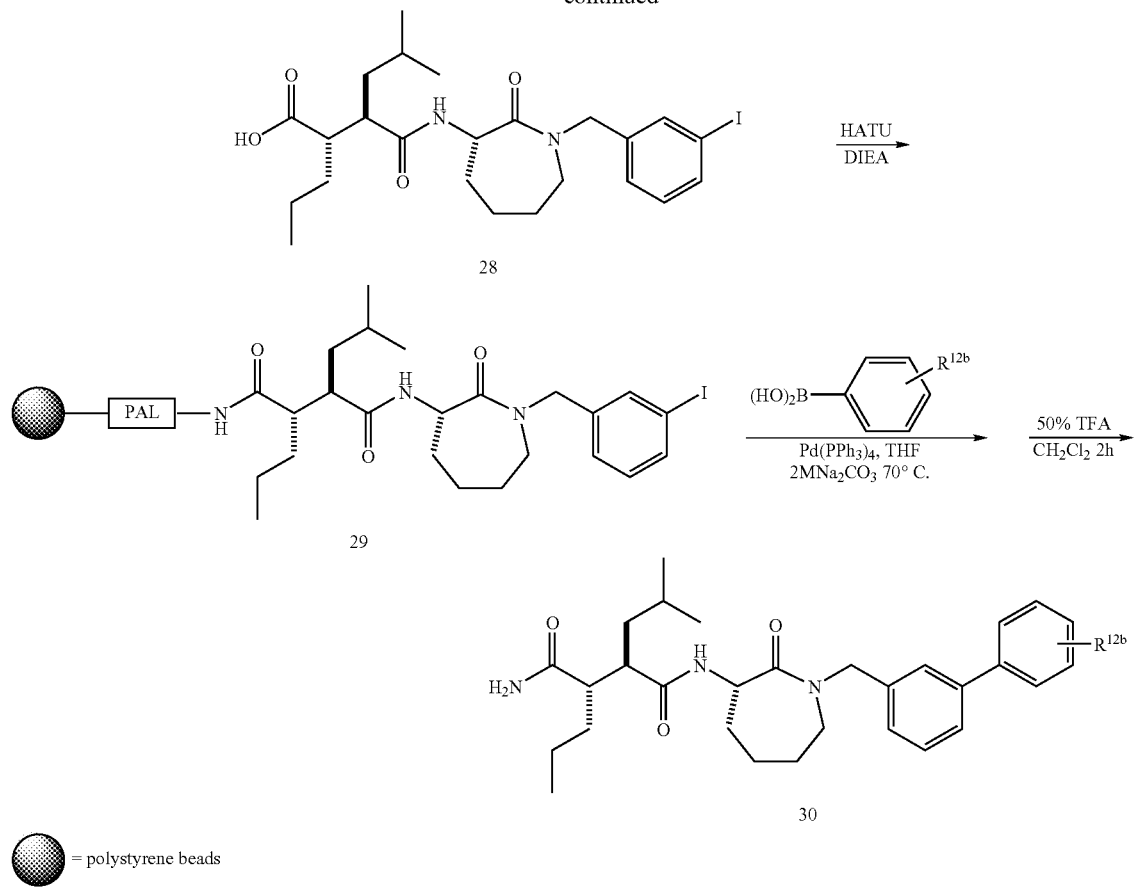

General Procedure for Solid-Phase Synthesis According to Scheme 6

Resin 27 of Scheme 6: Fmoc-protected PAL resin 26 (0.80 g, 0.50 mmol/g, 0.40 mmol) is purchased from Advanced Chemtech and swelled in 20 ml of $CH_2Cl_2$ for 1 hour. The $CH_2Cl_2$ is removed and the resin is then treated with 25% v/v piperidine in DMF (6 mL) and allowed to shake slowly for 1 h. The solvents were removed by filtration, and the resin 27 was rinsed 3× with 20 mL of DMF, 3× with 20 mL of methanol, and 3× with 20 mL of $CH_2Cl_2$ and dried in vacuo.

Acid 28 of Scheme 6: To a solution of 0.100 g (367 mmol) of succinate 10 dissolved in 2.0 mL of dry DMF was added 0.120 mL (1.10 mmol) of N-methylmorpholine. A second solution containing 0.139 g (0.403 mmol) of caprolactam 23 of Scheme 5 dissolved in 2.0 mL of DMF was then added. To the mixed solution was added 229 mg (0.440 mmol) of PyBop and the reaction solution was stirred for 16 h at rt. The reaction solution was diluted with water (20 mL) and extracted 3× with 100 mL of ethyl acetate. The combined organic layers were dried with $Na_2SO_4$ and concentrated under reduced pressure. The resulting oil was purified by chromatography eluting with a gradient of 5–20% ethyl acetate in hexanes to provide 0.195 g (0.360 mmol, 98%) of the tert-butyl ester of Acid 28 (MS M+Na=621). The purified ester (0.195 g, 0.360 mmol) was dissolved in 10 mL of 25% trifluoroacetic acid in $CH_2Cl_2$ and stirred for 2 h at rt. The solvents were removed under reduced pressure and the acid was redissolved in 5 mL of toluene and reconcentrated 2× to remove residual TFA. The crude acid was found to be pure by $^1H$ NMR and was used in Scheme 6 without further purification.

Resin 29 of Scheme 6. Resin 27 (800 mg, 0.40 mmol) was solvated in 4.0 mL of dry DMF and and 0.63 mL (3.6 mmol) of diisopropylethylamine was added followed by a solution of Acid 28 dissolved in 4 mL of DMF. To the slurry was then added 0.465 g (1.2 mmol) of HATU and the slurry was shaken for 26 h at rt. The solvents were removed by filtration, and the resin 29 was rinsed 3× with 20 mL of DMF, 3× with 20 mL of methanol, and 3× with 20 mL of $CH_2Cl_2$. and dried in vacuo.

Products 30 of Scheme 6: A 75 mg (0.38 mmol/g, 28.8 μmol) portion of resin 24 was suspended in 1 mL of THF in a screw-cap vial. To the slurry was added a boronic acid (0.33 mmol), 150 mL of a 2 M solution of sodium carbonate, and 15 mg (13 mmol) of tetrakis(triphenylphosphine)palladium. The vial was tightly closed and heated to 60° C. for 16 h using a dry heater on a shaker table. The solvents were then removed by filtration and the resin was washed 3× with THF (2 mL), 3× with methanol (2 mL), 3× with water, and 3× with $CH_2Cl_2$. The resins were then placed in a glass vial and cleaved with 1 mL of 5% trifluoroacetic acid in $CH_2C_{12}$ for 2 h. The solution was filtered off and the resin was washed with an additional 2 mL of $CH_2Cl_2$ and the combined filtrates were evaporated to dryness to yield the crude products 25. The products were purified by chromatography eluting with 10–100% ethyl acetate in hexanes to yield 0.5 to 2.0 mg (14–60%) of the final products.

The internal phenyl ring can be exchanged for a pyridine ring using chemistry outlined in Scheme 7. The chloromethyl pyidine 33 is prepared using a known procedure reported in Nutaitis, Charles F.; Ledeboer, Mark W. Org. Prep. Proced. Int. (1992), 24(2), 143–6 Incorporated herein by reference. After freebasing the pyridine, alkylation with the Boc-caprolactam provides pyridine intermediate 34, which can be elaborated to the protected amide 35 with succinate 10. Substitution can then be introduced using Suzuki methodology employing a palladium source such as tetrakis(triphenylphosphine) palladium(0) or bis(diphenylphosphinoferrocene) palladium(II) dichloride and a suitable base such as sodium carbonate or triethylamine in a solvent such as THF or toluene containing 10% methanol. Stille chemistry is also possible using a suitable palladium source such as tetrakis(triphenylphosphine)palladium(0) and an aryl or vinyl tin derivative in a solvent such as benzene, toluene, or xylenes. The tert-butyl ester is then deprotected under standard acidic conditions using trifluoroacetic acid and the amide is formed under standard conditions to provide products 36.

General Procedure for Synthesis According to Scheme 7

The chloromethyl pyidine HCl salt 33 is prepared using a known procedure reported in Nutaitis, Charles F.; Ledeboer, Mark W. Org. Prep. Proced. Int. (1992), 24(2), 143–6.

Caprolactam 34: Pyridine HCl salt 33 (2.0 g, 8.3 mmol) is dissolved in 50 mL of a saturated NaHCO₃ solution and the solution is extracted with 30 mL of CH₂Cl₂ 3× followed by concentration of the organic layers to provide the free base. Separately, 1.8 g (7.8 mmol) of caprolactam 13 is dissolved in 40 mL of dry THF and chilled to −78° C. To the solution was added 8.7 mL of a 1M solution of sodium bis(trimethylsilyl) amide. The solution was brought to 0° C. and stirred for 30 min. To the resultant anion was added a solution of 1.7 g (8.3 mmol) of pyridine 33 free base dissolved in 40 mL of THF. The resulting reaction solution was stirred at rt for 18 h and then heated to 50° C. and stirred an additional 3 h. The reaction solution was allowed to cool and then 50 mL of water was added and the aqueous layer was extracted 2× with 100 mL of ethyl acteate. The combined organic layers were dried and concentrated under reduced pressure to provide the crude product which was

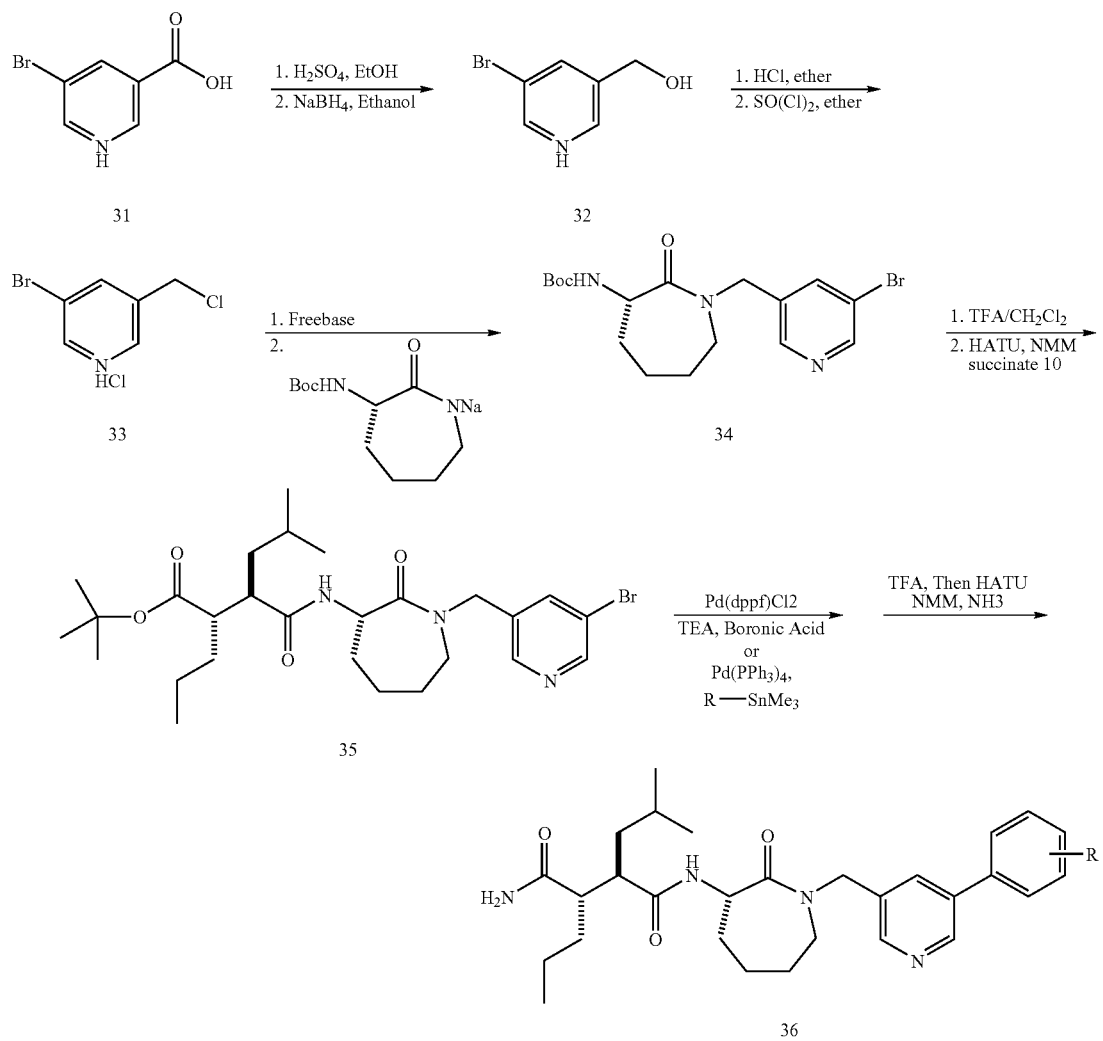

Scheme 7 purified by chromatography eluting with 20 to 100% ethyl acetate in hexanes to provide 1.5 g (51%) of caprolactam 34 as an oil.

Amide 35: Caprolactam 34 (0.40 g, 1.0 mmol) is dissolved in 20 mL of 50% trifluoroacetic acid in CH₂Cl₂ and stirred at rt for 30 min. The solvents were then removed under reduced pressure and the resulting oil was redissolved in 5 mL of toluene and reconcentrated to remove residual TFA. Separately, 0.270 g (1.0 mmol) of succinate 10 was dissolved in 5.0 mL of dry DMF and 0.44 mL (4 mmol) of N-methylmorpholine was added followed by 0.50 g (1.3 mmol) of HATU and the resulting solution was stirred at rt for 30 min. The crude deprotected caprolactam from above was dissolved in 5.0 mL of dry DMF and added to the succinate solution and the resulting solution was heated to 50° C. and stirred for 2 days. The solution was then diluted with 20 mL of water and extracted with 3 50 mL portions of ethyl acetate. The combined organic layers were dried and concentrated under reduced pressure to provide an oil which was purified by chromatography eluting with 20 to 50% ethyl acetate in hexanes to provide 0.40 g (70%) of the Amide 35.

The compounds of Formula (I) of the present invention can also be prepared from aminolactam 42 and succinic acid derivatives 41 using amide bond syntheses known in the art, including methods commonly used in peptide syntheses, such as HATU, TBTU, BOP, pyBOP, EDC, CDI, DCC, hydroxysuccinimide, mixed carboxylic anhydride, and phenyl ester mediated couplings, as illustrated in Scheme 9 for the synthesis of aminolactam 43, an embodiment of the present invention.

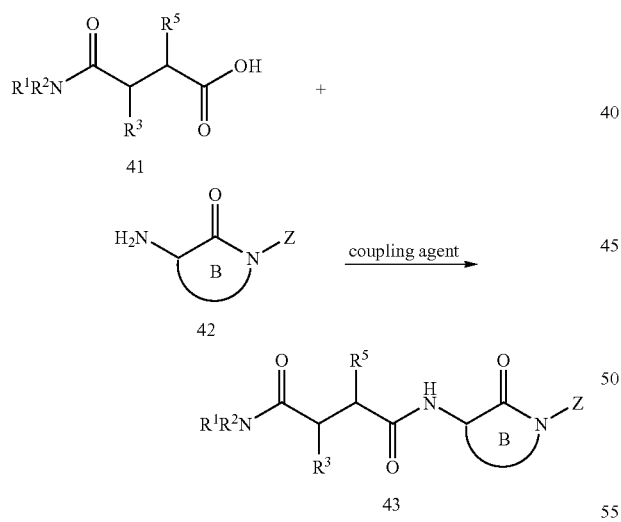

Depending on the structure of the final product, it is appreciated by those skilled in the art that protecting groups or precursor functionality convertable to the desired groups may be desireable. Protecting groups and their use in synthesis are described in Green and Wuts, Protective Groups in Organic Synthesis, (Wiley 1991). The use of protecting groups is further illustrated in Scheme 10, in which the succinate half-ester 44 (Becket et al., Synlett 1993, 137–138) is coupled to the aminobenzodiazepine 45 (Sherrill and Sugg, J. Org. Chem. 1995, 60, 730–734; Bock et al., J. Med. Chem., 1993, 36, 4276–4292) to give ester 46, followed by conversion of the ester group to the primary amide 47.

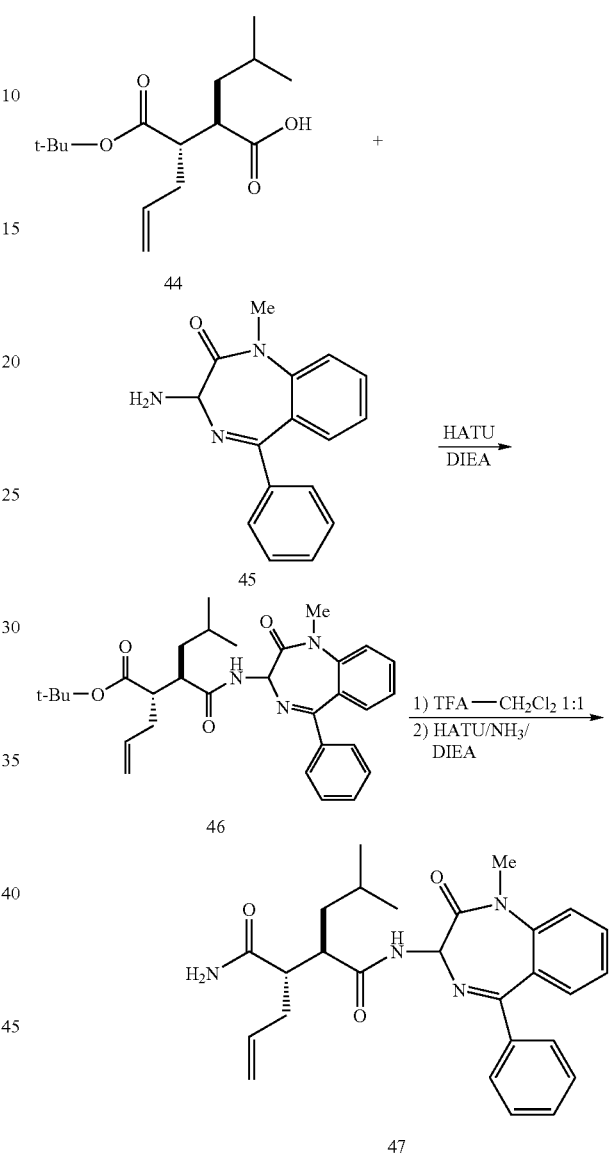

Methods for the synthesis of lactams as contemplated by the present invention in lactam ring B in Formula (I), including amino benzodiazepines, are known in the art and are disclosed in a number of references including PCT publication number WO 98/28268, which is hereby incorporated by reference. Additional references include Bock, et al, J. Org. Chem., 1987, 52, 3232–3239 and Sherrill et al, J. Org. Chem., 1995, 60, 730–734; Walsh, D. A., Synthesis, September 1980, p. 677.

EXAMPLES

Chemical abbreviations used in the Examples are defined as follows: "DMPU" for 1,3-dimethyl-3,4,5,6-tetrahydro-2(1H)-pyrimidone, "TBTU" for O-(1H-benzotriazol-1-yl)-N,N,N',N'-tetramethyluronium tetrafluoroborate, and "BOP"

for benzotriazol-1-yloxytris-(dimethylamino)phosphonium hexafluorophosphate. It is understood that one skilled in the art can discern compounds used in the synthesis of Examples of the invention may be referred to by structure and number. For example, Resin 20 refers to the resin of structure 20 in Scheme 5; succinate 9 refers to the structure 9 found in Scheme 2 which is a succinate compound.

"HPLC" is an abbreviation used herein for high pressure liquid chromatography. Reverse-phase HPLC was carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid).

Example 1

(2R,3S) N1-[(3S)-hexahydro-1-(3,3-diphenylpropyl)-2-oxo-1H-azepin-3-yl]-N4-(hydroxy)-2-(2-methylpropyl)-3-(propyl)-butanediamide

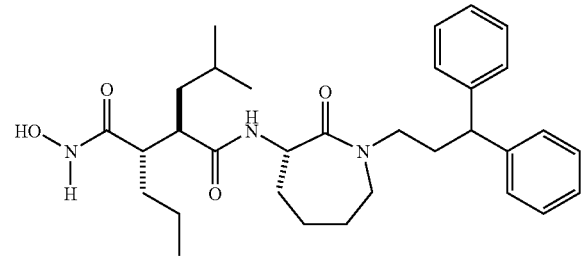

Step (1a): Di-tert-butyldicarbonate (10.2 g, 46.7 mmoles) was added portion wise to a solution of L-(−)-α-amino-ε-caprolactam (5.0 g, 39.0 mmoles) in dimethyl sulfoxide (30 mL). After 5 h at rt, the reaction was partitioned between water (100 mL) and ethyl acetate. The combined organic extracts were washed successively with 1 M HCl (50 mL), brine, and dried (MgSO$_4$) and concentrated in vacuo. The residue was recrystallized in 1:1 v/v ether-hexanes, two crops yielded the desired product (6.26 g, 70%) as white solid. MS (M+H−BOC)$^+$=129.

Step (1b): Triphenylphosphine (3.0 g, 11.4 mmoles) and carbon tetrabromide (3.75 g, 11.7 mmoles) were added successively to a cooled (0° C.) solution of 3,3-biphenyl-1-propanol (1.5 mL, 7.5 mmoles) in dichloromethane (20 mL). After 1.5 hours at rt, the mixture was concentrated in vacuo. The residue was purified by flash chromatography on silica gel (hexanes) to give the desired product (1.93 g, 93% yield) as a clear oil. MS (M−BrC$_2$H$_4$)$^+$=167

Step (1c): A 1.0 M tetrahydrofuran solution of lithium bis(trimethylsilyl)amide (1.3 mL) was added over 15 minutes to compound of Step (1a) (0.29 g, 1.27 mmoles) in tetrahydrofuran (3 mL) and DMPU (2 mL) at −78° C. The iodo compound prepared from compound (1b) (0.85 g, 3.09 mmoles) by typical Finkelstein methodology, in tetrahydrofuran (4 mL) was added and the reaction was allowed to warm to rt slowly. This was stirred for 10 hours at ambient temperature, partitioned between water and ethyl acetate. The combined organic extracts were washed successively with water (20 mL), brine (20 mL), and dried (MgSO$_4$) and concentrated in vacuo. The resulting residue was purified by silica gel column (ethyl acetate:hexanes, 5:95 then ethyl acetate:hexanes, 15:85) to give the desired product (0.16 g, 30%). MS (M−Ot−Bu)$^+$=349.

Step (1d): Trifluoroacetic acid (3 mL) was added to a solution of compound of Step (1c) (0.16 mg, 0.38 mmoles) in dichloromethane (9 mL). After 2 h at rt, the solvent was removed in vacuo. The residual trifluoroacetic acid was removed by azeotrope with dichloromethane (50 mL), toluene (50 mL), and dichloromethane (50 mL) successively to give the desired product (0.17 g, 99%) as a yellow oil. MS (M+H)$^+$=323.

Step (1e): 4-Methylmorpholine (0.6 mL, 5.46 mmoles) and TBTU (0.11 g, 0.34 mmoles) were added to a solution of succinate acid (P. Becket, M. J. Crimmin, M. H. Davis, Z. Spavold, Synlett, (1993), 137–138) (0.085 g, 0.31 mmoles) in N,N-dimethylformamide (3 mL). After 30 minutes at rt, the compound from step (1d) (0.17 g, 0.39 mmoles) was added to the mixture. The reaction was stirred for 16 h at rt, then partitioned between 1 M HCl (20 mL) and ethyl acetate. The combined organic extracts were washed successively with saturated aqueous sodium bicarbonate (20 mL), water (20 mL), brine (20 mL), dried (MgSO$_4$) and concentrated in vacuo. The residue was purified by silica gel chromatography (ethyl acetate:hexanes, 7:93 gradient to ethyl acetate:hexanes 25:75) to give the desired product (120 mg, 67%) as a clear oil. MS (M+NH$_4$−Ot−Bu)$^+$=521.

Step (1f): Trifluoroacetic acid (3 mL) was added to a solution of compound of Step (1e) (120 mg, 0.21 mmoles) in dichloromethane (9 mL). After 3 hours at rt, the mixture was concentrated in vacuo. The residual trifluoroacetic acid was removed by azeotrope with toluene (1×50 mL) and dichloromethane (1×50 mL). The residue was triturated with Et$_2$O:Hexanes 95:5, to give the desired product (75 mg, 70%) as a white solid. MS (M−H)$^−$=519.

Step (1g): 4-Methylmorpholine (0.05 mL, 0.45 mmoles) and BOP (73 mg, 0.17 mmoles) were added to a solution of compound of Step (1f) (60 mg, 0.12 mmoles) in N,N-dimethylformamide (2 mL). Hydroxylamine (33 mg, 0.47 mmoles) was added to the mixture, the reaction was stirred for 16 h at rt, was concentrated in vacuo, was acidified with trifluoroacetic acid, then purified by reverse phase HPLC on a Vydac C-18 column, to give the desired hydroxamic acid as a white solid (45 mg, 75%). MS (M−H)$^−$=534.

Example 2

(2R,3S) N1-[(3S)-hexahydro-1-(3-phenoxybenzyl)-2-oxo-1H-azepin-3-yl]-N4-(hydroxy)-2-(2-methylpropyl)-3-(propyl)-butanediamide

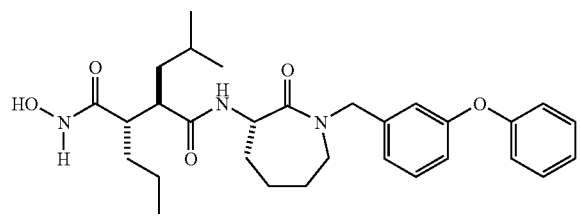

Step (2a): Triphenylphosphine (3.40 g, 13.0 mmoles) and carbontetrabromide (4.20 g, 13.0 mmoles) were added successively to a solution of m-phenoxybenzyl alcohol (1.5 mL, 8.6 mmoles). After 4 h at rt the mixture was concentrated and was purified by silica gel column (hexanes, then ethyl acetate:hexanes, 5:95) to give the desired bromide (1.3 g, 57%) as a yellow oil. MS (M−Br)$^+$=183.

Step (2b): A 1 M solution of lithium bis(trimethylsilyl)amide was added dropwise to a solution of compound of Step (1a) (0.3 g, 1.31 mmoles) in tetrahydrofuran (5 mL) at −78° C. After 30 minutes a solution of compound of Step (2a) (0.43 g, 1.63 mmoles) in tetrahydrofuran (4 mL) was added to the mixture dropwise. The reaction was allowed to come to ambient temperature, stirred for 16 h, then partitioned between water and ethyl acetate. The combined organic extracts were washed successively with water (20 mL), brine (20 mL), dried (MgSO$_4$) and concentrated in vacuo. The crude residue was purified by silica gel chromatography (ethyl acetate:hexanes, 5:95 then ethyl acetate:hexanes, 15:85) to give the desired product (360 mg, 67%) as a clear oil. MS (M−Ot−Bu)$^+$=337.

Step (2c): Trifluoroacetic acid (5 mL) was added to a solution of compound of Step (2b) in dichloromethane (15 mL). After 3 h at rt the solution was concentrated in vacuo. The residual trifluoroacetic acid was removed from residue by azeotrope with toluene (50 mL) then dichloromethane (30 mL) to yield the desired amine (390 mg, 99%) as a clear oil. MS (M+H)$^+$=311.

Step (2d): Following a procedure analogous to the preparation of Step (1e), but using the compound from of Step (2c) (390 mg, 0.88 mmoles) the amide was prepared, The crude compound was purified by silica gel chromatography to give the desired product (0.38 g, 92%) as a yellow oil. MS (M−Ot−Bu)$^+$=491.

Step (2e): Following a procedure analogous to the preparation of step (1f), but using the compound from Step (2d) (380 mg, 0.67 mmoles), the carboxylic acid was prepared. The product was precipitated from ethyl ether with hexanes, to give the desired acid (227 mg, 66%) as a white solid. MS (M−H)$^−$=507.

Step (2f): Following a procedure analogous to the preparation of compound of Step (1g), but using the compound from step (2e) (150 mg, 0.29 mmoles) the title compound was prepared. The crude was purified by reverse phase HPLC on a Vydac C-18 column to give the desired product (90 mg, 58%) as a white solid. MS (M−H)$^−$=522.

Example 3

(2R,3S) N1-[(3S)-hexahydro-1-(phenyl)-2-oxo-1H-azepin-3-yl]-N4-(hydroxy)-2-(2-methylpropyl)-3-(propyl)-butanediamide

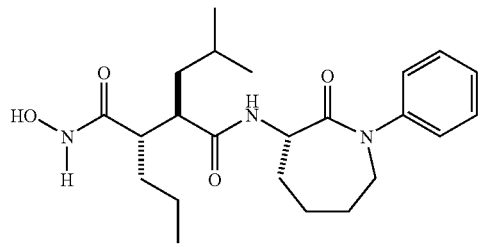

Step (3a): Triethylamine (1.5 mL, 10.8 mmoles), copper (II) acetate (0.95 g, 5.2 mmoles) and phenylboric acid (1.6 g, 13.1 mmoles) were added successively to a solution of compound of Step (1a) (1.0 g, 4.4 mmoles) in dichloromethane (20 mL). After 2.5 h at rt, more phenylboric acid (0.5 g, 4.1 mmoles) was added to the mixture. After an additional 3 hours at rt more phenylboric acid (0.5 g, 4.1 mmoles) was added to the mixture. After 65 h at rt, the mixture was filtered over celite. The filtrate was concentrated in vacuo, and the residue was purified by silica gel chromatography (ethyl acetate:hexanes, 5:95 then 15:85) to give the desired product (250 mg, 19%). MS (M−Ot−Bu)$^+$=231.

Step (3b): Following a procedure analogous to the preparation of compound of Step (2c), but using compound of Step (3a) (250 mg, 0.82 mmoles), the amine (300 mg, 99%) was prepared as a yellow oil. MS (M+H)$^+$=205.

Step (3c): Following a procedure analogous to the preparation of compound of Step (1e), but using compound from Step (3b) (0.3 g, 0.94 mmoles), the amide was prepared. The residue was purified by silica gel chromatography (ethyl acetate:hexanes, 5:95 to 20:80 in 5% increments, 500 mL each ratio) to give the desired product (210 mg, 60%) as a clear oil. MS (M+H−t−Bu)$^+$=403.

Step (3d): Following a procedure analogous to the preparation of compound of Step (1f), but using compound from sStep (3c) (200 mg, 0.44 mmoles) the acid was prepared. The crude oil was triturated with ether:hexanes 1:1 to give the desired acid (114 mg, 65%) as a white solid. MS (M−OH)$^+$=385.

Step (3e): Following a procedure analogous to the preparation of compound of Step (1g), but using compound from Step (3d) (82 mg, 0.20 mmoles) the title compound was prepared. The crude product was purified by reverse phase HPLC on a Vydac C-18 column to give the desired product (80 mg, 94%). MS (M−H)$^−$=416.

Example 4

(2R,3S) N1-[(3S)-hexahydro-1-(3-phenoxybenzyl)-2-oxo-1H-azepin-3-yl]-N4-(methyl)-2-(2-methylpropyl)-3-(propyl)-butanediamide

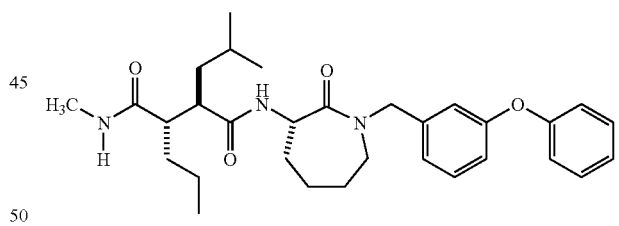

Following a procedure analogous to the preparation of Example 3, compound of Step (2e) (100 mg, 0.20 mmol) was treated with HATU (O-(7-azabenzotriazol-1-yl)-1,1,3,3,-tetramethyluronium hexafluorophosphate) (114 mg, 0.30 mmol) and N-methyl morpholine (66 mL, 0.6 mmol) in 2 mL of DMF for 15 min at rt. A solution of 2.0 M methylamine in THF (0.2 mL, 0.4 mmol) was added and the reaction solution was stirred for 1 h at rt. The reaction solution was diluted with 1N HCl (5 mL) and extracted 3× with 10 mL of ethyl acetate. The combined organic layers were washed with a saturated sodium bicarbonate solution (5 mL) and brine (5 mL), dried over magnesium sulfate, and concentrated in vacou to provide the crude amide. Purification by reverse phase HPLC on a Vydac-18 column provided the desired amide (30 mg, 30%). MS (M+Na)$^+$=544.

Example 5

(2R,3S) N1-[(3S)-hexahydro-1-(3-phenoxybenzyl)-
2-oxo-1H-azepin-3-yl]-N4-(methoxy)-N4-(methyl)-
2-(2-methylpropyl)-3-(propyl)-butanediamide

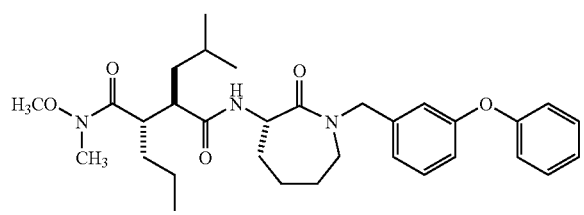

Following a procedure analogous to the preparation of Example 4, compound of Step (2e) (100 mg, 0.20 mmol) was activated and condensed with N,O-dimethylhydroxylamine hydrochloride (40 mg, 0.40 mmol). Purification by reverse phase HPLC on a Vydac-18 column provided the desired amide (30 mg, 30%). MS (M+Na)$^+$=574.

Example 6

(2R,3S) N1-[(3S)-hexahydro-1-(3-phenoxybenzyl)-
2-oxo-1H-azepin-3-yl]-N4-(methoxy)-2-(2-methyl-
propyl)-3-(propyl)-butanediamide

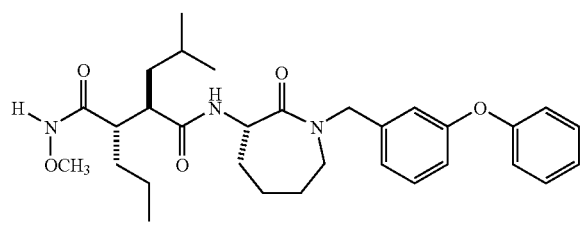

Following a procedure analogous to the preparation of Example 4, compound of Step (2e) (100 mg, 0.20 mmol) was activated and condensed with O-methylhydroxylamine hydrochloride (40 mg, 0.40 mmol). Purification by reverse phase HPLC on a Vydac-18 column provided the desired amide (30 mg, 30%). MS (M+Na)$^+$=560.

Example 7

(2R,3S) N1-[(3S)-hexahydro-1-(3-phenoxybenzyl)-
2-oxo-1H-azepin-3-yl]-2-(2-methylpropyl)-3-(pro-
pyl)-butanediamide

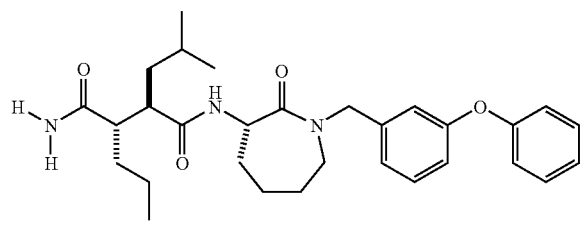

Following a procedure analogous to the preparation of Example 4, compound of Step (2e) (100 mg, 0.20 mmol) was activated and condensed with a 2.0 M solution of ammonia in dioxane (0.2 mL, 0.4 mmol). Purification by reverse phase HPLC on a Vydac-18 column provided the desired amide (30 mg, 30%). MS (M+Na)$^+$=530.

Example 7T

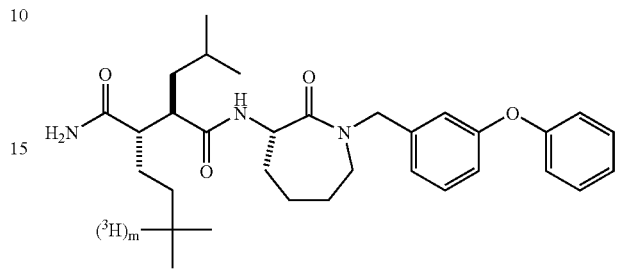

Example 7T was synthesized by reducing the double bond present in the compound of Example 8. Thus, the compound of Example 8 was dissolved in tetrahydrofuran and hydrogenated using tritium gas, by methods known to one skilled in the art organic synthesis. Purification by reverse phase HPLC on a Vydac-18 column provided the desired tritiated amide Example 7T wherein m is approximately 2.

Example 8

(2R,3S) N1-[(3S)-hexahydro-1-(3-phenoxybenzyl)-
2-oxo-1H-azepin-3-yl]-2-(2-methylpropyl)-3-(pro-
pyl)-butanediamide

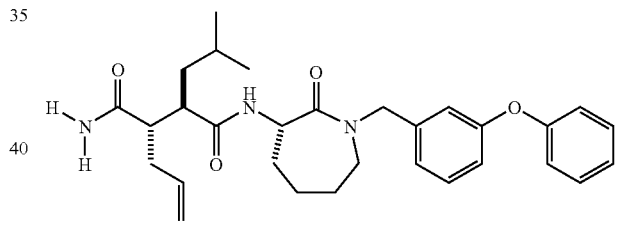

Example 8 was synthesized following a procedure analogous to the preparation of Example 7, but using succinate 9 (Scheme 2). The compound was purified by chromatography eluting with 5% methanol in CH$_2$Cl$_2$ to afford approx. 500 mg of Example 8. MS (M+Na)$^+$=528.

Example 9

(2R,3S) N1-[(3S)-hexahydro-1-(3-phenoxybenzyl)-
2-oxo-1H-azepin-3-yl]-N4-(hydroxy)-2-(2-methyl-
propyl)-3-(allyl)-butanediamide

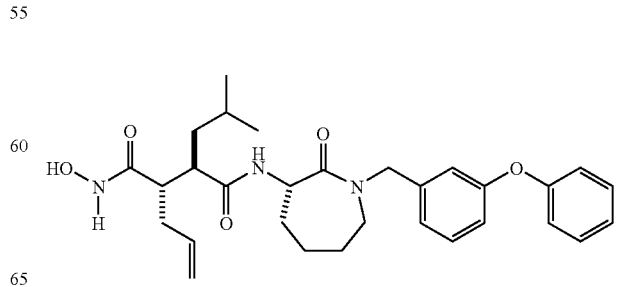

Example 9 was synthesized following a procedure analogous to the preparation of Example 2, but using succinate 9 (Scheme 2). Purification by reverse phase HPLC on a Vydac-18 column provided 150 mg of Example (9). MS (M+Na)$^+$=544.

Example 10

(2R,3S) N1-[(3S)-hexahydro-1-(benzophenon-3-yl)-2-oxo-1H-azepin-3-yl]-2-(2-methylpropyl)-3-(allyl)-butanediamide

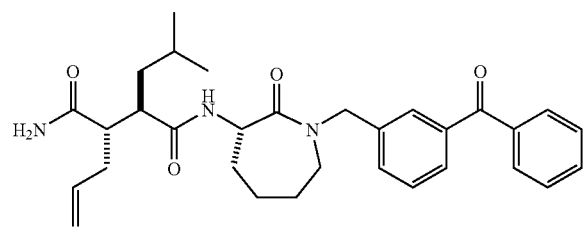

(Step 10-a): 3-Bromomethylbenzophenone. A solution of 3-methylbenzophenone (20 g, 102 mmol) dissolved in 40 mL of 1,2-dibromoethane was heated to reflux. Over a period of about 3 hours a solution of 105 mmol of bromine dissolved in 6 mL of 1,2-dibromoethane was added to the refluxing solution. After the addition was complete the solution was allowed to cool to rt and diluted with 100 mL of dichloromethane. The organic layer was extracted with 1×25 mL of 1 N HCl, 2×15 mL of NaHCO$_3$ Solution, and 2×25 ML of brine. The organic layers were dried over magnesium sulfate and concentrated in vacuo. The residue was then distilled to afford the product, 16.5 g (60%) as an oil that solidified upon standing, b.p. 160° C. at 300 mTorr. $^1$H NMR analysis shows that the product contains approximately 7% of the dibromide.

Step (10-b): 3-(1,1-dimethylethylcarbomethoxy-N-(benzophenone-3-yl-methyl)caprolactam. Diisopropylamine (4.2 mL, 30 mmol) was dissolved in 25 mL of THF and chilled to –78° C. To the solution was added 10 mL of 2.5M n-butyllithium in hexanes and the solution was warmed to 0° C. and allowed to stir for 10 min. A solution of Boc-protected aminocaprolactam 1a (5.0 grams, 22 mmol) dissolved in 25 mL of THF was then added and the reaction solution was stirred for 1 h at 0° C. Solid 3-bromomethyl-benzophenone was then added and the reaction solution was allowed to warm to rt and stir overnight. The reaction solution was diluted with water and extracted into ethyl acetate (100 mL). The organic layer was rinsed with 2×25 mL of 1 N HCl, 2×25 mL of saturated NaHCO$_3$ and 2×25 mL of brine, dried over magnesium sulfate, and dried in vacuo. Chromatography eluting with a gradient of 30% to 40% ethyl acetate in hexanes afforded the pure benzophenone-substituted caprolactam derivative (7.4 g, 80%). MS (M+Na)$^+$=445.

The title compound, Example 10, was synthesized in a manner analogous to the synthesis of the compound of Example 8 using succinate 9 and the benzophenone-substituted caprolactam derivative of the previous step. The compound was purified by crystallization from ethyl acetate to afford 0.26 g of crystals. MS (M+Na)$^+$=540.

Example 11

(2R,3S) N1-[(3S)-hexahydro-1-(benzophenon-3-yl)-2-oxo-1H-azepin-3-yl]-2-(2-methylpropyl)-3-(propyl)-butanediamide

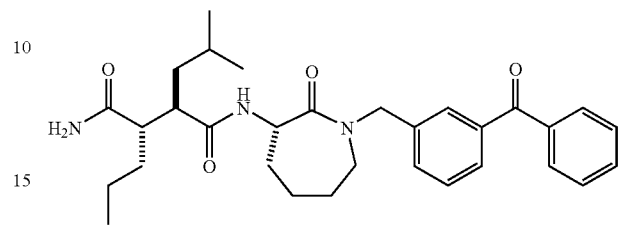

The compound of Example 11 was synthesized in a manner analagous to the synthesis of the compound of Example 8 using succinate 10 and the benzophenone-substituted caprolactam derivative of Step (10-b). The compound was purified by crystallization from ethyl acetate to afford 0.25 g of crystals. MS (M+Na)$^+$=542.

Example 11T

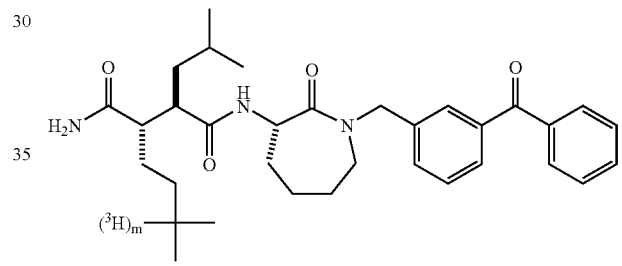

Example 11T was synthesized by reducing the double bond present in the compound of Example 10. Thus, the compound of Example 11T was dissolved in tetrahydrofuran and hydrogenated using tritium gas, by methods known to one skilled in the art organic synthesis. Purification by reverse phase HPLC on a Vydac-18 column provided the desired tritiated amide Example 11T wherein m is approximately 2.

Example 13

(2R,3S) N1-[(3S)-hexahydro-1-(3-(4-fluorophenyl)benzyl)-2-oxo-1H-azepin-3-yl]-N4-(hydroxy)-2-(2-methylpropyl)-3-(propyl)-butanediamide

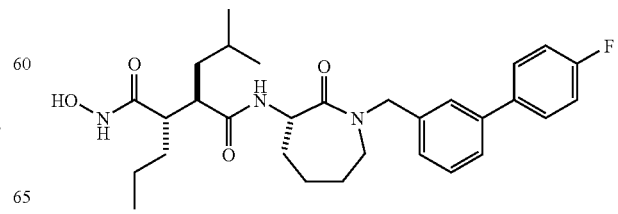

The general procedure reported for Scheme 5 was followed using 4-fluorophenyl boronic acid. Purification afforded 5.0 mg (54%) of the desired product. MS (M+Na)$^+$=548.

Example 16

(2R,3S) N1-[(3S)-hexahydro-1-(3-(3-methylphenyl)benzyl)-2-oxo-1H-azepin-3-yl]-N4-(hydroxy)-2-(2-methylpropyl)-3-(propyl)-butanediamide

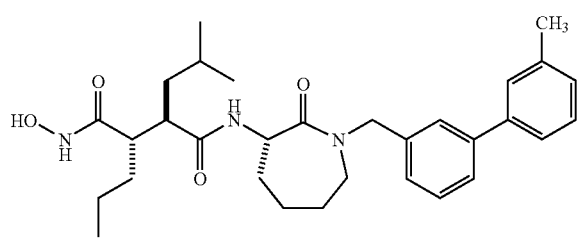

The general procedure reported for Scheme 5 was followed using 3-methylphenyl boronic acid. Purification afforded 3.0 mg (33%) of the desired product. MS (M+Na)$^+$=544.

Example 22

(2R,3S) N1-[(3S)-hexahydro-1-(3-(2-naphthyl)benzyl)-2-oxo-1H-azepin-3-yl]-N4-(hydroxy)-2-(2-methylpropyl)-3-(propyl)-butanediamide

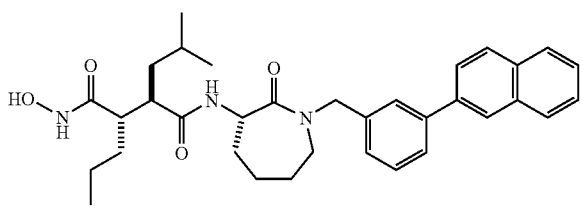

The general procedure reported for Scheme 5 was followed using 2-naphthyl boronic acid. Purification afforded 3.0 mg (31%) of the desired product. MS (M+Na)$^+$=580.

It will be understood by one skilled in the art that Scheme 6 can be followed in a manner analogous to the procedure for Scheme 5.

Example 23

(2R,3S) N1-[(3S)-hexahydro-1-(3-(4-methoxyphenyl)benzyl)-2-oxo-1H-azepin-3-yl]-2-(2-methylpropyl)-3-(propyl)-butanediamide

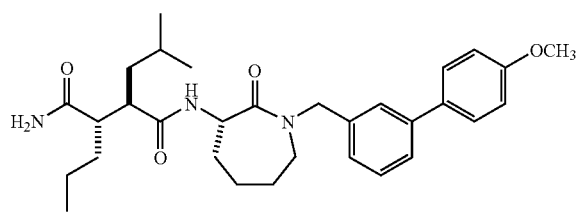

The general procedure reported for Scheme 6 was followed using 4-methoxyphenyl boronic acid. Purification afforded 0.5 mg of the desired product. MS (M+Na)$^+$=544.

Example 24

(2R,3S) N1-[(3S)-hexahydro-1-(3-(3-fluorophenyl)benzyl)-2-oxo-1H-azepin-3-yl]-2-(2-methylpropyl)-3-(propyl)-butanediamide

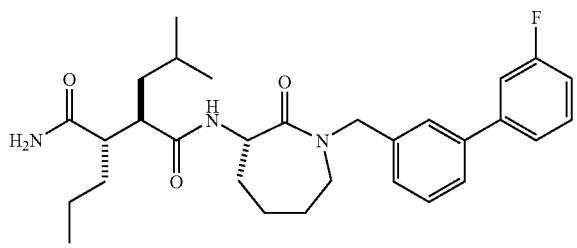

The general procedure reported for Scheme 6 was followed using 3-fluorophenyl boronic acid. Purification afforded 1.6 mg of the desired product. MS (M+Na)$^+$=532.

Example 25

(2R,3S) N1-[(3S)-hexahydro-1-(3-(4-trifluoromethylphenyl)-benzyl)-2-oxo-1H-azepin-3-yl]-2-(2-methylpropyl)-3-(propyl)-butanediamide

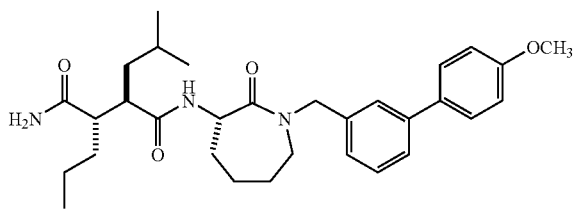

The general procedure reported for Scheme 6 was followed using 4-trifluoromethylphenyl boronic acid. Purification afforded 2.0 mg (40%) of the desired product. MS (M+Na)$^+$=582.

Example 26

(2R,3S) N1-[(3S)-hexahydro-1-(3-(4-methoxyphenyl)benzyl)-2-oxo-1H-azepin-3-yl]-2-(2-methylpropyl)-3-(propyl)-butanediamide

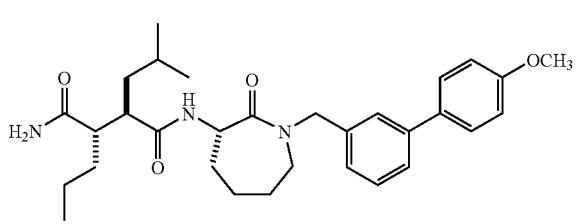

The general procedure reported for Scheme 6 was followed using 4-methoxyphenyl boronic acid. Purification afforded 0.5 mg of the desired product. MS (M+Na)$^+$=544.

Example 27

(2R,3S) N1-[(3S)-hexahydro-1-(3-(2,4-dichlorophenyl)benzyl)-2-oxo-1H-azepin-3-yl]-2-(2-methylpropyl)-3-(propyl)-butanediamide

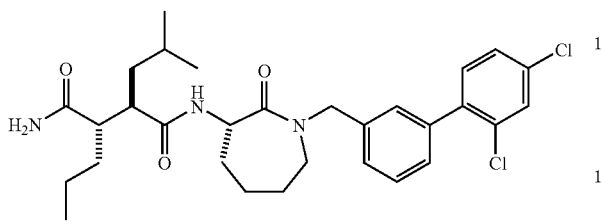

The general procedure reported for Scheme 6 was followed using 2,6-dichlorophenyl boronic acid. Purification afforded 1.8 mg (11%) of the desired product. MS (M+Na)$^+$=582.

Example 28

(2R,3S) N1-[(3S)-hexahydro-1-(3-(4-methylphenyl)benzyl)-2-oxo-1H-azepin-3-yl]-2-(2-methylpropyl)-3-(propyl)-butanediamide

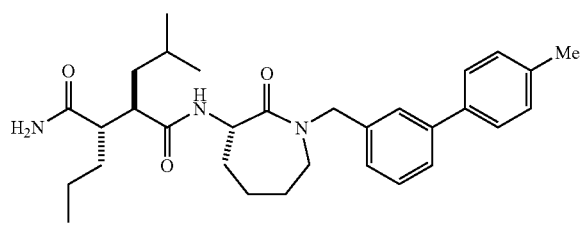

The general procedure reported for Scheme 6 was followed using 4-tolyl boronic acid. Purification afforded 1.8 mg (12%) of the desired product. MS (M+Na)$^+$=528.

Example 29

(2R,3S) N1-[(3S)-hexahydro-1-(3-(3-chloro-4-fluorophenyl)-benzyl)-2-oxo-1H-azepin-3-yl]-2-(2-methylpropyl)-3-(propyl)-butanediamide

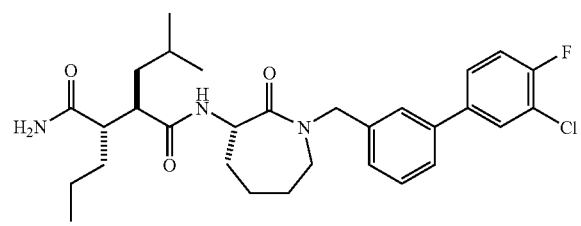

The general procedure reported for Scheme 6 was followed using 4-fluoro-3-chlorophenyl boronic acid. Purification afforded 0.5 mg (3.3%) of the desired product. MS (M+Na)$^+$=567.

Example 30

(2R,3S) N1-[(3S)-hexahydro-1-(3-(3-methoxyphenyl)benzyl)-2-oxo-1H-azepin-3-yl]-2-(2-methylpropyl)-3-(propyl)-butanediamide

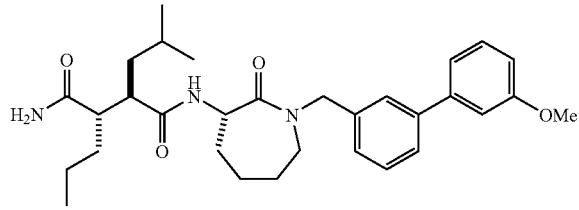

The general procedure reported for Scheme 6 was followed using 2-methoxyphenyl boronic acid. Purification afforded 0.8 mg (5.3%) of the desired product. MS (M+Na)$^+$=544.

Example 31

(2R,3S) N1-[(3S)-hexahydro-1-(3-(2-methoxyphenyl)benzyl)-2-oxo-1H-azepin-3-yl]-2-(2-methylpropyl)-3-(propyl)-butanediamide

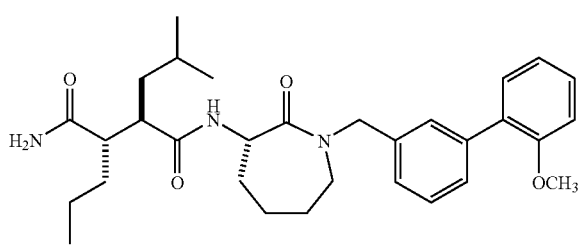

The general procedure reported for Scheme 6 was followed using 2-methoxyphenyl boronic acid. Purification afforded 1.5 mg (10%) of the desired product. MS (M+Na)$^+$=544.

It will be understood by one skilled in the art that Scheme 7 can be followed in a manner analogous to the procedure for Schemes 5 and 6.

Example 32

(2R,3S)N1-[(3S)-hexahydro-1-(3-(4-methoxyphenyl)pyrid-5-ylmethyl)-2-oxo-1H-azepin-3-yl]-2-(2-methylpropyl)-3-(propyl)-butanediamide

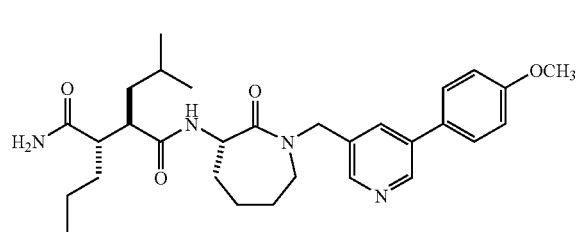

Amide 35 of Scheme 7 (0.10 g, 0.18 mmol) was dissolved in 5 mL of toluene and 41 mg (0.27 mmol) of 4-methoxyphenyl boronic acid was added, followed by 31 mg (0.0147 mmol) of tetrakis(triphenylphosphine)palladium, 0.5 mL of a 2M sodium cabonate solution and 0.5 mL of methanol. The reaction solution was heated to reflux for 16 h and then allowed to cool to rt. The reaction solution was diluted with 10 mL of water and extracted 2× with 50 mL of ethyl acetate. The combined organic layers were dried and concentrated and the resulting oil was purified by chromatography eluting with 30 to 100% ethyl acetate in hexanes as a solvent to provide 30 mg (29%) of biaryl product. MS (M+H)$^+$=580.

The purified biaryl product was dissolved in 10 mL of 1:1 trifluoroacetic acid/CH$_2$Cl$_2$ and stirred at rt for 2 h. The solvents were then removed under reduced pressure and the resulting oil was redissolved in 5 mL of toluene and reconcentrated to remove residual TFA. The crude acid (25 mg, 0.047 mmol) was then dissolved in 1 mL of DMF and 10 µL of N-methylmorpholine (0.094 mmol) and 42 mg (0.062 mmol) HATU were added and the reaction solution was stirred at rt for 45 min. Gaseous ammonia was then bubbled in at a gentle rate for about 1 minute and the solution was stirred for an additional 1 min. The reaction solution was then diluted with 10 mL of water and extracted 3× with 30 mL of ethyl acetate. The combined organic layers were dried and concentrated under reduced pressure to a solid which was purified by reversed phase HPLC to provide 3.5 mg (10%) of the compound of Example 30 as its trifluoroacetic acid salt. MS (M+H)$^+$=523.

Example 33

(2R,3S) N1-[(3S)-hexahydro-1-(3-(4-trifluoromethylphenyl)pyrid-5-ylmethyl)-2-oxo-1H-azepin-3-yl]-2-(2-methylpropyl)-3-(propyl)-butanediamide

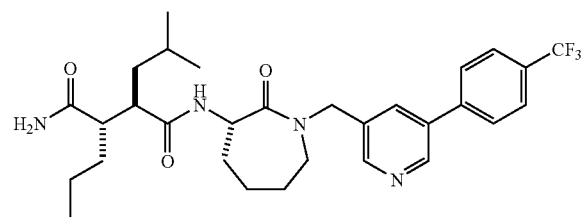

The general procedure reported for the compound of Example 32 was followed using 4-trifluoromethylphenyl boronic acid. Purification by HPLC afforded 6.0 mg of the desired product from as its trifluoroacetic acid salt. MS (M+Na)$^+$=583.

Example 34

(2R,3S) N1-[(3S)-hexahydro-1-(3-(3-chloro-4-fluorophenyl)pyrid-5-ylmethyl)-2-oxo-1H-azepin-3-yl]-2-(2-methylpropyl)-3-(propyl)-butanediamide

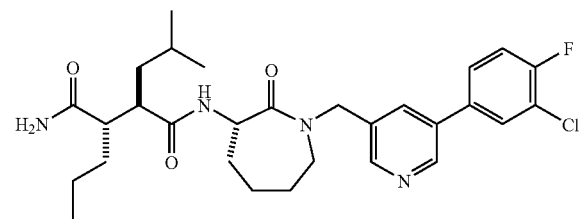

Amide 35 (0.30 g, 0.54 mmol) was dissolved in 3 mL of DMF and 123 mg (0.70 mmol) of 4-methoxyphenyl boronic acid was added, followed by 44 mg (0.0543 mmol) of bis(diphenylphosphinoferrocene) palladium (II) dichloride and 1.0 mL (7.18 mmol) of triethylamine. The reaction solution was heated to 80° C. for 24 h and then allowed to cool to rt. The reaction solution was diluted with 10 mL of water and extracted 2× with 50 mL of ethyl acetate. The combined organic layers were dried and concentrated and the resulting oil was purified by chromatography eluting with 20 to 100% ethyl acetate in hexanes as a solvent to provide 140 mg (50%) of biaryl product. MS (M+Na)$^+$=624.

The general procedure reported for the compound of Example 32 was then followed to provide the amide. Purification by chromatography eluting with 20 to 100% ethyl acetate in hexanes afforded 45 mg of the desired product of Example 34 as its trifluoroacetic acid salt. MS (M+Na)$^+$=567.

Example 39

(2R,3S) N1-[(3S)-hexahydro-1-(4-(4-trifluoromethylphenyl)-benzyl)-2-oxo-1H-azepin-3-yl]-2-(2-methylpropyl)-3-(propyl)-butanediamide

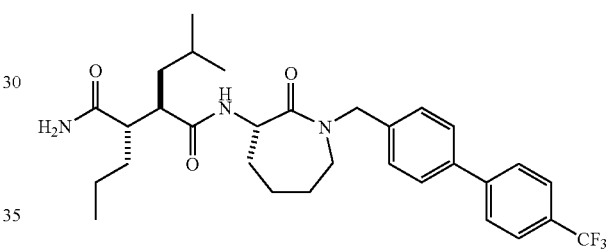

Step (39-a) 3-(1,1-dimethylethylcarbomethoxy-N-(4-bromophenylmethyl)caprolactam.

The title compound was synthesized in a manner analogous to the preparation of 3-(1,1-dimethylethylcarbomethoxy-N-(benzophenone-3-yl-methyl)caprolactam in Example 10 but using 4-bromobenzyl bromide as the alkylating agent. The compound was purified by chromatography eluting with 5–20% ethyl acetate in hexanes as eluent to provide 7.0 g (70%) of the title compound as a solid. MS (M+Na)$^+$=419.

Step (39-b) 3-(1,1-dimethylethylcarbomethoxy-N-(4,-(4'-trifluoromethylphenyl)phenylmethyl)caprolactam.

To a solution of 3-(1,1-dimethylethylcarbomethoxy-N-(4-bromophenylmethyl)caprolactam (0.5 g, 1.26 mmol) dissolved in 10 mL of toluene was added 263 mg (1.38 mmol) of 4-trifluoromethylphenyl boronic acid, 1 mL of methanol, and 1 mL of a 2M solution of potassium carbonate. The solution was degassed by nitrogen bubbling for 5 min, and then 33 mg of tris(dibenzylideneacetone)dipalladium(0) chloroform adduct and 66 mg of triphenylphosphine was added. The solution ws heated to reflux for 16 h and then allowed to cool and diluted with 20 mL of water. The aqueous layer was extracted 3× with 25 mL of ethyl acetate and concentrated. The resulting oil was purified by chromatography eluting with 20% ethyl acetate in hexanes to afford 0.47 g (81%) of an oil which crystallized on standing.

Step (39-d) The title compound, Example 39, was synthesized in a manner analagous to the synthesis of the compound of Example 8 using succinate 10 (280 mg, 1.04 mmol) and 3-(1,1-dimethylethylcarbomethoxy-N-(4,-(4'-trifluoromethylphenyl)-phenylmethyl)caprolactam. The compound was purified by chromatography eluting with 20–100% ethyl acetate in hexanes to afford 40 mg of a white powder. MS (M+H)+=560.

Example 40

(2S,3R) N1-[(3S)-hexahydro-1-(3-(2-tetrazolylphenyl)benzyl)-2-oxo-1H-azepin-3-yl]-2-(propyl)-3-(2-methylpropyl)-butanediamide

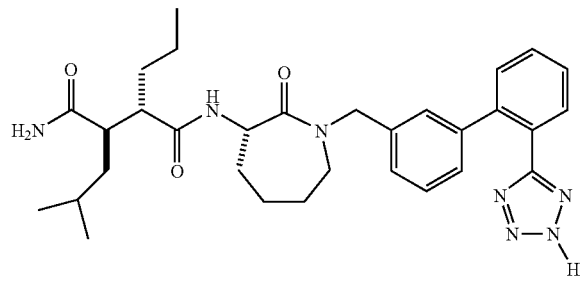

Step (40-a): The compound of Example 40 was synthesized in a manner analogous to the synthesis of the compound of Example 39, but using the substituted acid 28 of Scheme 6 (50 mg, 0.10 mmol) and o-((N-trityl)-tetrazole) phenylboronic acid under the conditions for the formation of the compound (39-b). The desired biaryl acid was isolated as an impure mixture (134 mg) and used directly in Step (40-b).

Step (40-b): The acid from Step (40-a) (134 mg, impure mixture) was converted to the amide under the conditions reported for the compound of Example 7. The crude amide was then dissolved in 2 mL of 10% trifluoroacetic acid in methanol and allowed to stir at rt for 30 min. The solvents were removed and the residue was purified by chromatography eluting with 10% methanol in ethyl acetate to provide 40 mg (71%, 2 steps) of the compound of Example 40 as a sticky powder. MS (M+Na)+=582.

Example 41

(2S,3R) N1-[(3S)-hexahydro-1-(3-phenoxybenzyl)-2-oxo-1H-azepin-3-yl]-2-(propyl)-3-(2-methylpropyl)-butanediamide

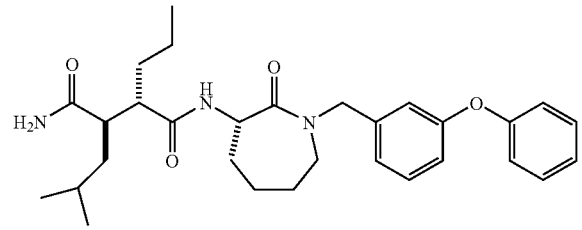

Step (41-a): The compound of Example 41 is formed by coupling Succinate 23 (480 mg, 1.21 mmol) with the substituted caprolactam TFA salt 2c under the conditions reported for the synthesis of the compound of Example 8. The crude fluorenylmethyl ester was used in the next step with out further purification. MS (M+Na)+=709.

Step (41-b): The crude fluorenylmethyl ester is dissolved in 2 mL of a 50% solution of piperidine in CH$_2$Cl$_2$ and stirred for 3 h at rt. A 10 mL portion of 1N HCl was then added and the mixture was extracted 3× with 10 mL of ethyl acetate. The crude acid was used in the next step with out further purification. MS (M+H)+=509.

The compound of Example 41 was then prepared using the acid from Step (41-b) under the conditions reported for compound of Example 7. The compound was purified by chromatography eluting with 5% methanol in CH$_2$Cl$_2$ to afford 120 mg (19%, 3 steps) of a white powder. MS (M+H)+=508.

Example 42

(2S,3R)N1-[1,3-dihydro-1-(3-phenoxybenzyl)-2-oxo-5-(phenyl)-2H-1,4-benzodiazepin-3-yl]-2-(2-methylpropyl)-3-(allyl)-butanediamide

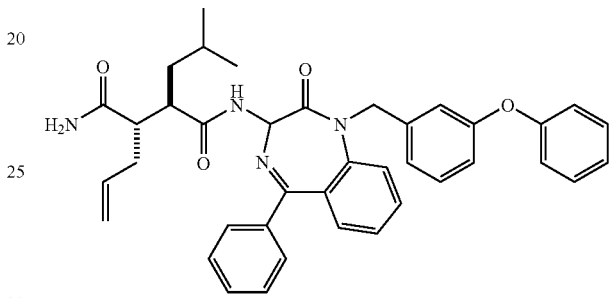

Step (42-a) 3-Phenoxybenzyl Iodide:

To a solution of 3-phenoxybenzyl chloride (10.0 g, 45.7 mmol) in 200 ml acetone was added sodium iodide (7.6 g, 507 mmol). The mixture was stirred at temperature overnight. The mixture was diluted with 300 ml hexane and the organic layer was washed twice with 5% sodium bicarbonate, once with brine and then dried over MgSO$_4$. Evaporation of the filtrate gave a light yellow oil. The product was used in next step without purification. $^1$H NMR (CDCl$_3$) 4.4 (s,2H), 6.8–7.4 (m, 9H).

Step (42-b):

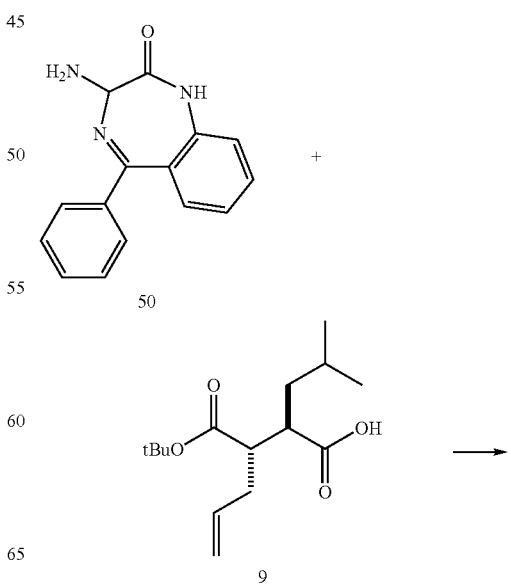

-continued

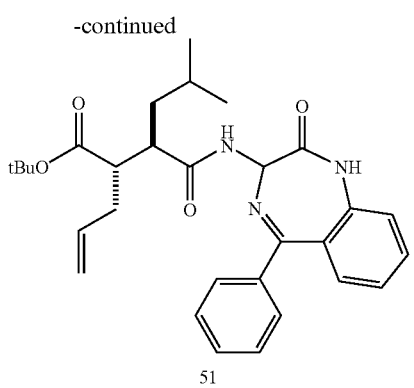

51

To a solution of benzodiazepine 50 (910 mg, 3.63 mmol), succinate 9 (980 mg, 3.63 mmol), hydroxybenzotriazole (980 mg., 7.25 mmol) and EDC (870 mg, 4.54 mmol) in 100 ml CH$_2$Cl$_2$ at 0 degrees was added triethylamine (0.76 ml, 5.45 mmol). The reaction mixture was washed with saturated sodium bicarbonate solution, 1.0N HCl, brine and dried over MgSO$_4$. Evaporation of the organic layer and purification by column chromatography on silica gel with hexane-ethyl acetate (7:3) gave 610 mg of benzodiazepine 51 as a white solid. M+H=504.37. $^1$H NMR (CDCl$_3$) 0.8–1.0 (m, 6H), 1.0–1.2 (m, 1H), 1.4–1.5 (d, 9H), 1.6–1.9 (m, 2H), 2.2–2.8 (m, 4H), 4.9–5.2 (m, 2H), 5.6 (dd, 1H), 5.6–6.0 (m, 1H), 7.0–7.6 (m, 9H).

Step (42-c):

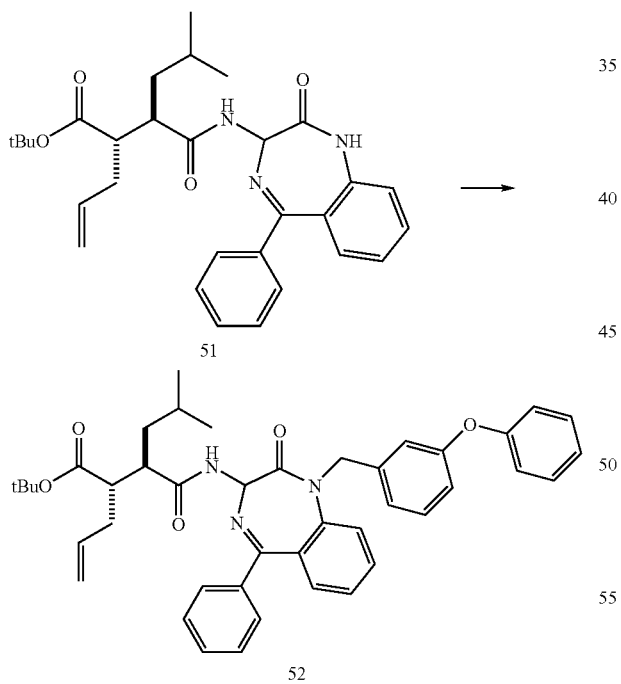

51

52

To a solution of benzodiazepine 51 (440 mg, 0.875 mmol) in DMF (20 ml) at 0 degrees was added NaH (45 mg, 1.12 mmol). The mixture was stirred at 0 degrees for 1.5 hr and then a solution of 3-phenoxylbenzyl iodide (330 mg, 1.06 mmol) in 10 ml DMF was added dropwise. The reaction mixture was allowed to warm to room temperature and stirred overnight. TLC using hexanes:EtOAc 6:4 (product Rf=0.31) indicated that the reaction was complete. The reaction mixture was quenched with water, and the solvent was evaporated under high vacuum, which provided a viscous yellow oil. The product benzodiazepine 52 was dissolved in ethyl acetate, which was washed with water (2×), brine and then dried over MgSO$_4$.

Evaporation of solvent gave 600 mg of benzodiazepine 52 as a yellow oil which was not further purified. M+H=686.3, M+Na=708.3. $^1$H NMR (CDCl$_3$) 0.8–1.0 (m, 6H), 1.0–1.3 (m, 1H), 1.4–1.5 (d, 9H), 1.5–1.9 (2H), 2.2–2.7 (4H), 4.6–4.8 (d,1H), 4.9–5.2 (m, 2H), 5.6–5.9 (m, 3H), 6.6–7.6 (m, 18H).

A solution of benzodiazepine 52 in 40 ml of TFA/CH$_2$Cl$_2$ (1:1) was stirred overnight at room temperature then evaporated to dryness. Repeated addition of toluene and evaporation provided 560 mg. of 53 as a yellow solid. (M–H=629.1)

Step (42-d):

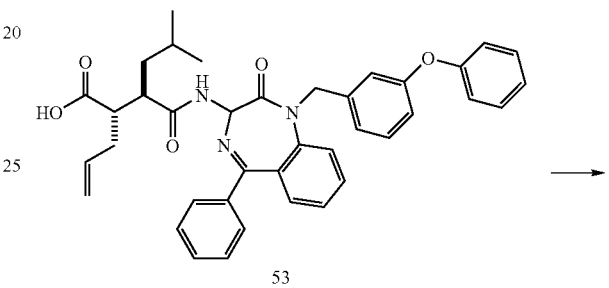

53

Example 42

To a solution of benzodiazepine 53 and HATU (410 mg, 1.08 mmol) in 30 ml DMF was added diisopropylethylamine (0.6 ml, 3.44 mmol) at 0 degrees. After 10 minutes, ammonia gas was bubbled through the solution for two minutes, and the reaction mixture was allowed to warm to room temperature and stirred overnight. Addition of water and solvent evaporation under high vacuum provided a yellow solid. The solid was taken up in ethyl acetate-water (1:1), and the organic layer was washed with water (2×), brine and then dried over MgSO$_4$. Evaporation of solvent gave a light yellow solid. Chromatographic purification on silica gel using CH$_2$Cl$_2$: methanol (10:0.5) gave 256 mg of Example 42. M+H=629.2 HNMR (CDCl$_3$) 0.8–1.0 (m, 6H), 1.2–1.4 (m, 1H), 1.6–2.0 (m, 2H), 2.2–2.8(4H), 4.6–4.8 (m, 1H), 5.0–5.2(m, 2H), 5.6–5.9 (m, 3H), 6.2–7.8 (m, 18H).

Example 43

(2S,3R) N1-[1,3-dihydro-1-methyl-2-oxo-5-(phenyl)-2H-1,4-benzodiazepin-3-yl]-2-(2-methylpropyl)-3-(allyl)-butanediamide

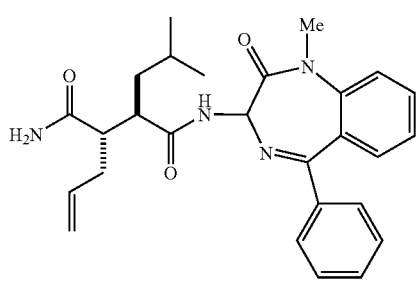

Step (43-a):

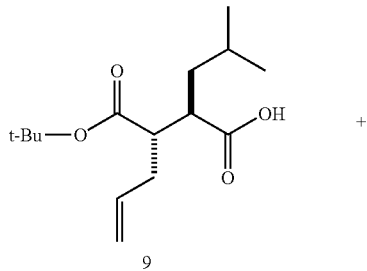

9

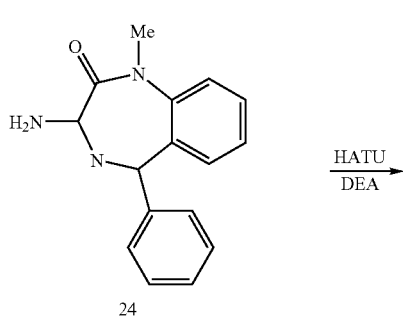

24

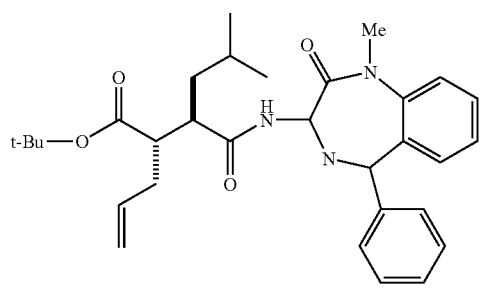

25

A solution of tert-butyl succinate ester 9 (1.1 eq.) in DMF (0.25 M) under $N_2$ at 0° C. was added HATU (1.1 eq.), then Hunig's base (4.0 eq.). The mixture was stirred at 0° C. for 10 mins. A solution of 2,3-dihydro-1-methyl-3-amino-5-phenyl-1H-1,4-benzodiazepin-2-one 54 in DMF (0.8 M) (1.0 eq.) was added to this solution. The reaction mixture was stirred overnight at room temperature and then transfered to a separatory funnel containing water. 30% n-Hexane in ethyl acetate was added which gave a clear organic layer. The aqueous solution was extracted twice with 30% n-hexane in ethyl acetate. The combined organic layers were washed with water and brine, dried over magnesium sulfate, and concentrated in vacuo. The residue was purified by chromatography on flash grade silica gel using 20% ethyl acetate in n-hexane. The compound 55 was isolated as an amorphous white solid (85%). Rf=0.25 (7:3 n-hexane:ethyl acetate).

$^1$H-NMR:(CDCl$_3$): δ7.61–7.21 (m, 10H); 5.77–5.73 (m, 1H); 5.57–5.54 (d, 1H); 5.20–4.97 (m, 2H); 3.47 (s, 3H); 2.63–2.33 (m, 4H); 1.80–1.76 (m, 2H); 1.47–1.46 (d, 9H); 1.43–1.11 (m, 1H); 1.01–0.86 (m, 6H).

MS: $C_{31}H_{39}N_3O_4$ (M+H) 518.3 (M+Na) 540.3.

Step (43-b):

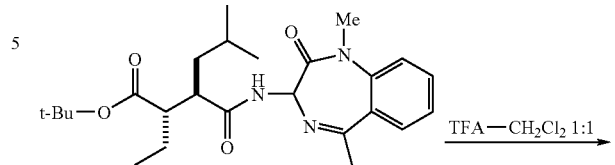

55

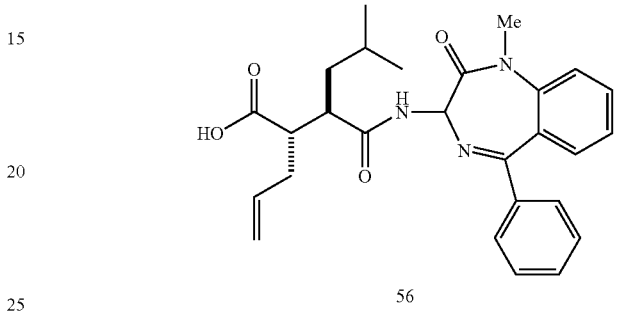

56

A solution of 55 in 50% TFA in methylene chloride (0.15M) was stirred at room temperature overnight. The solution was concentrated in vacuo, washed and concentrated four times with toluene in vacuo to give compound 56 as an amorphous solid (95%). Rf=0.64 (9.5 : 0.5 methylene chloride : methanol). MS: $C_{27}H_{31}N_3O_4$ (M+H) 462.

Step (43-c):

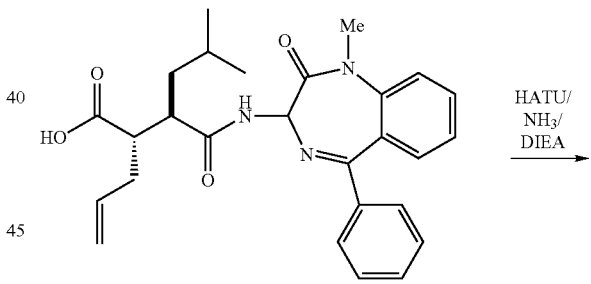

56

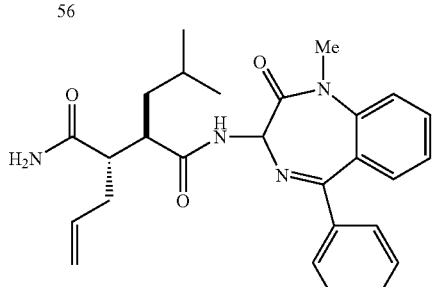

Example 43

To a solution of 56 (1.0 eq.) in DMF (0.25 M) under $N_2$ at 0° C. was added HATU (1.1 eq.), and then Hunig's base (4.0 eq.). The mixture was stirred at 0° C. for 10 mins, and then anhydrous ammonia bubbled through the solution for two minutes. The reaction mixture was stirred overnight at room temperature and then transfered to a separatory funnel containing water and diluted with 30% n-hexane in ethyl. The aqueous solution was extracted twice with 30% n-hexane in ethyl acetate. The combined organic layers were washed with water and brine, dried over magnesium sulfate, and concentrated in vacuo. The residue was purified by chromatography on flash grade silica gel using 4% methanol in methylene chloride. The title compound, Example 43, was isolated as an amorphous white solid (87%). Rf=0.43 (9:1 methylene chloride:methanol).

$^1$H NMR:(CDCl$_3$): δ 7.63–7.22 (m, 10H); 6.25–6.13 (d, 1H); 5.88–5.73 (m, 1H); 5.53–5.51 (dd, 1H); 5.44–5.41 (d, 1H); 5.22–5.04 (m, 2H); 3.47–3.46 (d, 3H); 2.74–2.31 (m, 4H); 1.81–1.61 (m, 2H); 1.34–1.22 (m, 1H); 0.99–0.87 (m, 6H).

MS: C$_{27}$H$_{32}$N$_4$O$_3$ (M+H) 461.

It is understood that the (R) or (S)-benzodiazepine diastereomer of Example 43 can be prepared using methods analogous to the present example but employing the (R) or (S) stereoisomer of intermediate 2a in Step (43-a), respectively.

Example 43T

Tritiated (2S,3R) N1-[1,3-dihydro-1-methyl-2-oxo-5-(phenyl)-2H-1,4-benzodiazepin-3-yl]-2-(2-methylpropyl)-3-(n-propyl)-butanediamide

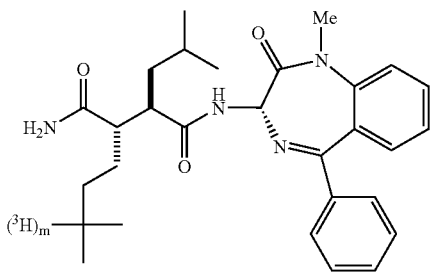

Example 43T was synthesized by reducing the double bond present in the (S)-benzodiazepine diastereomer of Example 43. The (S) diastereomer of Example 43 may be separated from the product of Step (43-c) by means known to one skilled in the art and the single isomer reduced. Alternatively, this diastereomer may be prepared directly as stated above. Thus, the (S)-benzodiazepine diastereomer of Example 43 was dissolved in tetrahydrofuran and hydrogenated using tritium gas, by methods known to one skilled in the art organic synthesis. Purification by reverse phase HPLC on a Vydac-18 column provided the desired tritiated amide Example 43T wherein m is approximately 2.

It is understood that one skilled in the art of organic synthesis can synthesize radiolabeled compounds of the present invention for use as a tagged inhibitor of beta-amyloid production using radiolabeling techniques well know in the art. For example tritiation, using catalysts such as Pd/C or Wilkinson's catalyst and $^3$H$_2$ gas, one skilled in the art can reduce olefin precursors. Examples of olefin precursors are Examples 8, 10, 42, 43, intermediate Succinate 10 and intermediate Benzodiazepine 51.

Representative Procedures for the Synthesis of Radiolabeled Compounds

Described below are representative procedures for the synthesis of radiolabeled compounds. These nonlimiting representative procedures, and other procedures known in the art, will be readily known and appreciated by one of skill in the art of organic synthesis of radiolabeled compounds. The radiolabeled ligands of macromolecules involved in the process of APP and/or beta-amyloid production (the "radiolabeled ligands") of the present invention can be synthesized using standard synthetic methods known to those skilled in the art, using radioisotopes of halogens (such as chlorine, fluorine, bromine and iodine), as well as others. Radioisotopes include $^{123}$I, $^{125}$I, $^{131}$I, $^{99m}$Tc, and $^{111}$In.

The radiolabeled ligands of the invention may be labeled either directly (that is, by incorporating the radiolabel directly into the compounds) or indirectly (that is, by incorporating the radiolabel into the compounds through a chelator which has been incorporated into the compounds. For brain imaging, it is expected that direct labeling will be preferred in the present invention. For direct labeling, as those skilled in the art will recognize, the labeling may be isotopic or nonisotopic. With isotopic labeling, one group already present in the compound is substituted with (exchanged for) the radioisotope. With nonisotopic labeling, the radioisotope is added to the compound without substituting with (exchanging for) an already existing group.

Generally, labeled compounds are prepared by procedures which introduce the labeled atom at a late stage of the synthesis. This allows for maximum radiochemical yields, and reduces the handling time of radioactive materials. When dealing with short half-life isotopes, a major consideration is the time required to conduct synthetic procedures, and purification methods. Protocols for the synthesis of radiopharmaceuticals are described in Tubis and Wolf, Eds., "Radiopharmacy", Wiley-Interscience, New York (1976); Wolf, Christman, Fowler, Lambrecht, "Synthesis of Radiopharmaceuticals and Labeled Compounds Using Short-Lived Isotopes", in Radiopharmaceuticals and Labeled Compounds, Vol 1, p. 345–381 (1973), the disclosures of each of which are hereby incorporated herein by reference, in their entirety.

Various procedures may be employed in preparing the radiolabeled compounds of the invention where the radiolabel is a halogen. Some common synthetic methodologies for isotopic halogen labeling of aromatic compounds such as the type present here are iododediazonization, iododeborobation, iododestannylation, iododesilation, iododethallation, and halogen exchange reactions. The most common synthetic methodology for nonisotopic halogen labeling of aromatic compounds such as the type present here is iododeprotonation or electrophilic aromatic substitution reactions. These methods and additional procedures are described in Merkushev, Synthesis, 923 (1988), and Seevers et al., Chem. Rev., 82: 575 (1982), the disclosures of each of which are hereby incorporated herein by reference, in their entirety.

By way of example, isotopically radiolabeled 4, 5 and 6-halo t-butyloxycarbonyl-3-aminomethylbenzoic acid derivatives may be prepared using the general procedures described above for the synthesis of the unlabeled compounds. In carrying out such radiolabeling, it is important that the half-life of the isotope chosen be much longer than the handling time of the reaction sequences. Known starting materials include the 2, 3, and 4-iodo (123I, 125I, and 131I) benzoic acids. Iodo-radiolabeled compounds may also be isotopically prepared from anilines by the Sandmeyer reaction as described in Ellis et al., Aust. J. Chem., 26: 907 (1973).

Alternatively, radiolabeled compounds may prepared by way of isotopic labeling from an unlabeled bromo or iodo derivatives by various two step reaction sequences, such as through the use of trialkylsilyl synthons as described in Wilson et al., J. Org. Chem., 51: 483 (1986) and Wilbur et al., J. Label. Compound. Radiopharm., 19: 1171 (1982), the use of trialkylsilyl synthons as described in Chumpradit et al. J. Med. Chem., 34: 877 (1991) and Chumpradit et al J. Med. Chem., 32: 1431 (1989), and the use of boronic acid synthons as described in Kabalka et al., J. Label. Compound. Radiopharm., 19: 795 (1982) and Koch et al., Chem. Ber., 124:2091 (1991).

In preparing radiolabeled compounds of the present invention, to maximize radiochemical yields, to reduce the handling time of radioactive materials, and to prepare short half-life halogen labeled compounds, it is preferable to perform the isotopic halogen labeling as one of the final steps in the compound synthesis. The following provides exemplary proceudres for such late stage labeling.

Unlabeled iodo compounds are versatile precursors which can be converted to the labeled derivatives by any of the two step reaction sequences described above. In general, useful functionalities to incorporate into a compound includes bromo, the nitro, the trialkylsilyl, the trialkyltin, and the boronic acid groups. The synthesis and application of each of these precursors is described above. Radioiodination of a compound of the present invention may be achieved via isotopic labeling during the final stages of preparation by the substitution of radioactive iodide for a stable iodine atom already present in the molecule. This can often be done by heating the compound with radioactive iodide in an appropriate solvent as described in Ellis et al., Aust. J. Chem., 26: 907 (1973).

In some cases radiolabeled compounds of the present invention may also be isotopically iodo-labeled during the final stages of their preparation from anilines by the Sandmeyer reaction as described in Ellis et al., Aust. J. Chem., 26: 907 (1973). Alternatively, a compound may be isotopically labeled late in the reaction scheme from the unlabeled bromo or iodo derivatives by various two step reaction sequences, as described above, such as through the use of trialkylsilyl synthons as described in Wilson et al., J. Org. Chem., 51: 4833 (1986) and Wilbur et al., J. Label. Compound. Radiopharm., 19: 1171 (1982), through the use of trialkylsilyl synthons as described in Chumpradit et al., J. Med. Chem., 34: 877 (1991) and Chumpradit et al., J. Med. Chem., 32: 1431 (1989), and through the use of boronic acid synthons as described in Kabalka et al., J. Label. Compound. Radiopharm., 19: 795 (1982) and Koch et al., Chem. Ber., 124:2091 (1991).

A related approach where the isotopic halogen radiolabeling may be carried out late in the synthesis scheme involves converting a synthetic intermediate compound that already incorporates a trialkylsilyl, trialkyltin, or boronic acid groups. Labeled iodo derivatives may also be readily prepared nonisotopically from the amino, hydroxy, or methoxy substituted compounds as described in Arora et al J. Med. Chem., 30:918 (1987). Electrophilic aromatic substitution reactions are enhanced by the presence of such electron-donating substituents.

Another representative approach to the incorporation of a radiolabeled halogen in compounds containing methyl substituted phenyl involves the conversion to a a-halotoluene derivative with NBS or NCS under free-radical halogenation conditions. The benzylic halides may be smoothly replaced by radiolabeled iodide through a nucleophilic substitution reaction. The above described process chemistry can also be used to prepare any radioactive halogen isotope.

By way of illustration, $^{18}F$ derivatives of certain compounds can be prepared by conjugation of $^{18}F$ functionalized phenyl intermediates (R. H. Mach et al., J. Med. Chem., 1993, 36,3707–3720).

Utility

Aβ production has been implicated in the pathology of Alzheimer's Disease (AD). The compounds of the present invention as well as compounds determined from the present invention have utility for the prevention and treatment of AD by inhibiting the proteolytic activity leading to Aβ production. Methods of treatment target formation of Aβ production through the enzymes involved in the proteolytic processing of β amyloid precursor protein. Compounds that inhibit β or γsecretase activity, either directly or indirectly, control the production of Aβ. Such inhibition of β or γsecretases reduces production of Aβ, and is expected to reduce or prevent the neurological disorders associated with Aβ peptide, such as Alzheimer's Disease.

Cellular screening methods for inhibitors of Aβ production, testing methods for the in vivo suppression of Aβ production, and assays for the detection of secretase activity are known in the art and have been disclosed in numerous publications, including PCT publication number WO 98/22493, EPO publication number 0652009, U.S. Pat. No. 5,703,129 and U.S. Pat. No. 5,593,846; all hereby incorporated by reference.

The compounds of the present invention as well as compounds determined from the present invention have utility for the prevention and treatment of disorders involving Aβ production, such as cerebrovascular disorders.

Compounds of Formula (I) are expected to possess γ-secretase inhibitory activity. The γ-secretase inhibitory activity of the compounds of the present invention is demonstrated using assays for such activity, for example, using the assay described below. Compounds within the scope of the present invention have been shown to inhibit the activity of γ-secretase, as determined using assays for such activity.

Compounds provided by this invention should also be useful as standards and reagents in determining the ability of a potential pharmaceutical to inhibit Aβ production. These would be provided in commercial kits comprising a compound of this invention.

As used herein "μg" or "ug" denotes microgram, "mg" denotes milligram, "g" denotes gram, "μL" denotes microliter, "mL" denotes milliliter, "L" denotes liter, "nM" denotes nanomolar, "μM" or "uM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetate.

A compound is considered to be active if it has an $IC_{50}$ or $K_i$ value of less than about 100 μM for the inhibition of Aβ production or inhibition of proteolytic activity leading to Aβ production. Compounds, as demonstrated by use of the invention, have demonstrated $IC_{50}$ values, for the inhibition of Aβ production, of less than about 100 μM. Preferably compounds, as demonstrated by use of the invention, demonstrate $IC_{50}$ values, for the inhibition of Aβ production, of less than about 1 μM. More preferably compounds, as demonstrated by use of the invention, demonstrate $IC_{50}$ values, for the inhibition of Aβ production, of less than about 100 nM. Even more preferably compounds, as demonstrated by use of the invention, demonstrate $IC_{50}$ values, for the inhibition of Aβ production, of less than about 50 nM.

β Amyloid Precursor Protein Accumulation Assay (βAPPA Assay)

An assay to evaluate the accumulation of Aβ protein was developed to detect potential inhibitors of secretases. The assay uses the CHO N 9 cell line, characterized for expression of exogenous APP by immunoblotting and immunoprecipitation.

The effect of test compounds on the accumulation of Aβ in the conditioned medium is tested by immunoprecipitation. N 9 cells are grown to confluency in 6-well plates and washed twice with 1× Hank's buffered salt solution. The cells are starved in methionine/cysteine deficient media for 30 min., followed by replacement with fresh deficient media containing 150 uCi Tran35S-LABEL™ (ICN). Test compounds dissolved in DMSO (final concentration 1%) are added, over a range of 1 picomolar to 100 micromolar, together with the addition of the fresh media containing Tran35S-LABEL™. The cells are incubated for 4 h at 37° C. in a tissue culture incubator.

At the end of the incubation period, the conditioned medium is harvested and pre-cleared by the addition of 5 µl normal mouse serum and 50 ul of protein A Sepharose (Pharmacia), mixed by end-over-end rotation for 30 minutes at 4° C., followed by a brief centrifugation in a microfuge. The supernatant is then harvested and transferred to fresh tubes containing 5 ug of a monoclonal antibody (examples of antibodies include but are not limited by, clone 1101.1, directed against an internal peptide sequence in Aβ; or 6E10 from Senetek; or 4G8 from Senetek; additionally polyclonals from rabbit antihuman Aβ from Boehringer Mannheim) and 50 µl protein A Sepharose. After incubation overnight at 4° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli U.K. Cleavage of structural proteins during the assembly of the head of bacteriophage T4. Nature 227, 680–5, 1970.) and boiled for 3 minutes. The supernatant is then fractionated on either 10–20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound in this assay blocks Aβ accumulation in the conditioned medium, and is considered active with an $IC_{50}$ less than 100 µM.

C-Terminus β Amyloid Precursor Protein Accumulation Assay (CTF Assay)

The effect of test compounds on the accumulation of C-terminal fragments is determined by immunoprecipitation of APP and fragments thereof from cell lysates. N 9 cells are metabolically labeled, as above, with media containing Tran35S-LABEL™, in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% NaN₃). Again, lysates are precleared with 5 ul normal rabbit serum/ 50 ul protein A Sepharose, followed by the addition of BC-1 antiserum (15 µl;) and 50 µl protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound in this assay stimulates C-terminal fragment accumulation in the cell lysates, and is considered active with an $IC_{50}$ less than 100 µM.

Accumulation-Release Assay

This immunoprecipitation assay is specific for γ secretase activity (i.e., proteolytic activity required to generate the C-terminal end of Aβ either by direct cleavage or generating a C-terminal extended species which is subsequently further proteolyzed). N 9 cells are pulse labeled with media containing Tran35S-LABEL™ in the presence of a reported γ secretase inhibitor (MDL 28170; Higaki J, Quon D, Zhong Z, Cordell B. Inhibition of beta-amyloid formation identifies proteolytic precursors and subcellular site of catabolism. Neuron 14, 651–659, 1995) for 1 h, followed by washing to remove $^{35}S$ radiolabel and MDL 28170. The media is replaced and test compounds are added over a dose range (for example 0.1 nM to 100 uM). The cells are chased for increasing periods of times and Aβ is isolated from the conditioned medium and C-terminal fragments from cell lysates (see accumulation assay above). The activity of test compounds are characterized by whether a stabilization of C-terminal fragments is observed and whether Aβ is generated from these accumulated precursor. A typical test compound in this assay prevents the generation of Aβ out of accumulated C-terminal fragments and is considered active with an $IC_{50}$ less than 100 µM.

Radioligand Competition Binding Assay (RCB Assay):

The following assay, of the invention, discloses a novel assay to rapidly screen and evaluate potential inhibitors of secretases. The assay enables screening for inhibitors of Aβ production or inhibitors of proteolytic activity leading to the production of Aβ by using a competitive binding assay wherein more than one chemical entity competes for a binding site identified for Aβ production. For example, in a competitive binding assay of the invention competition occurs between potential Aβ production inhibitors (i.e. compounds being investigated for inhibitory activity) and a standard known for Aβ production inhibitory activity which standard has been tagged by a radiolabel. Example 7T radiolabeled with tritium is a standard identified for Aβ production inhibitory activity; however, any radiolabelled or tagged compound binding to the same site as Example 7T could be used in this assay. It is understood that the theory of competitive binding is well known to one skilled in the art of pharmacology. The compounds identified by this invention may have utility for the prevention and treatment of neurological disorders relating to Aβ production, including Alzheimer's disease, by inhibiting Aβ production.

Materials:

Assay buffer: Hepes 50 mM pH 7.0.

Competing compounds/potential inhibitors: weigh and dilute in 100% DMSO at a concentration of $1 \times 10^{-2}$M. From that stock, a second ($6 \times 10^{-4}$M) stock is made in 100% DMSO. The working stock ($6 \times 10^{-5}$M) is made from the second in assay buffer containing 6% DMSO.

Wash buffer: Phosphate buffered saline containing 0.01% triton X-100, pH 7.0 at 4° C.

Membrane: $HEK_{293}$ control membranes (Receptor Biology, Inc.), or rat whole brain homogenates prepared as follows: Frozen pellets of approximately 10 mg protein $HEK_{293}$ cell membranes are thawed on ice and homogenized in 10 ml of assay buffer, using a Brinkman Polytron (PT-10) setting 6 for 10 sec. The homogenate was centrifuged at 48,000×g for 12 minutes and the resulting pellet washed by repeating the homogenization and centrifugation steps. The final cell pellet was resuspended in buffer to yield a protein concentration of approximately 0.35 mg/ml as assayed by the method of Bradford (1976) using bovine serum albumin as the standard.

Rats: for the rat whole brain homogenates, (male Sprague-Dawley rats 200 to 300 g., Charles River) are decapitated and brains dissected on an ice-chilled glass plate. Brains weighing ~2 g are homogenized in 20 ml of assay buffer and prepared by the method described above for the cell homogenates. The final pellet is resuspended to yield a protein conc. of ~5 mg/ml original wet weight.

Radiolabeled standard: [$^3$H] I-7T (Example 7T; synthesized by Dupont Pharm. Co.) S.A. 87.5 Ci/mMol, (11.43 µM I-7T).

Radioligand Competition Binding Assay Method:

Assays are initiated by addition of 150 µl membrane suspension (~0.35 mg protein/ml) to 150 µl of assay buffer containing 1% DMSO, 5 to 30 nM [$^3$H] I-7T, and various concentrations of inhibitors over a range of 1 picomolar to 100 micromolar. Binding assays are preformed in duplicate in disposable polypropylene 96 well plates, (Costar Corp., Cambridge, Mass.) in a final volume of 0.3 ml. Nonspecific binding is defined in the presence of 3 µM I-7T. Optimum incubation time at 23° C. is 1 hour. The separation of bound radioligand I-7T from free radioligand I-7T is accomplished by rapid vacuum filtration of the incubation mixture over GFF glass fiber filters (Inotech Biosystems International, Lansing, Mich.) presoaked for 2 hours in 0.3% polyethylinamine (pH 13) using an Inotech cell harvester. Filters were washed 2 times with 0.3 ml of ice-cold phosphate buffered saline pH 7.0 containing 0.01% Triton X100. Filters are accessed for radioactivity by liquid scintillation counting using a Packard 2500 TR (Packard Instrument Co., Downers Grove, Ill.), having a counting efficiency for tritium of ~56%.

Alternatively, it is well known in the art that a homogenous assay format, such as a scintillation proximity assay (SPA), could be employed in the radioligand competition binding assay of the invention. For example, membranes or membrane extracts can be immobilized onto the SPA support, after which the support is then incubated with a tagged inhibitor of beta amyloid production in the presence of a potential inhibitor of beta amyloid production. The SPA support, by nature of its construction, magnifies the radioactive scintillation signal of bound radioactive compounds while not magnifying the radioactive signal of radioactive compounds free in solution. Therefore, the bound tagged inhibitor of beta amyloid production is detected and quantified by scintillation counting in the presence of free tagged inhibitor of beta amyloid production.

It is understood that the process of separating bound tagged inhibitor of beta amyloid production from free tagged inhibitor of beta amyloid production, for example bound radioligand I-7T from free radioligand I-7T, can be conducted in a number of methods. For example the process of separating includes, but is not limited to, filtration or centrifugation. The process of separating is intended to facilitate quantification of bound tagged inhibitor of beta amyloid production. Therefore, the process of separating is also intended to encompass homogeneous techniques, for example SPA, where free tagged inhibitor of beta amyloid production in situ is separated from the tagged inhibitor of beta amyloid production bound to the solid support of the scintillant. Thus, in a homogeneous technique such as SPA, the free and bound inhibitors are considered separated from each other within the meaning of the invention.

Radioligand Competition Binding Data Analysis:

Resulting disintigrations per minute (dpm's) are expressed as percent inhibition of [$^3$H] I-7T specific binding. IC$_{50}$ values of competing compounds are calculated using the program GraphPad Prism by GraphPad Software, (San Diego, Calif.). It is understood that one skilled in the art can determine these values using this program.

A good correlation for inhibition of proteolytic activity leading to Aβ production has been found between compounds identified in functional assays for determination of Aβ production, for example the β Amyloid Precursor Protein Accumulation Assay, and compounds identified in the Radioligand Competitive Binding Assay. The correlation is demonstrated by plotting the IC$_{50}$ values of compounds identified in the functional assay verses the IC$_{50}$ values of compounds identified in the RCB Assay. Compounds from several chemical series, including Examples disclosed herein, have exhibited, over a range of potencies, similar IC$_{50}$ values in the RCB Assay as seen in an accumulation assay.

Example 98

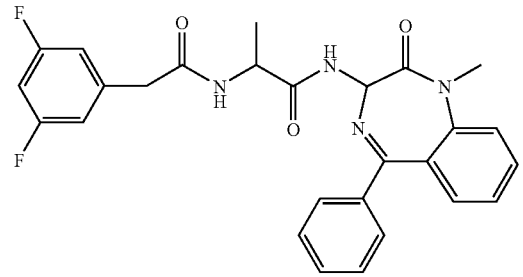

The compound of Example 98 was synthesized according to procedures disclosed in PCT Application WO98/28268, published Jul. 2, 1998.

Example 98b

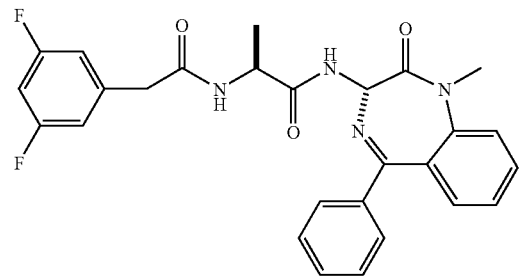

The compound of Example 98b was synthesized according to procedures disclosed in PCT Application WO98/28268, published Jul. 2, 1998.

Example 99

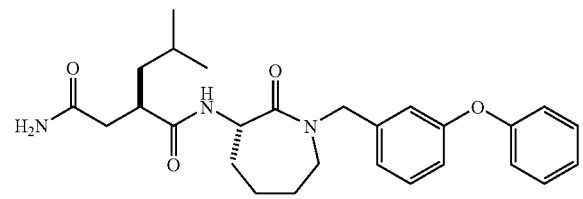

Step (99a): The compound of Step (99a) is formed by coupling succinate 7 (115 mg, 0.5 mmol) with the substituted caprolactam TFA salt (212 mg, 0.5 mmol) from Step (2c) of Example 2 under the conditions reported for the synthesis of the compound of Example 8. The crude tert-butyl ester was taken on without further purification.

Step (99b): The compound of Step (99b) is formed by dissolving the crude product from Step (99a) in 5 mL of a 1:1 solution of TFA/$CH_2Cl_2$ and stirring at room temperature for 2 hours. Concentration followed by reconcentration twice from 10 mL of toluene provides the crude acid which was taken on with no further purification.

Step (99c): The title compound, Example 99, was prepared using the acid from Step (99b) under the conditions reported for the compound of Example 7. The compound was purified by chromatography eluting with 5% methanol in $CH_2Cl_2$ to afford 50 mg (21%, 3 steps) of a white powder. MS $(M+Na)^+=488$.

Example 100

Binding of Example 7T to Cell Membranes:

A survey of different cell lines was performed using the radioligand competition binding assay, of the invention, with Example 7T to identify membranes rich in binding sites for Example 7. Cell lines useful for performance of the RCB Assay are preferentially human or mammalian cell lines. It is more prefered that the cell lines express presenilin 1, presenilin 2 and/or presenilin homologs (for example SEL-12). The cell lines surveyed included HEK293 cells (ATCC CRL-1573), IMR 32 (ATCC CCL-127), RAJI (ATCC CCL-86), CHO (ATCC CRL-9096), U-937 (ATCC CRL-1593), and THP-1 (ATCC TIB-202). Of the cell lines surveyed the best signal to noise ratio (i.e., ratio of specific binding and non-specific binding) was obtained using THP-1 cell membranes.

Example 101

Characterization of the Example 11T in the Radioligand Competition Binding Assay:

Example 11, a benzophenone derivative of Example 7, was synthesized. When Example 11 was assayed in the βAPPA Assay and separately in the RCB Assay with Example 7T as the radiolabeled standard, a statistically significant correlation of $IC_{50}$ values was observed between the two Assays.

Radiolabeled Example 11, i.e. Example 11T, was synthesized and tested in the RCB Assay for equivalency to Example 7T. The apparent Ki was calculated for four compounds (Example 7, Example 11, Example 98, and Example 99) and an statistically significant correlation was observed between results obtained whether the RCB Assay was conducted with Example 7T or Example 11T, indicating that Example 11 binds to the same molecular target(s) in cell membranes. Therefore, it was found that Example 11T could be used instead of Example 7T as the radioactive tracer in the RCB Assay.

Analogously, it has also been found that Example 43T can be used instead of Example 7T as the radioactive tracer in the RCB Assay.

Example 102

Example 11 Reduces the Bmax of Example 7T:

Cell membranes (THP-1) were incubated with Example 11 at approximately 3 times the $K_d$ concentration for 1 hour at room temperature under the conditions outlined for the RCB Assay. Membranes were photolysed at 365 nm for 1 hour on ice. Control membranes were incubated in parallel on ice. The membranes were harvested (centrifuged at 40,000 G, 4° C., 20 minutes) and extensively washed with assay buffer. The membranes were subsequently analyzed in the RCB Assay using Example 7T. A bmax of 938 fmol/mg membranes was observed for unphotolysed membranes, whereas the bmax was reduced to 238 fmol/mg membranes after photolysing. However, the $K_d$ for Example 7T was not statistically significantly changed. These results indicate that Example 11 is cross-linked to the membrane binding site of Example 7.

Bmax is understood by one skilled in the art to represent the maximum number of binding sites in a cell membrane. See Mary Keen (Ed.) Receptor binding techniques. Methods in Molecular Biology, Vol 106, Humana Press, Totowa, N.J., 1999.

In this experiment the membranes were photolysed at 365 nm, which is appropriate for activation of the benzophenone moiety of Example 11. It is understood that photolysation of the membranes can occur at any wavelength that activates a photoactive tag to cross link to the protein. Such wavelengths generally occur in the 250 to 450 nm range.

Example 103

Analysis of Cross-Linked Polypeptides by SDS-PAGE:

THP-1 cell membranes were incubated with Example 11T exactly as outlined under the methods for the RCB Assay of the invention in the presence of an unlabeled competing compound; for Example 98 or Example 99. After 1 hour incubation at room temperature, the membranes were analyzed by the RCB assay (top panel, FIG. 1). The membranes in parallel wells were photolysed (365 nm, as in Example 102) for 30 minutes on ice (alternatively, at room temperature). Membranes were collected, boiled in SDS-containing buffer in the absence (middle panel FIG. 1) or presence of dithiothreitol (50 M) (bottom panel FIG. 1) and fractionated by SDS-PAGE (12% acrylamide in the separating gel). The polyacrylamide was fixed in 10% acetic acid/20% methanol/70% water for 45 minutes at room temperature and soaked for another 45 minutes in Amplify™ (Amersham). After drying, the gel was exposed to X-ray film. In the absence of a competing compound, labeling of a number of polypeptides was observed. However, based on the ability of unlabeled compounds to compete with the cross-linking reaction, major polypeptides, that could be specifically cross-linked with Example 11T, of molecular sizes of 30 (band A), 25 (band B), 20 (band C), and 10–12 (band D) kD were identified.

Dose-response experiments using increasing concentrations in the range of 1 picomolar to 100 micromolar of an unlabeled competing compound were performed. The resulting samples were either analyzed by the RCB Assay of the invention prior to photolysis or by SDS-PAGE after photolysis. A statistically significant correlation was observed between the competition in the radioligand competition binding assay and the radioactivity incorporated into the 30 (band A), 25 (band B), 20 kD (band C), and 10–12 kD (band D) bands as revealed by SDS-PAGE and fluorography.

Thus, the quantitative reduction of cross-linking by unlabeled compounds to the 30, 25, 20, and 10–12 kD bands accurately tracks the reduction of specific binding in the binding assay. These results indicate that identification of the cross-linked species will identify the site of interaction in the binding assay.

FIG. 1 illustrates the correlation between results of the RCB assay and the cross-linking assay for DMSO (lane 1), Example 7 (lane 2), Example 98b (lane 3), Example 43 (lane 4), Example 99 (lane 5), and Example 11 (lane 6) at 1 micromolar. FIG. 1, top panel, illustrates results of the RCB Assay for thesae compounds. FIG. 1, middle panel, illustrates results of the cross-linking assay for these compounds under non-reducing conditions. FIG. 1, bottom panel, illustrates results of the cross-linking assay for these compounds under reducing conditions. Membranes were incubated with Example 11T and DMSO or a number of unlabeled compounds and analyzed by RCB assay. The total radioactivity associated with the filter off is indicated. Parallel wells were photolysed as in Example 103, and the membrane extracts were analyzed by SDS-PAGE followed by fluorography. The mobility of molecular weight markers (in kD) is indicated to the right. Note specific cross-linking to polypeptides of 30 (band A), 25 (band B), 20 (band C), and 10–12 (band D) polypeptides. The radioactivity associated with band A is stronger than that in bands B to D, suggesting that band A might be a mixture of two polypeptides (i.e., presenilin 1 and presenilin 2; see FIG. 4).

Example 104

Immunological Identification of the 30 kD and 20 kD Cross-Linked Polypeptides of Example 103:

THP-1 cell membranes (1 mg/ml) in 50 mM TRIS buffer, pH 7.4–7.5, were incubated with Example 11T for 1 hour at room temperature and photolysed (as stated above) at room temperature for 30 minutes. The membranes were collected by centrifugation. The membranes were extracted with 50 mM Tris, pH 7.5 containing 100 mM KCl, 2 mM EDTA, 2% CHAPS and 1 complete protease inhibitor tablet per 25 ml buffer (COMPLETE™, Boehringer Mannheim; product number 1697 498)) for 1 hour at 4° C. The detergent soluble fraction was recovered by centrifugation (40,000 g, 30 min, 4° C.). The membrane extract was diluted one half with water. 500 ul of the membrane extract were pre-incubated with 10 ul of normal mouse IgG and 50 ul anti-mouse IgG Sepharose (Sigma) for 1 hour at 4° C. The supernatant was recovered by centrifugation. Subsequently, 10 ug of preimmune IgG (Sigma) or 10 ug of a monoclonal antibody to presenilin 1 was added in the presence of 50 ul anti-mouse IgG Sepharose. Examples of commercially available antibodies to presenilin 1 are Chemicon International: rat anti-human Presenilin 1 monoclonal antibody; product number MAB 1563; or Santa Cruz Biotechnology: goat anti Presenilin 1; product number SC-1244; or Santa Cruz Biotechnology: goat anti Presenilin 1; product number SC-1245. For use with goat antibodies, the immunoprecipitation was altered as follows: normal goat IgG and protein G Sepharose was used for the pre-absorption and protein G Sepharose was used in the presence of the goat antibodies to presenilin 1. The membrane extract was incubated for 5 hours at 4° C. The Sepharose beads were collected by centrifugation and washed 3 times with 25 mM Tris, pH 7.5 containing 50 mM KCl, 1 mM EDTA and 1% CHAPS, followed by 3 washes with phosphate buffered saline. Radioactivity bound to the Sepharose beads was dissociated by boiling in SDS sample buffer (4×) containing 50 mM dithiothreitol. The supernatant was loaded onto a 12% SDS-PAGE and the gel was processed as above. Fluorography revealed the presence of the approximately 30 (band A), 20 (band C), and 10 kD (band D) polypeptides in the immunoprecipitation with antibodies to presenilin 1, but not with normal mouse IgG. (FIG. 2) These results indicate that the membrane binding assay determines, at least in part, the binding of radiolabeled secretase inhibitors to presenilin 1 fragments.

Subsequent experiments established that the lack of polypeptide B in the initial immunoprecipitation experiments was due to aggregation upon boiling of the sample in reduced SDS sample buffer, indicating that all specifically labeled polypeptides (A to D) can be specifically immunoprecipitated with antibodies to presenilin 1 under non-denaturing conditions.

Figure 2:
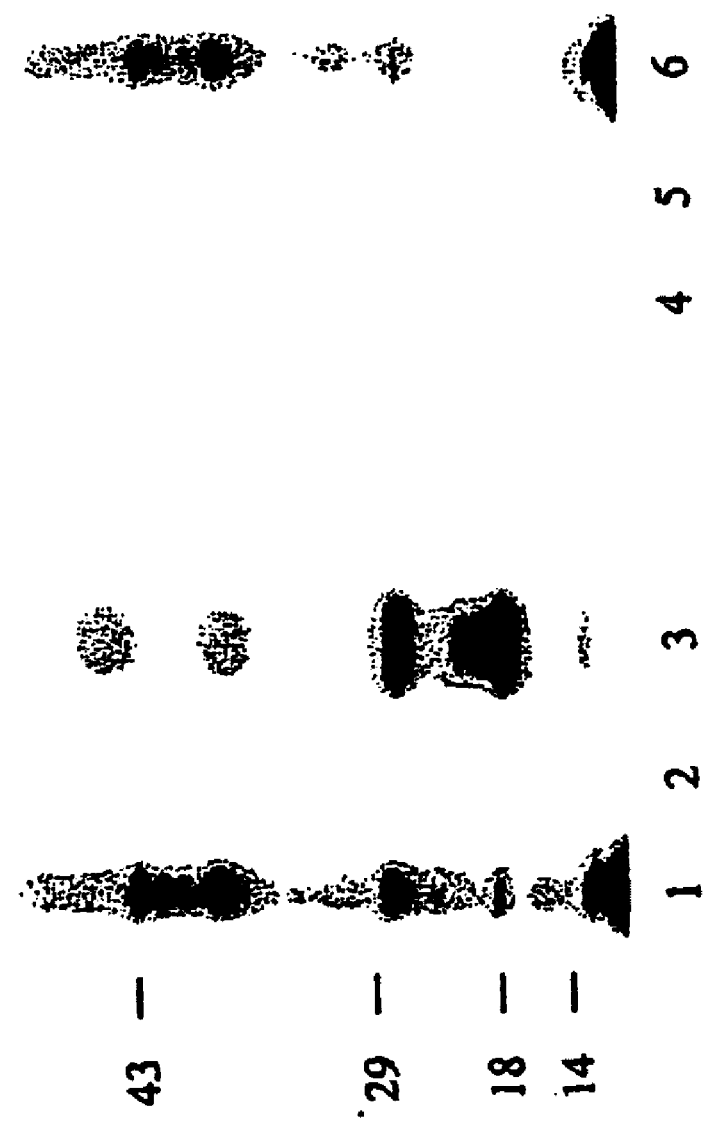
FIG. 2 illustrates a fluorography of a 12% SDS-PAGE after immunoprecipitation of specifically cross-linked polypepetides by presenilin-1 antibodies.

FIG. 2 illustrates a fluorography of a 12% SDS-PAGE. The relative mobility of molecular weight standards (in kD) is indicated to the left. THP-1 membranes were incubated (30 minutes; room temperature) with Example 43T (30 nM) alone (panel A) or Example 43T (30 nM) in the presence of Example 98 (panel B). The membranes were photolysed at 365 nm for 30 minutes and the membranes harvested by centrifugation. The membranes were extracted with 50 mM Tris, pH 7.5 containing 100 mM KCl, 2 mM EDTA, 2% CHAPS in the presence of protease inhibitors for 1 hour at 4° C. The membrane extracts were either directly fractionated by SDS-PAGE (lanes 1 and 6) or after immunoprecipitation with preimmune IgG (lanes 2 and 4) or antibodies to human presenilin 1 (lanes 3 and 5). Note the immunoprecipitation of specifically labeled bands of approximately 30, 20, and 10 kD after cross-linking in the absence of Example 98, but not in the presence of Example 98. The higher molecular weight bands may represent the presenilin 1 holoprotein and/or presenilin 1 aggregates formed in the presence of SDS.

Example 105

Purification of Cross-Linked Polypeptides by Affinity Chromatography

THP-1 membranes were prepared and cross-linked as in Example 104. The membranes were extracted as in Example 104 at a protein concentration of 10 mg membrane protein/1 ml extraction buffer. Normal mouse IgG (Sigma) or monoclonal antibody to the C-terminal loop of presenilin 1 was immobilized on agarose beads at 2 mg IgG per 1 ml of beads. The membrane extract was diluted one half with water and applied to a normal mouse IgG precolumn, followed by anti-presenilin 1 IgG. The column material was extensively washed with one half diluted extraction buffer, one half diluted extraction buffer containing 1M KCl, and eluted with 0.1 M glycine, pH 2.5 in one half diluted extraction buffer. The resulting polypeptides were analyzed by SDS-PAGE (12% acrylamide in the separating gel), followed by fluorography (left top panel, FIG. 3), silver staining (right top panel, FIG. 3), immunoblotting using antibodies to the N-terminus of presenilin (left middle panel, FIG. 3) or the C-terminus of presenilin 1 (right middle panel, FIG. 3). In addition, the silver stain (right top panel, FIG. 3) was soaked in Amplify™ (Amersham), dried, and exposed the x-ray film. It is concluded that the specifically cross-linked bands A, B, and C can be enriched by presenilin 1 affinity chromatography. It should be noted that using an antibody to the N-terminus of presenilin 1, also band D could be enriched. Polypeptides A and C are major silver stained protein bands containing the cross-linker of Example 11T and are immunoreactive with antibodies to presenilin 1. It should be noted that the extraction procedure used will not dissociate the association of macromolecules in the presenilin complex. Accordingly, one skilled in the art will understand that this technique can be employed to identify macromolecules associated with the binding site that are involved in beta amyloid precursor processing.

Figure 3:
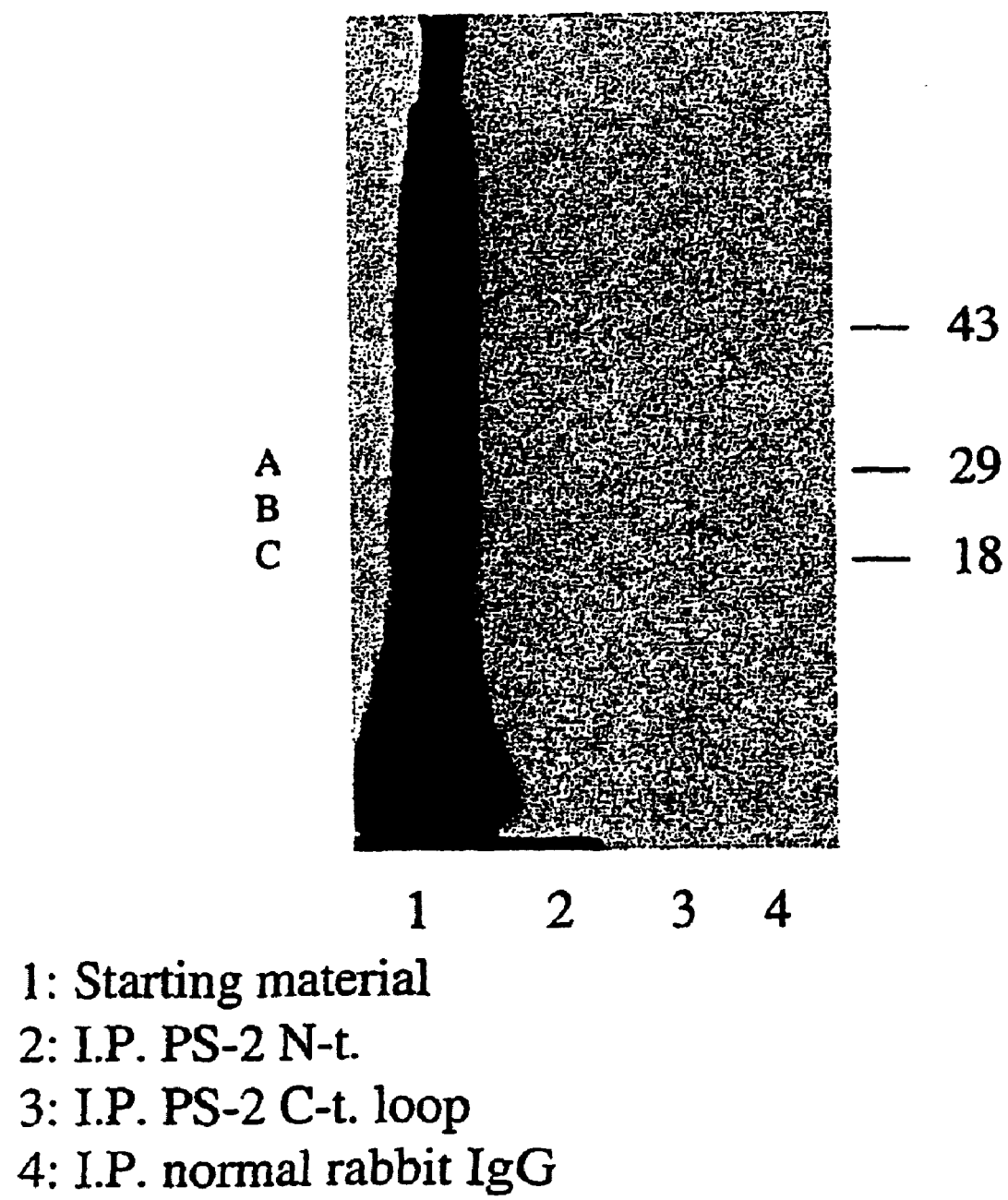
FIG. 3 illustrates isolation of cross-linked polypeptides by presenilin 1 affinity chromatography.

FIG. 3 illustrates isolation of cross-linked polypeptides by presenilin 1 affinity chromatography. THP-1 membranes were cross-linked as in FIG. 2 and the resulting membrane extracts were applied to a normal mouse IgG Sepharose, followed by an anti-presenilin 1 Sepharose. The starting material (lanes 1), flow-through normal mouse IgG (lanes 2), flow-through presenilin 1 Sepharose (lanes 3), last wash prior to elution (lanes 4), and elution by lowering the pH (lanes 5) are indicated. The relative mobility of molecular weight markers is indicated. The left top panel shows a fluorography of a 12% SDS-PAGE. Note the enrichment of bands A to C on the presenilin 1 affinity column. The silver stain (top right panel) reveals that bands A and C are clearly enriched, distinguishable from contaminating proteins, and present. in purity sufficient for sequence analysis. The silver stain was soaked in Amplify™ (Amersham), dried, and exposed to x-ray film (bottom left panel). It should be noted that major polypeptides in the elution fraction as revealed by silver staining perfectly align with the radioactivity as revealed by fluorography. The identify of band A as presenilin 1 N-terminal fragments was revealed by immunoblotting using N-terminal-specific antibodies (left middle panel), whereas band C was identified as presenilin C-terminal fragments (right middle panel).

It is understood by one skilled in the art that this or similar purification schemes can be employed to isolate radiolabeled binding polypeptides in sufficient quantities to allow for N-terminal amino acid or mass spectoscropy analysis. Also, one skilled in the art understands that isolated radiolabeled polypeptides can be further fractionated after chemical or proteolytic digestion to isolate one or several radiolabeled polypeptides in the sizes of approximately 2 to 100 amino acids. Sequence analysis will reveal the location of the smaller polypeptides in the protein sequence of the binding site molecules. In addition, this method can be used to define specifically cross-linked amino acids in the binding site. This information can ultimately be used in rational drug design for Alzheimer's disease. It should be noted that both N- and C-terminal presenilin 1 fragments are labeled by Example 11T. This observation is consistent with the notion that the binding site is contained in proteolytic fragments of presenilin 1 generated upon incorporation in the presenilin 1 complex.

Example 106

Evidence for the Involvement of Presenilin 2 in the Binding Site

THP-1 membranes were prepared and analyzed as in Example 104. The presenilin 1 antibodies were replaced with rabbit polyclonal antibodies specific for presenilin 2. The following modifications were included in comparison to Example 104: samples were pre-absorbed with normal rabbit IgG and protein A Sepharose was used instead of anti-mouse IgG Sepharose. The resulting immunoprecipitates were analyzed by SDS-PAGE (12% acrylamide in the separating gel) followed by fluorography. (See FIG. 4) Bands A and B was specifically precipitated with an antibody to presenilin 2 (N-terminus), whereas antibodies to the C-terminus of presenilin 2 preferentially identified band B. These results indicate that the membrane binding assay determines, at least in part, the binding of radiolabeled secretase inhibitors to presenilin 2 fragments. One skilled in the art will realize that the cross-linking assay can be used to identify compounds with preferential affinity for either presenilin 1 or 2. Membranes derived from organisms lacking either presenilin 1 or 2, or both, might be used for the same purpose.

Figure 4:
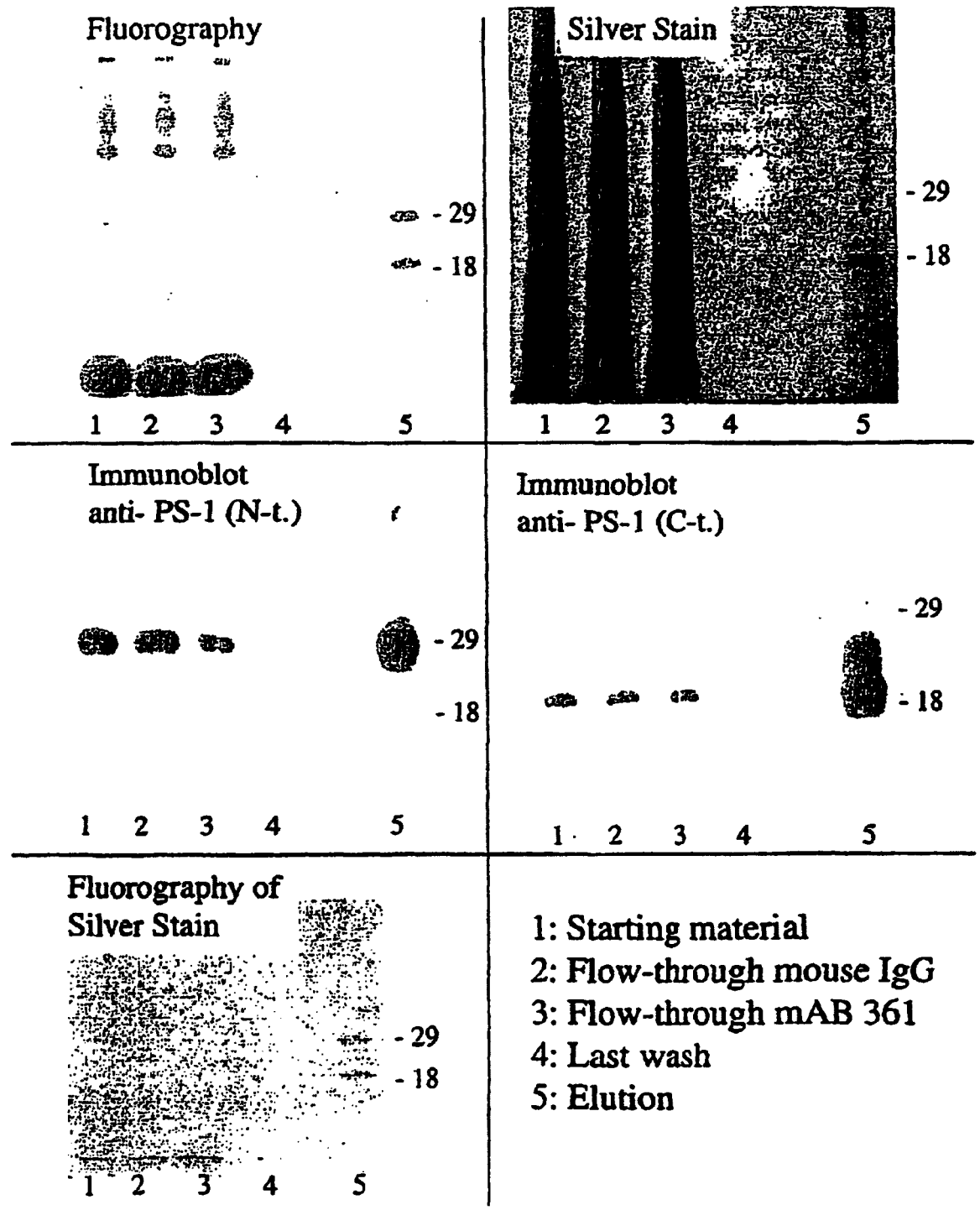
FIG. 4 illustrates a fluorography of a 12% SDS-PAGE after immunoprecipitation of specifically cross-linked polypepetides by presenilin-2 antibodies.

FIG. 4 illustrates a fluorography of a 12% SDS-PAGE. The relative mobility of molecular weight standards (in kD) is indicated to the right. THP-1 membranes were incubated (30 minutes; room temperature) with Example 11T, photolyzed at 365nm for 30 minutes, and the membranes harvested by centrifugation. The membranes were extracted with 50 mM Tris, pH 7.5 containing 100 mM KCl, 2 mM EDTA, 2% CHAPS in the presence of protease inhibitors for 1 hour at 4° C. The membrane extracts were either directly fractionated by SDS-PAGE (lane 1) or after immunoprecipitation with preimmune IgG (lane 4) or antibodies to human presenilin 2 (lane 2, PS-2 N-terminal specific antibody; lane 3, PS-2 C-terminal specific antibody). Note the immunoprecipitation of specifically labeled bands A and B of approximately 30 and 25 kD.

It is understood by one skilled in the art that the assays disclosed herein, specifically the Radio Competition Binding Assay and the cross-linking Assay may be employed to differentiate between inhibitors specific for presenilin-1 and presenilin-2. For example, differential competition for radioactivity incorporation in bands A to D would indicate presenilin-1 and/or presenilin-2 specific compounds. Moreover, binding to membranes derived from mammalian cells deficient in either PS-1 or PS-2 may be employed to identify PS-1 or PS-2 specific compounds. For example these cells may be derived from organisms, for example murine, which are gene targeted for PS-1 or PS-2. Examples of cells include fibroblasts, neurons, and whole embryonic membranes.

It is understood that the isolation and sequence data for presenilin-1 (PS-1) cloning has been published in Sherrington R et al., Nature, Vol 375, pp754–760, 1995, herein incorporated by reference. It is also understood that the isolation and sequence data for presenilin-2 (PS-2) cloning has been published in Rogaev E.I. et al., Nature, Vol 376, pp 774–778, 1995, herein incorporated by reference.

In Vivo Diagnostic Imaging Utility

The radiolabeled compounds of the invention are useful as radiopharmaceuticals for imaging sites involved in beta-amyloid production, and thus may be used to diagnose present or potential disorders involving beta-amyloid production, including but not limited to Alzheimer's disease. The patient may be any type of a mammal, but is preferably a human. The radiolabeled compounds may be used alone, or may be employed as a composition with a radiopharmaceutically acceptable carrier, and/or in combination with other diagnostic or therapeutic agents. Suitable radiopharmaceuticals carriers and suitable amounts thereof are well known in the art, and can be found in, for example, Remington's Pharmaceutical Sciences, Gennaro, A. R., ed., Mack Publishing Company, Easton, Pa. (1985), and The United States Pharmacopia—The National Formulary, 22nd Revision, Mack Printing Company, Easton, Pa. (1990), standard reference texts in the pharmaceutical field. Other materials may be added, as convenient, to stabilize the composition, as those skilled in the art will recognize, including antioxidizing agents such as sodium bisulfite, sodium sulfite, ascorbic acid, gentisic acid or citric acid (or their salts) or sodium ethylenediamine tetraacetic acid (sodium EDTA), as is well known in the art. Such other materials, as well as suitable amounts thereof, are also described in Remington's Pharmaceutical Sciences and The United States Pharmacopia—The National Formulary, cited above.

The present invention also includes radiopharmaceutical kits containing the labeled compounds of the invention.

Such kits may contain the labeled compounds in sterile lyophilized form, and may include a sterile container of a radiopharmaceutically acceptable reconstitution liquid. Suitable reconstitution liquids are disclosed in Remington's Pharmaceutical Sciences and The United States Pharmacopia—The National Formulary, cited above. Such kits may alternatively contain a sterile container of a composition of the radiolabeled compounds of the invention. Such kits may also include, if desired, other conventional kit components, such as, for example, one or more carriers, one or more additional vials for mixing. Instructions, either as inserts or labels, indicating quantities of the labeled compounds of the invention and carrier, guidelines for mixing these components, and protocols for administration may also be included in the kit. Sterilization of the containers and any materials included in the kit and lyophilization (also referred to as freeze-drying) of the labeled compounds of the invention may be carried out using conventional sterilization and lyophilization methodologies known to those skilled in the art.

To carry out the method of the invention, the radiolabeled compounds are generally administered intravenously, by bolus injection, although they may be administered by any means that produces contact of the compounds with sites of beta-amyloid production, particularly in sites in the brain. Suitable amounts for administration will be readily ascertainable to those skilled in the art, once armed with the present disclosure. The dosage administered will, of course, vary depending up such known factors as the particular compound administered, the age, health and weight or the nature and extent of any symptoms experienced by the patient, the amount of radiolabeling, the particular radionuclide used as the label, the rate of clearance of the radiolabeled compounds from the patient.

Acceptable ranges for administration of radiolabeled materials are tabulated, for example, in the Physicians Desk Reference (PDR) for Nuclear Medicine, published by Medical Exonomics Company, a well-known reference text. A discussion of some of the aforementioned considerations is provided in Eckelman et al., J. Nucl. Med., Vol. 209, pp. 350–357 (1979). By way of general guidance, a dosage range of the radiolabeled compounds of the invention may be between about 1 and about 40 mCi.

Once the radiolabeled compounds of the invention are administered, the presence of sites involved in beta-amyloid production may be visualized using standard imaging systems. Such imaging systems are well known in the art, and are discussed, for example, in Macovski, A., Medical Imaging Systems, Information and Systems Science Series, Kailath, T., ed., Prentice-Hall, Inc., Englewood Cliffs, N.J. (1983). Particularly preferred is positron emission tomography (PET). Specifically, imaging is carried out by scanning the entire patient, or a particular region of the patient using the detection system, and detecting the radioisotope signal. The detected signal is then converted into an image. The resultant images should be read by an experienced observer, such as, for example, a nuclear medicine physician. The foregoing process is referred to herein as "imaging" the patient. Generally, imaging is carried out about 1 minute to about 48 hours following administration of the radiolabeled compound of the invention. The precise timing of the imaging will be dependant upon such factors as the half-life of the radioisotope employed, and the clearance rate of the compound administered, as will be readily apparent to those skilled in the art. Preferably, imaging is carried out between about 1 minute and about 4 hours following administration.

The advantage of employing the radiolabeled compounds of the invention, which have the ability to localize specifically and with high affinity in sites involved in beta-amyloid production, to detect the presence of such sites involved in beta-amyloid production and/or to diagnose disorders in a patient involving beta-amyloid production, will be readily apparent to those skilled in the art, once armed with the present disclosure.

Dosage and Formulation

The compounds determined from the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds determined from the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds determined from the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

Advantageously, compounds determined from the present invention may be administered in a single daily dose, or the total daily dosage may be administered in divided doses of two, three, or four times daily.

The compounds identified using the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds determined from the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds determined from the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A method of screening for inhibitors of beta-amyloid production comprising,
   1) contacting a potential inhibitor of beta-amyloid production and a tagged inhibitor of beta-amyloid production with at least one macromolecule involved in the processing of APP and the production of beta-amyloid peptide, wherein the macromolecule is a secretase selected from α-secretase, β-secretase, and γ-secretase, said macromolecule containing a binding site specific for said tagged inhibitor of beta-amyloid production;
   2) separating the tagged inhibitor of beta-amyloid production bound to said macromolecule from the tagged inhibitor of beta-amyloid production free from said macromolecule; and
   3) determining an inhibitory concentration of the potential inhibitor of beta-amyloid production from the concentration of tagged inhibitor of beta-amyloid production bound to said macromolecule.

2. The method of claim 1 wherein the tagged inhibitor of beta-amyloid production comprises a radiolabeled inhibitor of beta-amyloid production, a fluorescence labeled inhibitor of beta-amyloid production or a biotin labeled inhibitor of beta-amyloid production.

3. The method of claim 1 wherein the tagged inhibitor of beta-amyloid production comprises a radiolabeled inhibitor of beta-amyloid production.

4. The method of claim 1 wherein the tagged inhibitor of beta-amyloid production comprises a tritium or iodine radiolabeled inhibitor of beta-amyloid production.

5. The method of claim 1 wherein the tagged inhibitor of beta-amyloid production comprises a tritium radiolabeled inhibitor of beta-amyloid production.

6. The method of claim 1 wherein the tagged inhibitor of beta-amyloid production comprises a compound of the Formula (I):

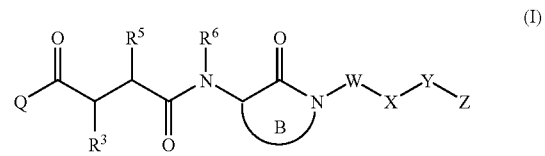

wherein:
at least one atom of the compound of the Formula (I) is radiolabeled;
Q is $NH_2$;
$R^3$ is $C_1$–$C_6$ alkyl substituted with 0–1 $R^4$;
$R^4$ is H, OH, $C_1$–$C_6$ alkyl, $C_2$–$C_6$ alkenyl, $C_2$–$C_6$ alkynyl, $C_3$–$C_{10}$ carbocycle, $C_6$–$C_{10}$ aryl, or 5 to 10 membered heterocycle;
$R^5$ is H, $OR^{14}$;

$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle substituted with 0–3 $R^{5c}$;
$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle substituted with 0–3 $R^{5c}$;
$R^{5c}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3$R^{6b}$;
$R^{6a}$, at each occurrence, is independently selected from H, $C_1$–$C_6$ alkyl, $OR^{14}$, Cl, F, Br, I, =O, CN, $NO_2$, $NR^{15}R^{16}$, phenyl or $CF_3$;
$R^{6b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
W is —$(CR^8R^{8a})_p$—;
p is 0 to 4;
$R^8$ and $R^{8a}$, at each occurrence, are independently selected from H, $C_1$–$C_4$ alkyl, $C_2$–$C_4$ alkenyl, $C_2$–$C_4$ alkynyl and $C_3$–$C_8$ cycloalkyl;
X is a bond;
$C_6$–$C_{10}$ aryl substituted with 0–3 $R^{Xb}$;
$C_3$–$C_{10}$ carbocycle substituted with 0–3 $R^{Xb}$; or
5 to 10 membered heterocycle substituted with 0–3 $R^{Xb}$;
$R^{Xb}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
Y is a bond or —$(CR^9R^{9a})_t$-V—$(CR^9R^9a)_u$-;
t is 0 to 3;
u is 0 to 3;
$R^9$ and $R^{9a}$, at each occurrence, are independently selected from H, $C_1$–$C_6$ alkyl or $C_3$–$C_8$ cycloalkyl;
V is a bond, —C(=O)—, —O—, —S—, —S(=O)—, —S(=O)$_2$—, —N($R^{19}$)—, —C(=O)$NR^{19b}$—, $NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—;
Z is H;
$C_1$–$C_8$ alkyl substituted with 0–2 $R^{12}$;
$C_2$–$C_4$ alkenyl substituted with 0–2 $R^{12}$;
$C_2$–$C_4$ alkynyl substituted with 0–2 $R^{12}$;
$C_6$–$C_{10}$ aryl substituted with 0–4 $R^{12b}$;
$C_3$–$C_{10}$ carbocycle substituted with 0–4 $R^{12b}$; or
5 to 10 membered heterocycle substituted with 0–3 $R^{12b}$;
$R^{12}$ is $C_6$–$C_{10}$ aryl substituted with 0–4 $R^{12b}$;
$C_3$–$C_{10}$ carbocycle substituted with 0–4 $R^{12b}$; or
5 to 10 membered heterocycle substituted with 0–3 $R^{12b}$;
$R^{12b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

B is

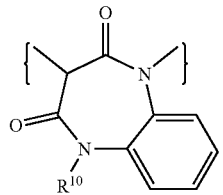 or 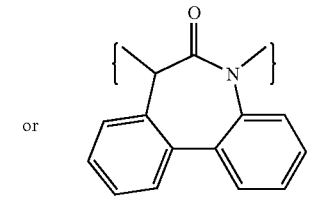

$R^{10}$ is H, C(=O)$R^{17}$, C(=O)$OR^{17}$, C(=O)$NR^{18}R^{19}$, S(=O)$_2$$NR^{18}R^{19}$, S(=O)$_2$$R^{17}$;
$C_1$–$C_6$ alkyl optionally substituted with $R^{10a}$;
$C_6$–$C_{10}$ aryl substituted with 0–4 $R^{10b}$;
$C_3$–$C_{10}$ carbocycle substituted with 0–3 $R^{10b}$; or
5 to 10 membered heterocycle optionally substituted with 0–3 $R^{10b}$;
$R^{10a}$, at each occurrence, is independently selected from H, $C_1$–$C_6$ alkyl, $C_3$–$C_6$ cycloalkyl, $OR^{14}$, Cl, F, Br, I, =O, CN, $NO_2$, $NR^{15}R^{16}$, phenyl or $CF_3$;
$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
$R^{14}$ is H, phenyl, benzyl, $C_1$–$C_6$ alkyl, or $C_2$–$C_6$ alkoxyalkyl;
$R^{15}$, at each occurrence, is independently selected from H, $C_1$–$C_6$ alkyl, benzyl, phenethyl, —C(=O)—($C_1$–$C_6$ alkyl) and —S(=O)$_2$—($C_1$–$C_6$ alkyl);
$R^{16}$, at each occurrence, is independently selected from H, OH, $C_1$–$C_6$ alkyl, benzyl, phenethyl, —C(=O)—($C_1$–$C_6$ alkyl) and —S(=O)$_2$—($C_1$–$C_6$ alkyl);
$R^{17}$ is H, phenyl, benzyl, $C_1$–$C_6$ alkyl, or $C_2$–$C_6$ alkoxyalkyl;
$R^{18}$, at each occurrence, is independently selected from H, $C_1$–$C_6$ alkyl, benzyl, phenethyl, —C(=O)—($C_1$–$C_6$ alkyl) and —S(=O)$_2$—($C_1$–$C_6$ alkyl); and
$R^{19}$, at each occurrence, is independently selected from H, OH, $C_1$–$C_6$ alkyl, phenyl, benzyl, phenethyl, —C(=O)—($C_1$–$C_6$ alkyl) and —S(=O)$_2$—($C_1$–$C_6$ alkyl); and
$R^{19b}$ is H, $C_1$–$C_6$ alkyl, $C_3$–$C_8$ cycloalkyl, phenyl, benzyl or phenethyl.

7. The method of claim 6 wherein $R^3$ is $C_3$–$C_6$ alkyl.

8. The method of claim 6 wherein $R^3$ is $C_3$–$C_6$ alkyl substituted with about 1 to about 4 $^3$H.

9. The method of claim 6 wherein the tagged inhibitor of beta-amyloid production comprises a compound of the Formula (II):

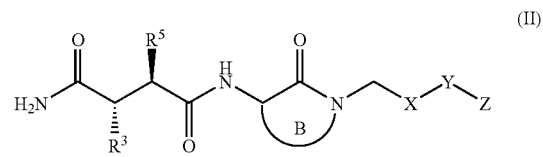

wherein:
at least one atom of the compound of the Formula (II) is radiolabeled.

10. The method of claim 9 wherein $R^3$ is $C_3$–$C_6$ alkyl substituted with about 1 to about 4 $^3$H.

11. The method of claim 1 wherein at least one macromolecule involved in the processing of APP and the production of beta-amyloid peptide comprises α, β or γ-secretase.

12. The method of claim 1 wherein at least one macromolecule involved in the processing of APP and/or the production of beta-amyloid peptide comprises:
(1) β secretase;
(2) α secretase; or
(3) γ secretase;
said macromolecule containing a binding site specific for said tagged inhibitor of beta-amyloid production.

13. The method of claim 1 wherein the inhibitory concentration is half maximal inhibitory concentration.

14. A pharmaceutical composition comprising a pharmaceutically acceptable carrier and a therapeutically effective amount of an inhibitor of beta-amyloid production identified by the screening assay of claim 1 or a pharmaceutically acceptable salt form thereof.

15. A method for treating Alzheimer's Disease, comprising administering to a host in need of such treatment a therapeutically effective amount of an inhibitor of beta-amyloid production identified by the screening assay of claim 1 or a pharmaceutically acceptable salt form thereof.

16. A method for treating Alzheimer's disease comprising administering to a host in need of such treatment a therapeutically effective amount of an inhibitor of beta-amyloid production identified by the screening assay of claim 1 or a pharmaceutically acceptable salt form thereof.

17. The method of claim 1 wherein the tagged inhibitor of beta-amyloid production comprises a radiolabeled inhibitor of beta-amyloid production, a fluorescence labeled inhibitor of beta-amyloid production, a biotin labeled inhibitor of beta-amyloid production.

18. The method of claim 1 wherein the tagged inhibitor of beta-amyloid production comprises a radiolabeled inhibitor of beta-amyloid production.

19. The method of claim 1 wherein the tagged inhibitor is radiolabeled with one or more radioisotope selected from $^3$H, $^{11}$C, $^{14}$C, $^{18}$F, $^{32}$P, $^{35}$S, $^{123}$I, $^{125}$I, and $^{131}$I.

20. An inhibitor of beta-amyloid production comprising a compound which interacts with a binding site on a macromolecule involved in the production of beta-amyloid peptide; wherein said binding site is a specific binding site for a compound of Formula as claimed in claim 1 wherein ring B is

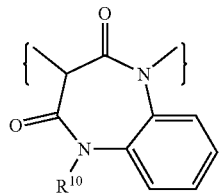 or 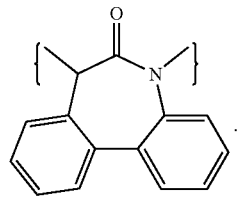.

21. An inhibitor of beta-amyloid production of claim 20 wherein the macromolecule involved in the production of beta-amyloid peptide is α secretase, β secretase, or γ secretase, containing a binding site specific for said tagged inhibitor of beta-amyloid production.

22. An inhibitor of beta-amyloid production of claim 20 wherein the macromolecule involved in the production of beta-amyloid peptide is γ secretase, containing a binding site specific for said tagged inhibitor of beta-amyloid production.

23. An inhibitor of beta-amyloid production of claim 20 comprising a compound which interacts with a binding site on a macromolecule involved in the production of beta-amyloid peptide; wherein said compound demonstrates a half maximal inhibitory concentration less than 10 micromolar for beta-amyloid production.

24. An inhibitor of beta-amyloid production of claim 20 comprising a compound which interacts with a binding site on γ gamma-secretase; wherein the compound demonstrates a half maximal inhibitory concentration less than 10 micromolar for beta-amyloid production.

25. An inhibitor of beta-amyloid production of claim 6 comprising a compound which interacts with a binding site on a macromolecule involved in the production of beta-amyloid peptide; wherein said binding site is a specific binding site for a compound of Formula (I) wherein B is

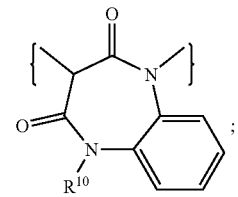

and the compound demonstrates a half maximal inhibitory concentration of less than 10 micromolar for beta-amyloid production.

26. An inhibitor of beta-amyloid production of claim 6 comprising a compound which interacts with a binding site on γ-secretase; wherein said binding site is a specific binding site for a compound of Formula (I) wherein B is

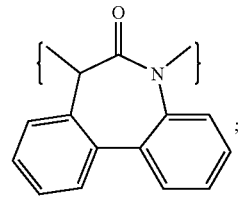

and the compound demonstrates a half maximal inhibitory concentration less than 10 micromolar for beta-amyloid production.

27. A tagged inhibitor of beta-amyloid production of claim 6 comprising a tagged compound which interacts with a binding site on a macromolecule involved in the production of beta-amyloid peptide; wherein said binding site is a specific binding site for a compound of Formula (I) wherein ring B is:

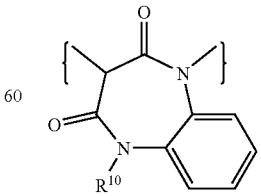 or 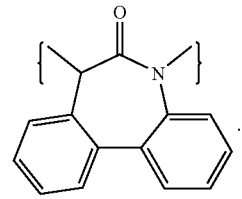.

28. A tagged inhibitor of beta-amyloid production of claim 27 wherein the macromolecule involved in the production of beta-amyloid peptide is α, β, or γ-secretase, containing a binding site specific for said tagged inhibitor of beta-amyloid production.

29. A tagged inhibitor of beta-amyloid production of claim 27 wherein the macromolecule involved in the production of beta-amyloid peptide is secretase or a fragment thereof, containing a binding site specific for said tagged inhibitor of beta-amyloid production.

30. A tagged inhibitor of beta-amyloid production of claim 27 comprising a tagged compound which interacts with a binding site on a macromolecule involved in the production of beta-amyloid peptide; wherein said tagged compound demonstrates a half maximal inhibitory concentration less than 10 micromolar for beta-amyloid production.

31. A tagged inhibitor of beta-amyloid production of claim 27 comprising a tagged compound which interacts with a binding site on α, β, or γ-secretase; wherein said tagged compound demonstrates a half maximal inhibitory concentration less than 10 micromolar for beta-amyloid production.

32. A tagged inhibitor of beta-amyloid production of claim 6 comprising a tagged compound which interacts with a binding site on a macromolecule involved in the production of beta-amyloid peptide; wherein said binding site is a specific binding site for a compound of Formula (I) wherein ring B is

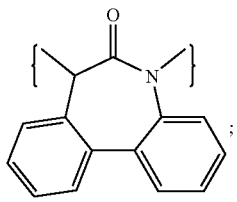

and the tagged compound demonstrates a half maximal inhibitory concentration less than 10 micromolar for beta-amyloid production.

33. A tagged inhibitor of beta-amyloid production of claim 32 comprising a tagged compound which interacts with a binding site on presenilin 1 or a fragment of presenilin 1; wherein said binding site is a specific binding site for a compound of Formula (I) wherein ring B is:

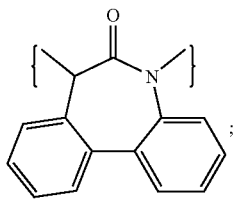

and the tagged compound demonstrates a half maximal inhibitory concentration less than 10 micromolar for beta-amyloid production.

34. A method of treating Alzheimer's disease comprising administering to a host in need of such treatment a therapeutically effective amount of an inhibitor of beta-amyloid production, or a pharmaceutically acceptable salt or prodrug form thereof, wherein said inhibitor of beta-amyloid production binds to a binding site on a macromolecule involved in the production of beta-amyloid peptide and effects a decrease in production of beta-amyloid peptide;

wherein said binding site is a specific binding site for a compound of Formula (I) of claim 6 wherein ring B is:

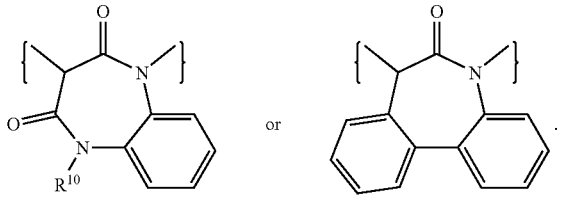

35. The method of claim 34 wherein the macromolecule comprises α-secretase, β-secretase, or γ-secretase, containing a binding site specific for said tagged inhibitor of beta-amyloid production.

36. A method of claim 34 wherein the binding site is a specific binding site for a compound of Formula (I) wherein ring B is:

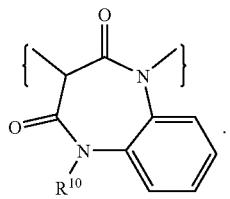

37. The method of claim 36 wherein the macromolecule comprises α secretas, β secretase, or γ secretase, containing a binding site specific for said tagged inhibitor of beta-amyloid production.

38. The method of claim 36 wherein the macromolecule comprises γ-secretase, containing a binding site specific for said tagged inhibitor of beta-amyloid production.

39. A method of in vivo diagnostic imaging comprising administering to a subject a diagnostically effective amount of a radiolabeled inhibitor of claim 6 of beta-amyloid production.

40. A method of claim 39 wherein said method is used in the diagnosis of a neurological disease which involves APP processing or elevated levels of beta-amyloid, or both.

41. A method of claim 39 wherein said method is used in the diagnosis of Alzheimer's disease.

42. A method of claim 39 wherein the radiolabeled inhibitor is suitable for imaging of the brain of the subject.

43. A method of claim 39 wherein the radiolabeled inhibitor is radiolabeled with one or more radioisotope selected from $^{3}H$, $^{11}C$, $^{14}C$, $^{18}F$, $^{32}P$, $^{35}S$, $^{123}I$, $^{125}I$, and $^{131}I$.

44. The method of claim 39 wherein the tagged inhibitor of beta-amyloid production is a compound selected from the group found binding a γ-secretase at a binding site specific for said tagged inhibitor of beta-amyloid production, consisting of 5-amino-6-cyclohexyl-4-hydroxy-hexanamide derivatives, N-aryl amino acid esters, N-heteroaryl amino acid esters, N-arylacetyl amino acid amides, N-heteroarylacetyl amino acid amides, and N-alkylacetyl amino acid amides, N-arylacetyl amino acid esters, N-heteroarylacetyl amino acid esters, and N-alkylacetyl amino acid esters, N-aryl amino acid derivatives, N-heteroaryl amino acid derivatives, and cycloalkyl. lactam, lactone and related compounds.

45. A method of claim 39 wherein the inhibitor of β amyloid production exhibits activity as an inhibitor γ secretase.

46. A method of claim 39 wherein the inhibitor of beta-amyloid production is selected from:
   (1) an inhibitor of β secretase;
   (2) an inhibitor of α secretase; and
   (3) an inhibitor of γ secretase.

47. A pharmaceutical composition comprising a compound of claim 6 suitable for in vivo diagnostic imaging comprising a radiolabeled inhibitor of beta-amyloid production.

48. A pharmaceutical composition of claim 47 wherein the composition is used in the diagnosis of a neurological disease which involves APP processing or elevated levels of beta-amyloid, or both.

49. A pharmaceutical composition of claim 47 wherein the composition is used in the diagnosis of Alzheimer's disease.

50. A pharmaceutical composition of claim 47 wherein the radiolabeled inhibitor is suitable for imaging of the brain of the subject.

51. A pharmaceutical composition of claim 47 wherein the radiolabeled inhibitor is radiolabeled with one or more radioisotope selected from $^{3}H$, $^{11}C$, $^{14}C$, $^{18}F$, $^{32}P$, $^{35}S$, $^{123}I$, $^{125}I$, and $^{131}I$.

52. A pharmaceutical composition of claim 47 wherein the inhibitor of beta-amyloid production is a compound selected from the group found binding a γ secretase, at a binding site specific for said tagged inhibitor of beta-amyloid production, consisting of 5-amino-6-cyclohexyl-4-hydroxy-hexanamide derivatives, N-aryl amino acid esters, N-heteroaryl amino acid esters, N-arylacetyl amino acid amides, N-heteroarylacetyl amino acid amides, and N-alkylacetyl amino acid amides, N-arylacetyl amino acid esters, N-heteroarylacetyl amino acid esters, and N-alkylacetyl amino acid esters, N-aryl amino acid derivatives, N-heteroaryl amino acid derivatives, and cycloalkyl, lactam, lactone and related compounds.

53. A pharmaceutical composition of claim 47 wherein the inhibitor of beta-amyloid production is an inhibitor of γ-secretase.

* * * * *